(12) United States Patent
LeVaughn et al.

(10) Patent No.: US 7,883,473 B2
(45) Date of Patent: *Feb. 8, 2011

(54) BLOOD SAMPLING DEVICE

(75) Inventors: Richard W. LeVaughn, Talking Rock, GA (US); Gwenn E. Kennedy, Ellenwood, GA (US); Christopher J. Ruf, Atlanta, GA (US); Mitchell Solis, Cumming, GA (US); Avi M. Robbins, Longwood, FL (US); Jason R. Heath, Marietta, GA (US); Wolfgang Ostertag, Gerstetten (DE); Armin Lohrengel, Steinheim (DE); Herbert Stohr, Grosskuchen (DE)

(73) Assignee: Facet Technologies, LLC, Kennesaw, GA (US)

( * ) Notice: Subject to any disclaimer, the term of this patent is extended or adjusted under 35 U.S.C. 154(b) by 1305 days.

This patent is subject to a terminal disclaimer.

(21) Appl. No.: 10/505,352

(22) PCT Filed: Feb. 20, 2003

(86) PCT No.: PCT/US03/05159

§ 371 (c)(1),
(2), (4) Date: Aug. 19, 2004

(87) PCT Pub. No.: WO03/071940

PCT Pub. Date: Sep. 4, 2003

(65) Prior Publication Data

US 2005/0015020 A1  Jan. 20, 2005

Related U.S. Application Data

(60) Provisional application No. 60/387,639, filed on Jun. 11, 2002, provisional application No. 60/411,834, filed on Sep. 17, 2002.

(51) Int. Cl.
*A61B 5/00* (2006.01)

(52) U.S. Cl. .................. 600/583; 606/181; 606/182; 600/584

(58) Field of Classification Search ............... 600/583, 600/584; 606/181–183
See application file for complete search history.

(56) References Cited

U.S. PATENT DOCUMENTS

| 4,627,445 A | 12/1986 | Garcia et al. |
| 4,750,851 A * | 6/1988 | Thomey .................. 411/360 |
| 4,787,398 A | 11/1988 | Garcia et al. |
| 4,794,926 A | 1/1989 | Munsch et al. |
| 4,823,806 A | 4/1989 | Bajada |

(Continued)

FOREIGN PATENT DOCUMENTS

DE  198 19 407 A1  11/1999

(Continued)

*Primary Examiner*—Max Hindenburg
*Assistant Examiner*—Michael C Stout
(74) *Attorney, Agent, or Firm*—Gardner Groff Greenwald & Villanueva, PC

(57) ABSTRACT

A device (302) for sampling and/or analyzing blood or other body fluid of a subject. A housing (306) contains a plurality of lancets (308) and optionally includes test elements (324) to take up a sample of blood, an evaluation system and a display. A complete system that can be handled as a single device, for example in the form of a wristwatch, includes a multiplicity of test elements (324) and lancets (308), which can be brought successively to a working position to perform multiple measurements. A cassette or carrier (320) includes multiple lancets (308) and/or test elements (324), for insertion into the device.

25 Claims, 35 Drawing Sheets

U.S. PATENT DOCUMENTS

| | | | |
|---|---|---|---|
| 4,974,926 A | | 12/1990 | Blee et al. |
| 5,152,775 A | * | 10/1992 | Ruppert ...................... 606/182 |
| 5,279,294 A | | 1/1994 | Anderson et al. |
| 5,318,584 A | | 6/1994 | Lange et al. |
| 5,385,571 A | * | 1/1995 | Morita ....................... 606/181 |
| 5,514,152 A | | 5/1996 | Smith |
| 5,628,765 A | | 5/1997 | Morita |
| 5,741,288 A | | 4/1998 | Rife |
| 5,871,494 A | | 2/1999 | Simons et al. |
| 5,951,492 A | | 9/1999 | Douglas et al. |
| 5,971,941 A | | 10/1999 | Simons et al. |
| 6,036,924 A | | 3/2000 | Simons et al. |
| 6,071,294 A | * | 6/2000 | Simons et al. ............... 606/181 |
| 6,099,484 A | | 8/2000 | Douglas et al. |
| 6,197,041 B1 | * | 3/2001 | Shichman et al. ........... 606/185 |
| 6,228,100 B1 | * | 5/2001 | Schraga ...................... 606/183 |
| 6,472,220 B1 | | 10/2002 | Simons et al. |
| 6,706,159 B2 | * | 3/2004 | Moerman et al. ...... 204/403.03 |
| 6,766,817 B2 | | 7/2004 | Da Silva |
| 7,150,755 B2 | * | 12/2006 | Levaughn et al. ........... 606/181 |
| 2002/0087056 A1 | | 7/2002 | Aceti et al. |
| 2002/0120216 A1 | * | 8/2002 | Fritz et al. ................... 600/583 |
| 2003/0073931 A1 | | 4/2003 | Boecker et al. |
| 2003/0083685 A1 | | 5/2003 | Freeman et al. |
| 2003/0199789 A1 | | 10/2003 | Boecker et al. |
| 2003/0199790 A1 | | 10/2003 | Boecker et al. |
| 2003/0199791 A1 | | 10/2003 | Boecker et al. |
| 2003/0199893 A1 | | 10/2003 | Boecker et al. |
| 2003/0199894 A1 | | 10/2003 | Boecker et al. |
| 2003/0199895 A1 | | 10/2003 | Boecker et al. |
| 2003/0199896 A1 | | 10/2003 | Boecker et al. |
| 2003/0199897 A1 | | 10/2003 | Boecker et al. |
| 2003/0199898 A1 | | 10/2003 | Boecker et al. |
| 2003/0199899 A1 | | 10/2003 | Boecker et al. |
| 2003/0199900 A1 | | 10/2003 | Boecker et al. |
| 2003/0199901 A1 | | 10/2003 | Boecker et al. |
| 2003/0199902 A1 | | 10/2003 | Boecker et al. |
| 2003/0199903 A1 | | 10/2003 | Boecker et al. |
| 2003/0199904 A1 | | 10/2003 | Boecker et al. |
| 2003/0199905 A1 | | 10/2003 | Boecker et al. |
| 2003/0199906 A1 | | 10/2003 | Boecker et al. |
| 2003/0199907 A1 | | 10/2003 | Boecker et al. |
| 2003/0199908 A1 | | 10/2003 | Boecker et al. |
| 2003/0199909 A1 | | 10/2003 | Boecker et al. |
| 2003/0199910 A1 | | 10/2003 | Boecker et al. |
| 2003/0199911 A1 | | 10/2003 | Boecker et al. |
| 2003/0212424 A1 | | 11/2003 | Briggs et al. |
| 2004/0009100 A1 | | 1/2004 | Simons et al. |
| 2004/0010279 A1 | | 1/2004 | Freeman et al. |
| 2004/0049220 A1 | | 3/2004 | Boecker et al. |
| 2004/0087990 A1 | * | 5/2004 | Boecker et al. ............. 606/181 |
| 2004/0092944 A1 | | 5/2004 | Penenberg |
| 2004/0092995 A1 | | 5/2004 | Boecker et al. |
| 2004/0098009 A1 | | 5/2004 | Boecker et al. |
| 2004/0102803 A1 | * | 5/2004 | Boecker et al. ............. 606/183 |

FOREIGN PATENT DOCUMENTS

| | | |
|---|---|---|
| DE | 100 57 832 C1 | 2/2002 |
| EP | 0 449 525 A1 | 3/1991 |
| EP | 0 811 843 A2 | 12/1997 |
| EP | 0 877 250 A2 | 11/1998 |
| EP | 0 949 506 A2 | 10/1999 |
| EP | 0 589 186 B1 | 11/1999 |
| EP | 0 985 376 A1 | 3/2000 |
| WO | WO 01/66010 A1 | 9/2001 |
| WO | WO 02/36010 A1 | 5/2002 |
| WO | WO 03/070099 | 8/2003 |
| WO | WO 03/088835 A2 | 10/2003 |

* cited by examiner

SECTION A-A

SECTION B-B

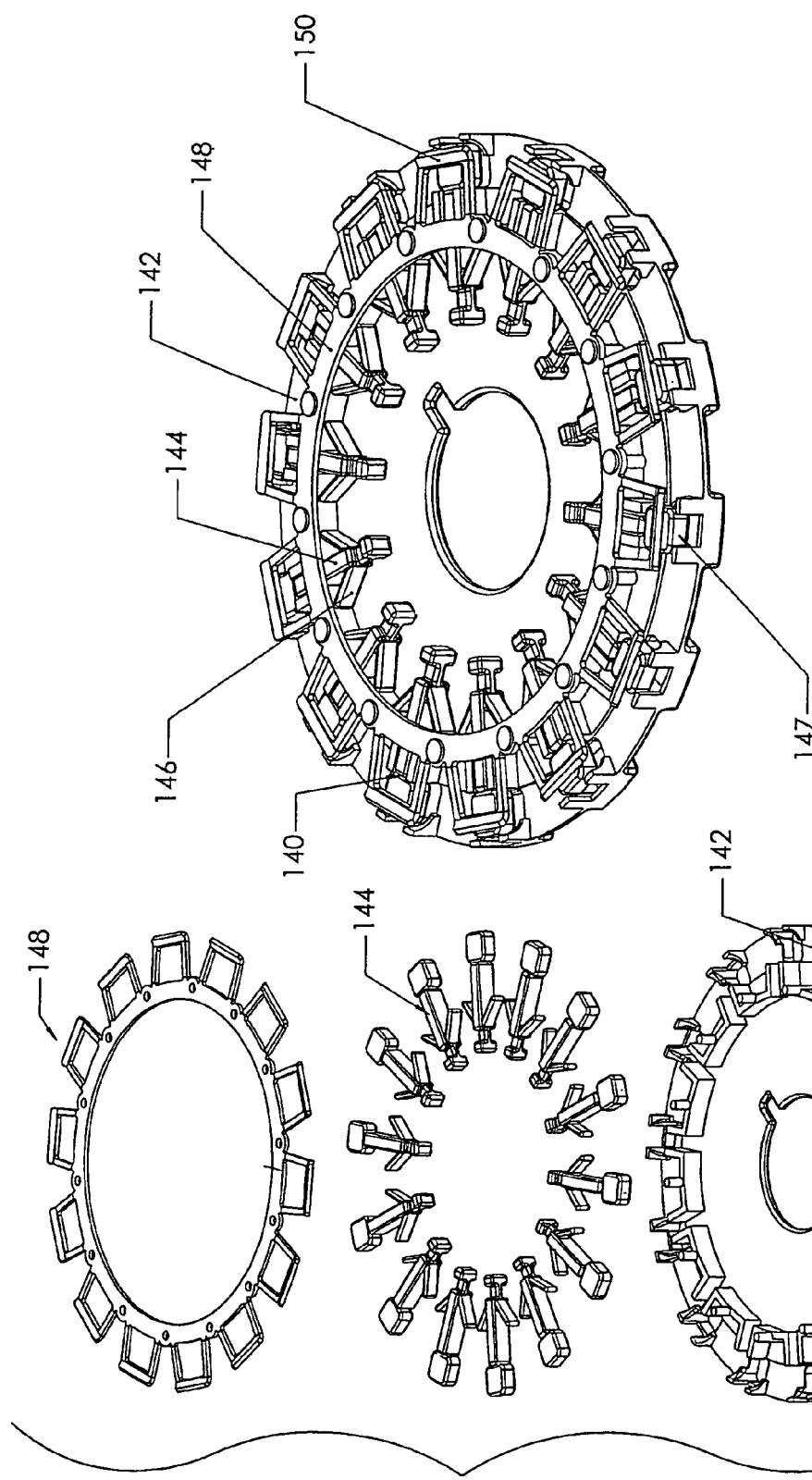

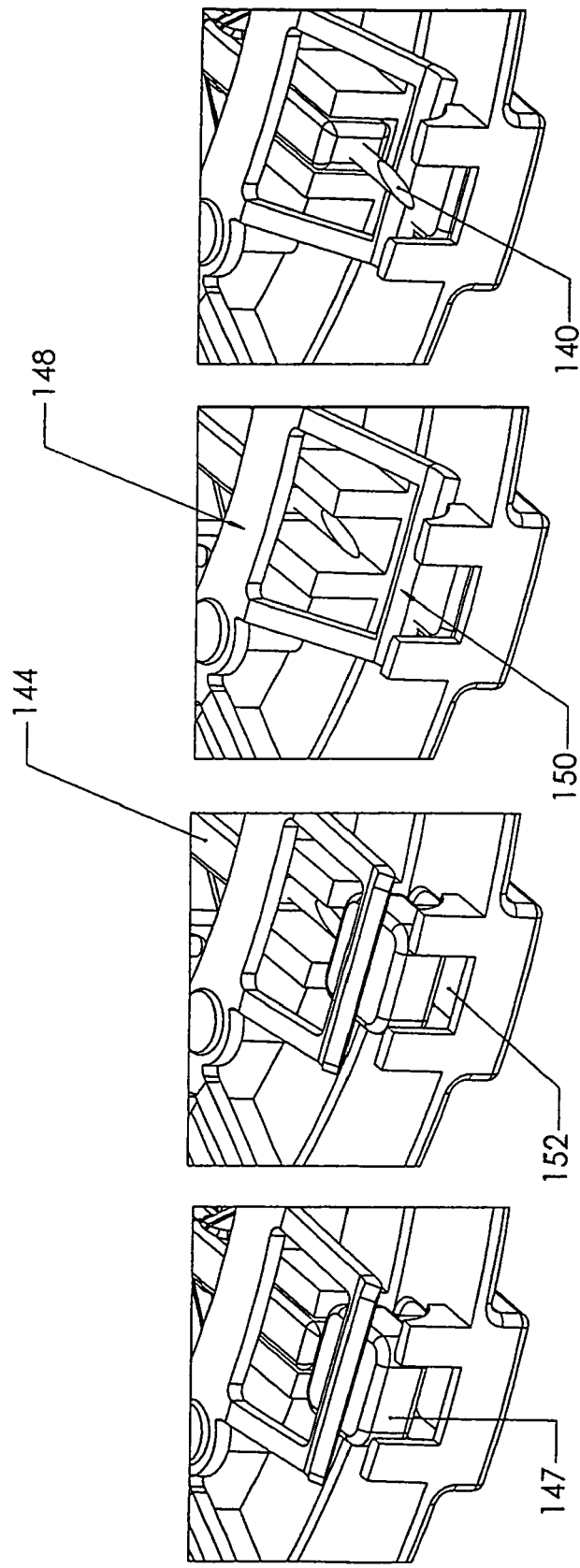

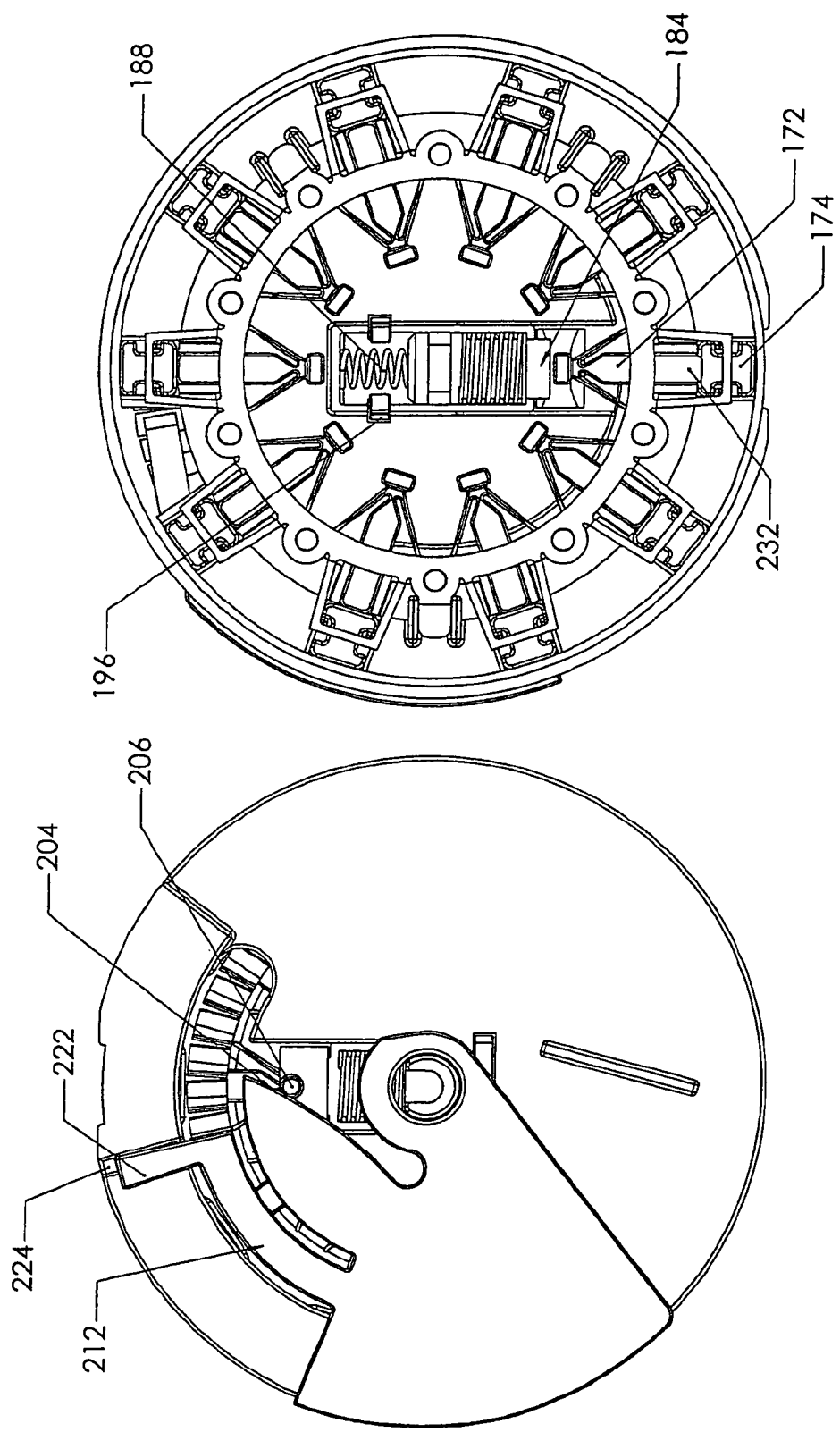

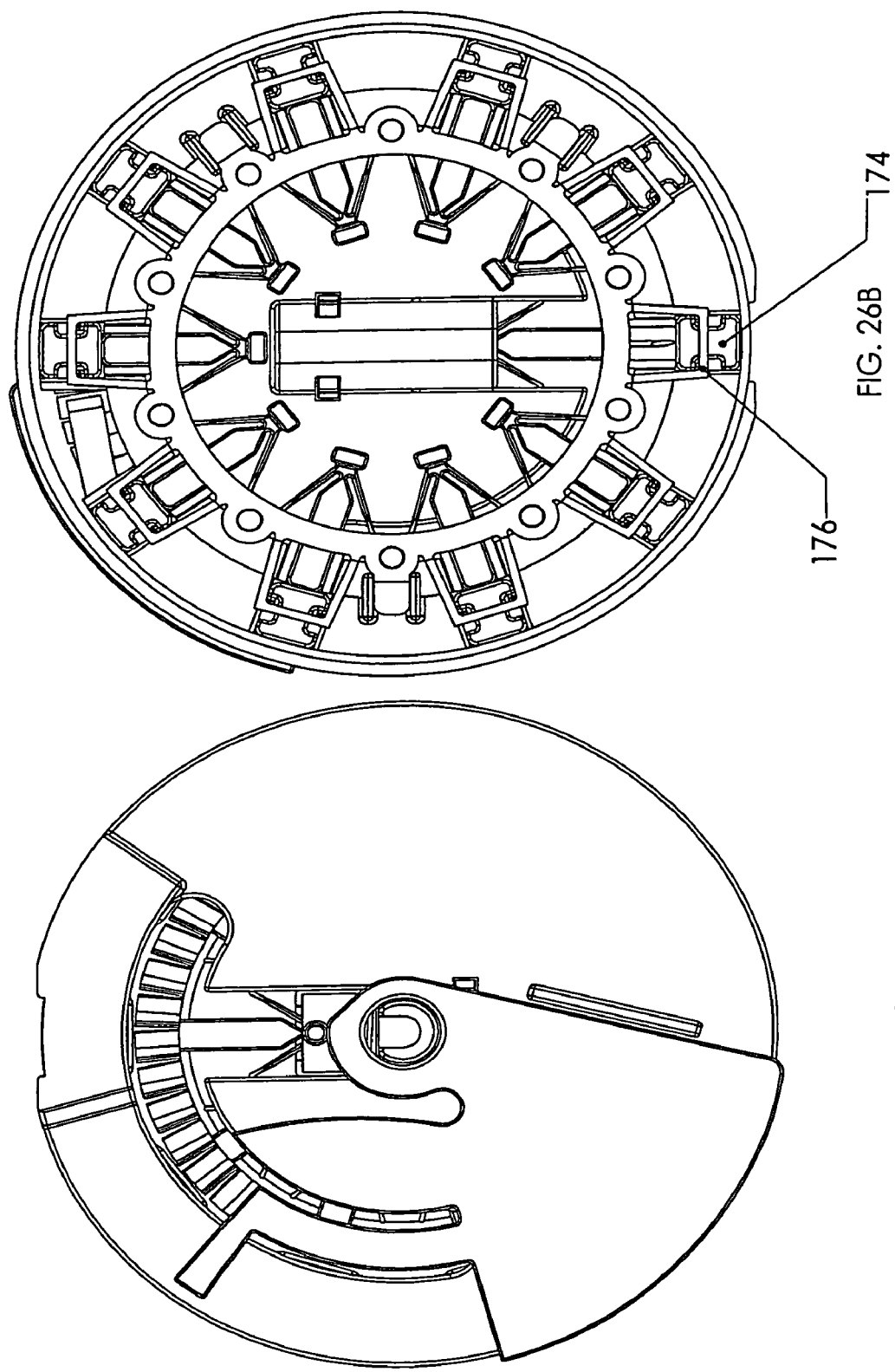

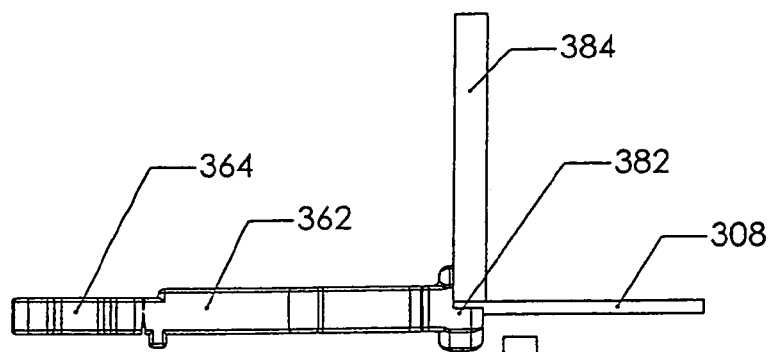
FIG. 39A
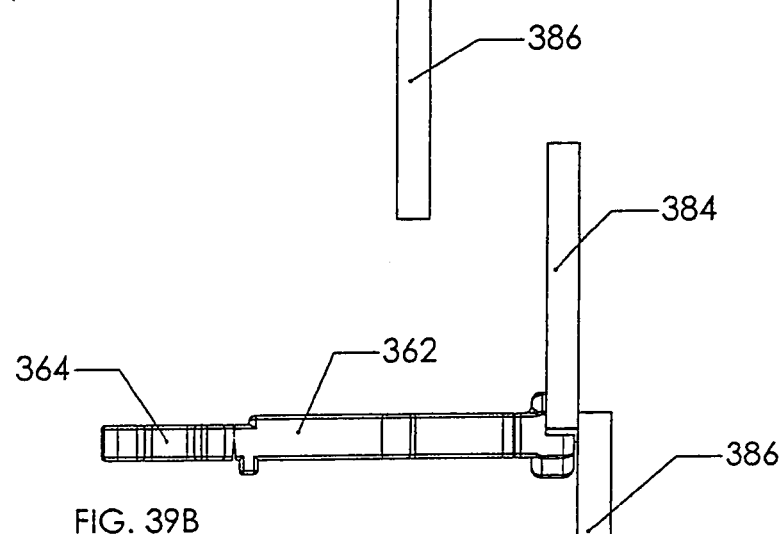
FIG. 39B
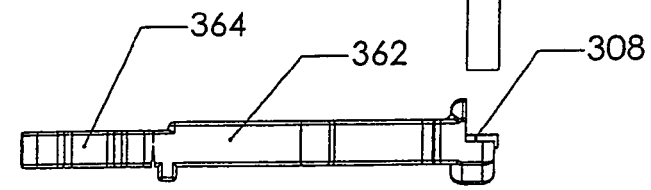
FIG. 39C
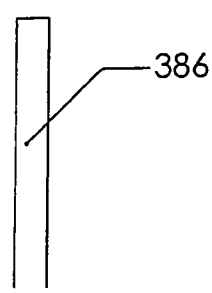

BLOOD SAMPLING DEVICE

CROSS-REFERENCE TO RELATED APPLICATIONS

This application claims the benefit of priority to German Patent Application, Serial No. DE 10208575.7, filed 21 Feb. 2002, German Patent Application, Serial No. DE 10245721.2, filed 24 Sep. 2002, and German Utility Model No. DE 20213607.8, filed 21 Feb. 2002, the content of which are hereby incorporated herein by reference in their entireties.

FIELD OF THE INVENTION

The present invention relates generally to a medical sampling device, and more particularly to a multiple use device for minimally-invasive sampling of blood and/or other body fluids for detection and analysis.

BACKGROUND OF THE INVENTION

Various devices are known for sampling blood and other body fluids for analysis of the condition of a human or other animal. For example, U.S. Pat. No. 5,971,941 is understood to show a cassette with test strips for placement by a slider. A lancet pierces the skin surface so that blood can be obtained for analysis. The lancets are integrated on a test strip, and are positioned together with the test strip. Another embodiment is understood to show a disposable cylindrical insert having a lancet and a test membrane with an aperture for the lancet. The insert is inserted in a mounting cavity of a plunger or piston, which forces the lancet outward for blood withdrawal. DE 198 19 407 A1 is understood to show a multiplicity of test strips with integrated lancets for insertion into an analysis device.

U.S. Pat. No. 4,787,398 is understood to show a device with a plunger for directing a lancet outward, and has an evaluation system and a display system. A replaceable unit is applied to the device for each measurement. The replaceable unit comprises the lancet and a test strip, which is wetted with blood. This replaceable unit is thrown away after each use. EP 0 449 525 A1 is understood to show a blood withdrawal system wherein a new lancet is inserted manually into a release device before each use. A test strip is then inserted into the device. U.S. Pat. No. 4,627,445 is understood to show a device for measuring blood sugar, with an integrated blood withdrawal unit. A new replaceable lancet and test elements must be installed to the device for testing, and afterward disassembled. U.S. Pat. No. 5,951,492 is understood to show a disposable unit with a capillary tube and a test strip, to which sampled blood taken is applied. The capillary tube includes a lancet. A new disposable unit is attached and removed before and after each measurement.

EP 0 877 250 A2, EP 0 949 506 A2 and EP 811 843 A2 are understood to show devices having a multiplicity of test elements arranged on a rotatable disk carrier. The test elements are brought successively into a working position and pushed out of the housing to be wetted with blood. U.S. Pat. No. 6,228,100 U.S. Pat. No. 4,794,926, are understood to show lancets arranged on a carrier, which is rotated with respect to a housing.

German Application DE 100 57 832 C1 is understood to show a lancing device of a known form. Other lancing devices with multiple lancets are understood to be shown, for example, in U.S. patent application Serial No. 2002/0087056 A1 and WO 02/36010 A1. EP 0 589 186 B1 is understood to show a lancet with a removable protective cap. WO 01/66010 A1 is understood to include a multiplicity of lancets in a magazine, with an opening of the chamber closed by an elastic material, which is penetrated in the puncture process.

Known sampling devices have, however, not proven fully satisfactory to all users for a variety of reasons. Accordingly, it is to the provision of an improved sampling device that the present invention is primarily directed.

SUMMARY OF THE INVENTION

Briefly described, the present invention provides an improved sampling device, which is described herein by way of example embodiments representative of the various aspects of the invention. In one aspect, the invention is a lancing device having a plurality of penetration elements or lancets arranged for sequential use in piercing the skin or other tissue of a human or animal subject for obtaining a sample of blood, interstitial fluid, and/or other body fluid(s). In further embodiments, the invention optionally includes collection and/or analysis features for collecting a sample of body fluid and/or analyzing one or more analytes or other characteristics of the sampled fluid. Certain embodiments are compact in size for convenience in portable personal use, for example taking the form of a typical wristwatch. Minimally invasive collection and analysis of sample volumes of less than about 20 µl, and more preferably less than about 10 µl, and most preferably less than about 5 µl, are enabled by example embodiments of the invention.

Example embodiments of the lancing device preferably include a housing and a multiplicity of lancets, with the multiplicity of lancets arranged on a carrier or cassette and insertable, with the cassette, into the housing. A piston or plunger acts on a particular lancet when oriented in its working position. The sharp point of the working lancet is driven into a skin surface of a user positioned over a lancing opening through the housing. The cassette is preferably removable from the housing after use for replacement.

In another aspect, the invention is a cassette comprising a plurality of lancets for penetrating the skin surface or other body portion of a human or animal subject to obtain samples of blood and/or other fluids.

Generally described, one embodiment of the invention is a lancing device having a plurality of penetration elements or lancets for piercing the skin or other tissue of a human or animal subject to obtain a sample of blood or other body fluid(s). In further embodiments, the invention optionally includes collection and/or analysis features for collecting a sample of body fluid and/or analyzing one or more analytes or other characteristics of the sampled fluid. For example, an analyte such as fructosamine, lactate, cholesterol and/or glucose in a subject's blood may be analyzed in a minimally invasive manner by piercing the subject's skin with a lancet, collecting a blood sample on or in a test element, using an evaluation system such as an electronic evaluation system to analyze the sample, and displaying results of the analysis on a display system.

In example embodiments, the invention comprises a single compact device contained within a housing. In the housing, the working position of the lancet corresponds to a puncture position to be applied to the skin surface of a user and, at a different position in the housing, a feeding position designed for feeding a minimal amount of blood exuding from the previously punctured skin surface to a test element. Each of a plurality of test elements and lancets are moved sequentially into a working position in the device to carry out multiple sampling operations. When a lancet is positioned in its working position, the lancet is driven into the skin surface of a user at the puncture position. Blood exuding from the skin surface is applied to a test element by applying the skin surface to the feed position, which is the working position of the test element.

Various embodiments of the invention provide an "all-in-one" device which is compact, i.e., space-saving, and which is user-friendly and operator-friendly. Used test elements and/or lancets are preferably removed and replaced with unused test elements or lancets in a simple manner. The test element can, for example, be designed in the form of a membrane, which defines a measurement field that is wetted with the sample of blood taken, and which contains test reagents selected for the particular analysis to be performed. The analysis system can operate optically, for example, preferably by reflectometry, or electrochemically, or according to other means of analysis. In example embodiments, the test elements and/or the lancets are arranged into or onto a carrier or cassette, which can be inserted into the sampling device and which can be rotated or otherwise moved with respect to the housing, such that the test elements and/or lancets can be moved into working positions, located adjacent or apart from each other, as for example by rotating the carrier or cassette within the housing. Therefore, both the test elements and the lancets are preferably arranged on a rotatable carrier and can be moved into the working position, as by a rotary movement. A lancet is in its working position if it can be moved out through the puncture position to perform a puncture process. A test elements is in its working position if it can, in that position, be wetted with a sample of blood. The working positions of the lancets and the test elements can be adjacent or remote from one another. For example, the working position of the lancet can be at a 3-o'clock position on the housing and the working position of the test elements at a 6-o'clock position. Alternatively, the working positions for test elements and lancets are located at a single rotary position of the carrier by having the lancets arranged radially and the test elements arranged axially, for example by having the puncture position provided radially on the housing and the feed position provided axially on the housing.

Use of a rotatable carrier-advantageously enables a compact design for the housing, such that used test elements and lancets are moved out of the working positions by rotating their carriers. In that way they come automatically to a disposal position without a need to provide another separate translational process. In further embodiments, lancets and test elements are arranged on the same carrier, so that the lancets and test elements can, for example, be removed as a single manually operable unit from the packaging, and can be inserted into the analysis device in a single procedure. In other embodiments, the device includes lancets only, and serves as a lancing device without sampling and testing capability. In still other embodiments, the device includes test elements only, and serves as a testing device without lancing capability. In still further embodiments, the invention comprises a cassette including a plurality of lancets and/or a plurality of test elements, the cassette adapted for removable replacement within a device housing.

In alternate embodiments, the carrier has a first carrier part for the test elements and a second carrier part for the lancets, which can be assembled into a unit that can be inserted as a whole into the device and removed again after use. In other embodiments, test elements on a first carrier part and lancets on a separate second carrier part are separately inserted into the device, in two separate insertion steps by the user. If different carrier parts are provided for the test elements and the lancets, it is preferably that the two carrier parts can be engaged so that they cannot rotate relative to one another, so that a single drive manipulates both carriers. Alternatively, two separate drive systems are provided in the analysis device.

According to one preferred embodiment of the invention, the carrier, or the carrier part, or one of the carrier parts, has a central depression within which a drive means for the blood withdrawal device is provided. Preferably, the carrier, or the carrier parts, or one of the carrier parts, is in the form of a ring and is arranged so that it can rotate about an axis at the center of the ring. The drive for the carrier or the carrier is preferably of compact construction. For example, the drive mechanism can comprise an electric motor, or a mechanical drive such as a lever or slide mechanism. The carrier or the carrier parts preferably have discrete rotational stop positions, for example by including a catch, step, or stop, or by suitable design of the drive means. It has been found advantageous, resulting in a relatively compact structure, for the carrier or the carrier parts to define a central depression which also encloses a drive means to rotate the carrier or the carrier parts, for example, by way of one or more internal gears with which a driving gear meshes.

The invention also includes embodiments wherein lancets are arranged on a carrier or cassette so that in their working position they carry out a puncture movement in the radial direction with respect to the ratability of the carrier, but also those embodiments in which the lancets carry out a puncture movement in the axial direction. The lancets are arranged on the carrier in various ways in the different embodiments of the invention. According to one embodiment, a lancet is held by a piston, which moves in a cylindrical channel formed in the cartridge or cassette. The lancet is preferably a plastic injection-molded piece engaged by the piston.

The lancet is preferably surrounded by a sterility barrier before a puncture process is performed on the subject. In the above-described embodiment, the sterility barrier is formed by the cartridge on one side and by the piston on the other. The end of the cartridge directed away from the piston is preferably covered by a specially sealed film. In order to make also a seal that will meet the requirements between the piston and the wall of the cylindrical space, another sealing means is provided there. This can, for example, comprise a connection between the wall and the piston means, which is overcome when the puncture process is performed. It would also be possible to use a sealing compound there, or, for instance, it would be possible to provide annular protuberances and steps, shoulders or depressions which interact with them in the other part. Several cartridges are preferably sealed together in the form of a ribbon, and the ends of the ribbon are connected together in circular, ring-like fashion. Cartridges can be produced as endless ribbons, divided into segments, and the segments' ends joined to form a ring-like cassette. Alternatively, the cartridge is arranged in the form of a ribbon forming only along an arc of a circle, or in a generally straight belt.

According to another embodiment, the carrier comprises a plurality of depressions, within each of which is mounted a lancet. The lancets are preferably arranged in the axial direction with respect to the rotatability of the carrier. At least a portion of one of the walls bordering a depression is preferably deformable, so that the lancet can be deflected outward by a drive means to carry out the lancing process. To increase the deformability, zones of weakness are preferably also designed into the wall bordering the depression. The depression is preferably essentially dome-shaped, in the shape of a concave clamshell. A sterility barrier is preferably provided, comprising a film-like cover sealed over the depression, encapsulating the lancet tip. The cover is removed before lancing, or alternatively is sufficiently thin so as to be penetrated by the lancet during lancing.

In still another embodiment of the invention, the lancets have removable caps at their free ends for protection against accidental sticks and to preserve sterility. The lancet can be forced through the protective capping means. It would also be considered advantageous, though, if the protective capping means can be removed from the particular lancet immediately before performing the puncture process. That can be accomplished in an advantageous manner by drawing back a particular lancet slightly immediately before performing the puncture process, with the protective capping means prevented by a stop or the like from moving along with the lancet. Then it proves advantageous if the particular protective capping means can be removed from the path of movement of the lancet after it has been removed from the particular lancet, and can be moved to a holding space. For that purpose, one could, for example, use gravity or a spring.

The arrangement of test elements on the carrier can also be such that the test elements are oriented axially with respect to the rotatability of the carrier, or such that they are oriented radially. In preferred embodiments, the test elements are oriented axially, such that the application position for a skin surface, usually a finger of a user, is usually oriented in the axial direction, if not, capillary liquid paths are arranged in an intermediate position between the application position and the test elements in its operating position. For an axial direction or orientation of the test elements with its measurement field, which is generally planar or spread over an area, it proves advantageous if the test element is provided on a disk-shaped, especially a ring-shaped carrier part, the plane of which is oriented perpendicularly to the axis of rotation of the carrier and which preferably coincides with a plane of the particular test elements.

According to another embodiment of the invention, it proves advantageous for the application position on the housing body to be covered by a movable cover part when it is not needed, which can be opened up if an analysis is to be done. In another embodiment, moving the cover part in the direction to open up the application position activates a drive means of the blood withdrawal device; that is, if it produces an initiating pressure or generates a voltage, or even turns on an electric motor. In other embodiments, the drive means of the blood withdrawal device is activated by tensioning a spring.

According to a further embodiment of the invention, the blood withdrawal device has a manually movable control element which is coupled with the drive means for the lancet and with the rotatable carrier so that moving the lancet into the working position results in activation of the drive means for the lancet and rotation of the carrier. This manually movable control element can, for instance, be in the form of a wheel, a slide, or, in a preferred manner, be made from the previously mentioned cover part. The coupling between the control element and the drive means or carrier can be designed such that activation of the drive means and rotation of the carrier occur simultaneously. Alternatively, one event occurs after the other. In particular, coupling the control element and the drive means or carrier provides for a first phase of movement in a first positioning direction resulting in rotation of the carrier while a second phase of movement, for example in the opposite direction to the first positioning direction, results in activating the drive means.

To achieve stepwise further rotation of the carrier, it is advantageous to bring the control element into a driving connection with the carrier in a first positioning direction, and, during a second phase of movement opposite to the positioning direction, i.e., returning the control element to its initial position, to separate the control element from its driving connection. It is further advantageous if this return movement of the control element sets the drive means for the lancet back into its initial or resting position. It is also advantageous for the initiating means to be placed at a position of the housing at which it can be actuated well ergonomically.

In example embodiments, the coupling between the control element and carrier is accomplished advantageously by a gear drive. For instance, a translational or even a pivoting movement is converted through a tooth-like intermediate means into rotational movement in a simple manner. The rotational movement can then be utilized easily to drive the carrier. Alternatively, the coupling between the control element and carrier is accomplished in a different manner, such as by an intermediate means in the form of an arrangement of notches.

In example embodiments, the drive means for the lancet comprises a spring, preferably in the form of a leaf spring or coil spring, which is tensioned and then released to generate the lancing action. To tension the spring, the control element can act on a holder for the spring, for example through a gear drive, pivoting this holder in the plane of bending of the spring, or to compress or tension the spring, thereby activating the drive means for the lancet. Preferably the spring is moved past a dead point to a stable tensioned position so that the drive means automatically remains in the activated state. Then no releasable catch mechanism is required.

According to another embodiment, an initiating means for the drive means of the lancet is actuated by applying a skin surface to the puncture position. The initiating means can be, for example, a contact sensor or a button that can be pressed in. In further embodiments, the initiating means is placed at a position on the housing that can be actuated easily and ergonomically, for example on the side essentially opposite the puncture position. A further embodiment positions the initiating means in the puncture position and is actuated by application of the skin surface to be punctured against the device. In this respect, an embodiment in which the initiating means has a cutout for passage of the lancet to carry out the puncture process is preferred.

A further embodiment provides a retraction mechanism that withdraws a particular lancet immediately after the puncture process, so that the skin surface of a user is penetrated for only a very brief time. The retraction mechanism can comprise for example, a spring that exerts a withdrawal force on the lancet after lancing the skin. For instance, a lancet can penetrate through a spiral or strap-shaped spring such that this spring is tensioned when the puncture process is carried out. In other embodiments, the retraction mechanism is provided in the drive means of the blood withdrawal device, such as by a restraint or by a motor-driven forward and back movement of a drive means coupled to the lancet. For instance, if the lancet is held at a piston, a retraction mechanism can be produced by incorporating a spring into the piston. The retraction mechanism may also be provided by an elastically deformable wall region that directly holds the lancet.

In preferred embodiments, the blood withdrawal device of the present invention comprises a housing that is essentially circular, or has a generally circular outer contour. For example, the housing may be sized and shaped generally like a typical watch case, in particular like a wristwatch case, and also comprises a time indication display. In such cases, the housing is optionally worn by the user by means of a watch band, which is fastened about the wearer's wrist.

In another embodiment, the invention is a lancing device having at least one lancet with a protective cap that is automatically removed upon actuation of the device. A lancet is at least partially contained in a holder and the end section of the lancet, which forms the sharp lancing tip, is surrounded by a removable protective capping means for sterility and for protection against accidental sticks. The longitudinal dimension of the lancet, with holder and protective capping means, is preferably ≦15 mm in the direction of lancet travel. The protective capping means is removed from the lancet and moved out of the path of movement of the lancet, preferably transversely to the direction of puncturing, before performance of the puncturing process, by means of a displacing means.

The lancet is preferably relatively small in the dimension along its path of lancing travel, for example not greater than about 15 mm; not greater than about 14 mm in a preferred embodiment; and, in a particularly preferred embodiment not more than about 13 mm, because a particular lancet is held in a holder which can, in particular, be an injection-molded plastic part. The longitudinal dimension includes the holder and the protective capping means. The protective capping means is preferably removed from the path of movement of the lancet inside the lancing device immediately before a puncture process is carried out. For instance, the protective capping means in question is initially be pulled off the lancet in the direction of puncturing, so that it is released from the free end of the lancet, and is then moved sideways, preferably perpendicularly to the direction of puncture, automatically by means of a displacement means so that the puncture process can be carried out. Alternatively, a particular protective capping means initially remains in its position while the lancet is pulled slightly back, opposite to the direction of puncturing, so that the free end of the lancet is released from the protective capping means.

The protective capping means may be placed on the free pointed end of a lancet independently of the production of the holder. Alternatively, the protective capping means is injection-molded onto the lancet, preferably in the same process together with the holder. In such case the protective capping means continues into the holder as a single piece over a segment that forms a weakened area or a predetermined breaking point. This generally simplifies the manipulation of the lancet in direct connection with its production.

The segment forming the weakened area or predetermined breaking point may be separated by twisting or turning to remove the protective capping means. Alternatively the segment forming the weakened area or predetermined breaking point is separated under tensile stress in the longitudinal direction of the particular lancet, i.e., in the direction of puncturing. The protective capping means can be pulled off of the lancet in the direction of puncture by a displacement means, such as a plunger-like or cartridge-like displacement means. Or, as mentioned initially, the lancet is pulled back opposite to the direction of puncturing and so released from the protective capping means. According to one particularly preferred embodiment of the invention, the protective capping means is removable from the lancet when the plunger system is tensioned. Therefore a movement to remove the protective capping means is carried out when the plunger system is tensioned. In particular, in that process, the lancet is pulled back opposite to the direction of puncturing.

According to another embodiment, the holder for the lancet holds the lancet, and also serves a guiding function during the puncturing process. The external shape of the holder is preferably designed so as to be complementary to guide means, such as in the form of guide walls, for the arrangement of the lancet so that it can be moved by sliding along a path. In a further embodiment, the holder has at least one retaining means for fixing the holder in position, for example in the form of a pin extending downward. Such a pin keeps the holder, and therefore the lancet, in a position in the plane of the holder, thus preventing rotation of the lancet about its longitudinal axis, particularly during the puncture process, and also preventing the lancet from sliding out when a lancet carrier or cassette is being replaced in the housing. A particular holder can, however, optionally also have a pin which can be spread out in an elastically resilient manner, which can exert a withdrawing force on the lancet, so that the holder with all the lancets is pulled back again behind an application area on the housing body.

To carry out the puncture process, example embodiments include a plunger system with a spring which can be pretensioned, and which strikes an end of the holder or of a particular lancet in the direction of puncturing, moving it in the direction of puncturing as by a blow. In other embodiments, the holder has a rear gripping means that interacts with the puncture means. A particular holder is coupled with the puncture means through this rear gripping means and is moved into an activated position upon tensioning of the puncture means. In order for the protective capping means to be moved reliably and quickly, especially transversely across the path of movement, it is preferably pretensioned, particularly transversely to the path of movement of the lancet. The pretensioned displacement means is preferably in direct or indirect contact with the protective capping means. To avoid relative movement between the protective capping means and the displacement means, each protective capping means is preferably permanently assigned to a corresponding displacement means, i.e., even outside of the particular operating position.

After separation of the protective capping means, the path of movement of the lancet is preferably clear. In example forms, the displacement means comprises a resilient loop, for example having a generally U-shape, which forces the protective capping means out of the path of movement of the lancet upon separation of the capping means from the lancet. Because of the loop design, the displacement means can be in contact with the protective capping means even after the displacement process, with the lancet able to move through the opening formed between the legs of the loop. The carrier preferably comprises disposal chambers or positions for receiving the protective capping means after separation from the lancet. For example, one or more holding cavities are preferably formed into the carrier for receiving the protective capping means after separation from the lancet.

In further embodiments, the removed protective capping means is held in a clamped position in its disposal position so that it does not rattle about during use of the device. For example, removed protective caps are preferably held against a wall of the carrier under pretension or load, preferably by pressure applied by the displacement means against the protective capping means. To provide a compact design of the device the protective capping means is preferably pretensioned by the same means in its initial position at the free end of the lancet and in its disposal position, particularly and preferably by the displacement means. The displacement means is preferably mounted on the carrier so that it can be inserted with the carrier into the housing. In a further preferred embodiment, the displacement means is provided on the carrier such that it holds the lancets with its holders and the protective capping means so that they cannot be lost, but at the same time holds them on the carrier so that they can slide. For example, the displacement means preferably comprise a spring element that applies a force against the protective capping means. When the carrier for the lancets is rotatable, the displacement means is preferably a ring-shaped spring with spring tongues projecting radially from it.

In preferred forms, the puncturing means comprises a plunger system having a piston means or a plunger means, which is placed under tension, for carrying out the puncture process. The plunger means may contact the free end of the holder or lancet to accelerate it by a blow. Alternatively, the plunger means of the plunger system is connected to the holder before the plunger process is carried out. For that purpose, the plunger means preferably has a coupling region which can be coupled to the holder for the lancet so that the plunger means and lancet are engaged before the lancing process is carried out, and thus particularly so that the plunger means can carry out a tensioning movement together with the holder.

The coupling in which the plunger means and the holder or the lancet fit together can be achieved by any suitable clamping means, catching loop, or similar removable connection. In a further embodiment of the invention, though, the coupling region of the plunger means and the holder are coupled together because they can be moved in relation to each other, transversely to the direction of puncture, into a position in which they fit together and lock together. In such a case, no flexible claws, catches or clamping means need be used. Particularly with a concentrically rotatable arrangement with a radially directed lancet, the holder and the coupling region of the plunger means can be rotatably engaged in the peripheral direction of the rotatable arrangement.

So that the plunger means can tension the puncture system against a tensioning force, the puncture means preferably includes a tensioning cam transverse to the direction of puncture. In this manner, the tensioning cam allows movement of the tensioning mechanism for the plunger means in a parallel plane. Then the tensioning cam is advantageously directed along a curved path of an adjustable or actuatable tensioning means. During this movement of the tensioning cam along the curved path, the linear plunger means, which is necessarily carried along with it, is brought into a tensioned activated state. The curved path mentioned can, in any arbitrary actual form, advantageously be a crank path or a cam guide path.

It further proves advantageous if the tensioning means is withdrawn under control of spring force after carrying out the movement in the tensioning direction. Here, for example, a lever is provided which is pivoted or mounted so that it can rotate, in a disk shape, the movement of which in the direction of tensioning tensions a withdrawal spring. For example, the tensioning means preferably comprises a lever projecting outwardly of the housing of the puncture means, which is then moved manually in the tensioning direction, and which, when released, moves automatically back into its initial position.

The tensioning means for tensioning or activating the plunger system preferably simultaneously forms a positioning means for moving a lancet into an operating position and moving a used lancet to a disposal position. Therefore the carrier with the lancet is preferably moved on by a step, particularly rotated farther. In place of further movement of the carrier, a further positioning of the plunger system relative to the carrier is preferably carried out. Accordingly, one and the same positioning movement activates the plunger-system and also moves a new and unused lancet, or the plunger system, to an operating position.

The tensioning means or the tensioning mechanism is preferably arranged so that in a first phase of movement it is in a driving connection with the carrier for the lancets and, in a second phase of movement, it is in a driving connection with the plunger means. In such a case, the driving connection between the tensioning means and the carrier is separated at the end of the first phase of movement by the tensioning means, or an arm of the tensioning means, sliding against a ramp means. Even though actuation is by the same tensioning means, this accomplishes, by further movement of the carrier in the first phase, movement of a new lancet into the operating position and its coupling with the plunger means; and then in the second phase of the movement the plunger means, particularly with the lancet coupled with it, is moved in the direction of tensioning.

The lancing device of the present invention enables a method of withdrawal and collection of a minimal amount of blood or other body fluid from a human or animal subject. Optionally, the lancing device further comprises at least one test element, enabling evaluation and display of a characteristic or analyte of the sampled fluid, for example serving as a blood analysis device which can be handled as a single "all in one" device. In such a case, the test elements are preferably movable in succession into an operating position in which the required minimal amount of blood from a previously punctured skin surface of a user can be transferred to the particular test element(s). The test element(s) comprise, for example, membranes containing test reagents, by means of which the analysis can be done optically, electrochemically or electrophysically in a known manner. For example, an analyte such as fructosamine, lactate, cholesterol or, especially, glucose, can be determined qualitatively and preferably also quantitatively.

According to an example embodiment of the invention, the lancets and/or the test elements are arranged concentrically about a point of rotation, so that they can be rotated into their individual operating positions. For that purpose, a first carrier for the lancets and a separate second carrier for the test elements are provided. To facilitate miniaturization of the device, the lancets, when arranged radially on the carrier, preferably leave a segment of a circle open so that the carrier can be inserted into the housing such that the plunger system extends into that circular segment. Because no lancet is placed in one circular segment (like a wedge of cake, which can cover for example 10° to 20° in the peripheral direction), the plunger system can penetrate in the radial direction into this region of the circular segment. Thus the plunger system does not hamper insertion of the carrier with the lancets into the housing. This further proves advantageous if, as described initially, a particular lancet and a plunger means of the plunger system are rotated relative to each other into a coupled connection.

In another aspect, the invention is a lancing device including a housing, and a cassette removably mounted within the housing. The cassette preferably includes at least one lancet having a lancet body and a protective cap. The lancing device further includes a piston for propelling the lancet along a path of travel, the piston releasably engaging the lancet and causing separation of the lancet body and the protective cap along at least a portion of the path of travel of the lancet.

In another aspect, the invention is a lancing device including at least one lancet having a sharp tip and a protective cap covering the sharp tip, a spring for driving the at least one lancet from a first position to a second position, and a cocking mechanism for loading the spring and removing the protective cap from the at least one lancet in a single continuous cocking motion.

In still another aspect, the invention is a lancing device including at least one lancet having a protective cap, a piston for engaging the at least one lancet and separating the protective cap from the lancet, and a biasing element for moving the protective cap out of a path of travel of the lancet.

In another aspect, the invention is a lancing device including a plurality of lancets, a biasing element for driving each of the plurality of lancets along a path of travel, and a cocking mechanism for sequentially engaging successive lancets and arming the biasing element.

In yet another aspect, the invention is a lancing device including at least one lancet movable along a path of travel, means for removing a protective cap from the at least one lancet, and biasing means for moving the removed protective cap out of the path of travel of the lancet, wherein the path of travel extends through the biasing means.

In another aspect, the invention is a lancing device with multiple lancets, each lancet having a body with an elongated lancing tip mounted therein, each lancet body having at least one grip flange for cooperation with a cocking mechanism, configured and positioned to apply a tensile force generally coaxial with the axis of the lancing tip.

In another aspect, the invention is a lancing cassette including a plurality of lancets, each lancet comprising a lancet body, a lancet tip extending from one end of the lancet body, and a protective cap covering the sharp lancet tip. The lancing cassette preferably also includes a carrier defining a path of travel for each of the plurality of lancets, and a retainer for retaining each of the plurality of lancets on its defined path of travel.

In still another aspect, the invention is a lancing cassette having at least one lancet with a protective cap mounted thereon, a spring for moving the protective cap away from each lancet, and at least one guide constraining the protective cap along a path of travel under the influence of the spring.

In another aspect, the invention is a lancing cassette including a carrier, a retainer mounted to said carrier, and at least one lancet retained between said carrier and said retainer.

In still another aspect, the invention is a lancing cassette for removable insertion within a lancing device. The cassette preferably includes a plurality of lancets, and a series of engagement teeth for cooperative engagement with an advancing mechanism of the lancing device.

In another aspect, the invention is a lancing cassette including a plurality of lancets mounted to a carrier, each of the plurality of lancets movable along the carrier between a retracted position and an extended position, at least one of the carrier and the lancets having a stop for limiting motion of the lancets beyond at least one of the retracted position and the extended position.

In yet another aspect, the invention is a lancet, preferably small relative to standard, known lancets (sometimes referred to herein as a "micro-lancet"), including a lancet body, a sharp lancet tip extending from a first end of the lancet body, and a protective cap overlying the sharp lancet tip, and defining at least one recess for engagement with an external guide.

In another aspect, the invention is a micro-lancet including a polymeric lancet body having a first end and a second end, and a needle extending through the lancet body and having a sharp tip projecting from the first end of the lancet body. The end of the needle opposite the sharp tip is preferably cut substantially flush with the second end of the lancet body.

In another aspect, the invention is a micro-lancet including a lancet body having a first end and a second end, a needle having a sharp lancing tip projecting from the first end of the lancet body, and a protective cap covering the sharp lancing tip. The protective cap is preferably integrally formed with the lancet body and connected to the lancet body by at least one, and preferably two webs of material spaced on either side of the needle.

In still another aspect, the invention is a micro-lancet including a lancet body having a first end and a second end, a sharp lancing tip projecting from the first end of the lancet body, and a flange projecting transversely outward from the second end of the lancet body.

In another aspect, the invention is a lancing device including a plurality of lancets and a drive mechanism for sequentially engaging each of the lancets and driving that lancet between a first position and a second position along an axis of translation, wherein the drive mechanism includes a piston movable along an axis that is coaxial with the axis of translation of the driven lancet.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWING FIGURES

FIG. 6 is a view along a sectional plane through arrows B-B of FIG. 2.

FIGS. 15 and 16 show a cassette of lancets according to yet another embodiment of the invention.

FIGS. 17a-d show a sequence of operation of removal of a protective cap from a lancet, according to an example embodiment of the invention.

Figure 18:
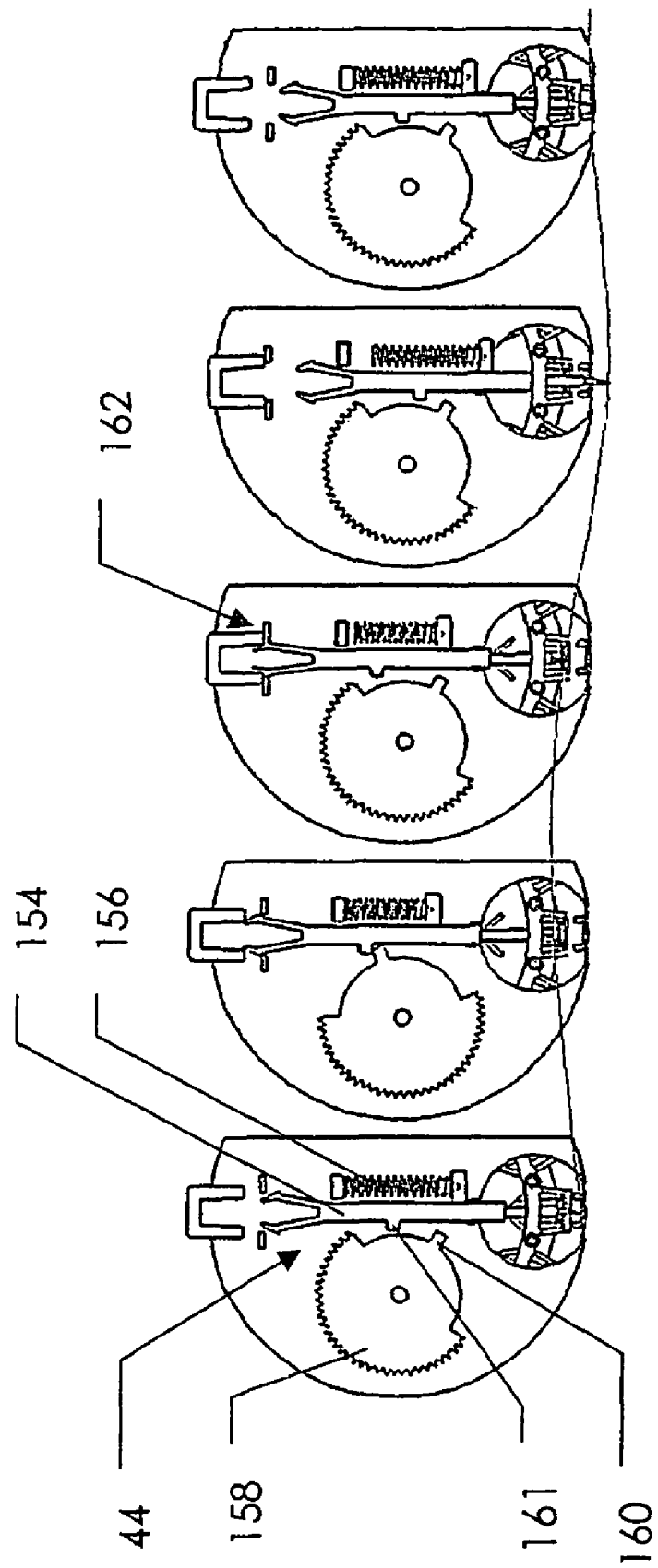

FIG. 18 shows an activation and release mechanism portion of a sampling device according to an example embodiment of the invention.

Figure 19:
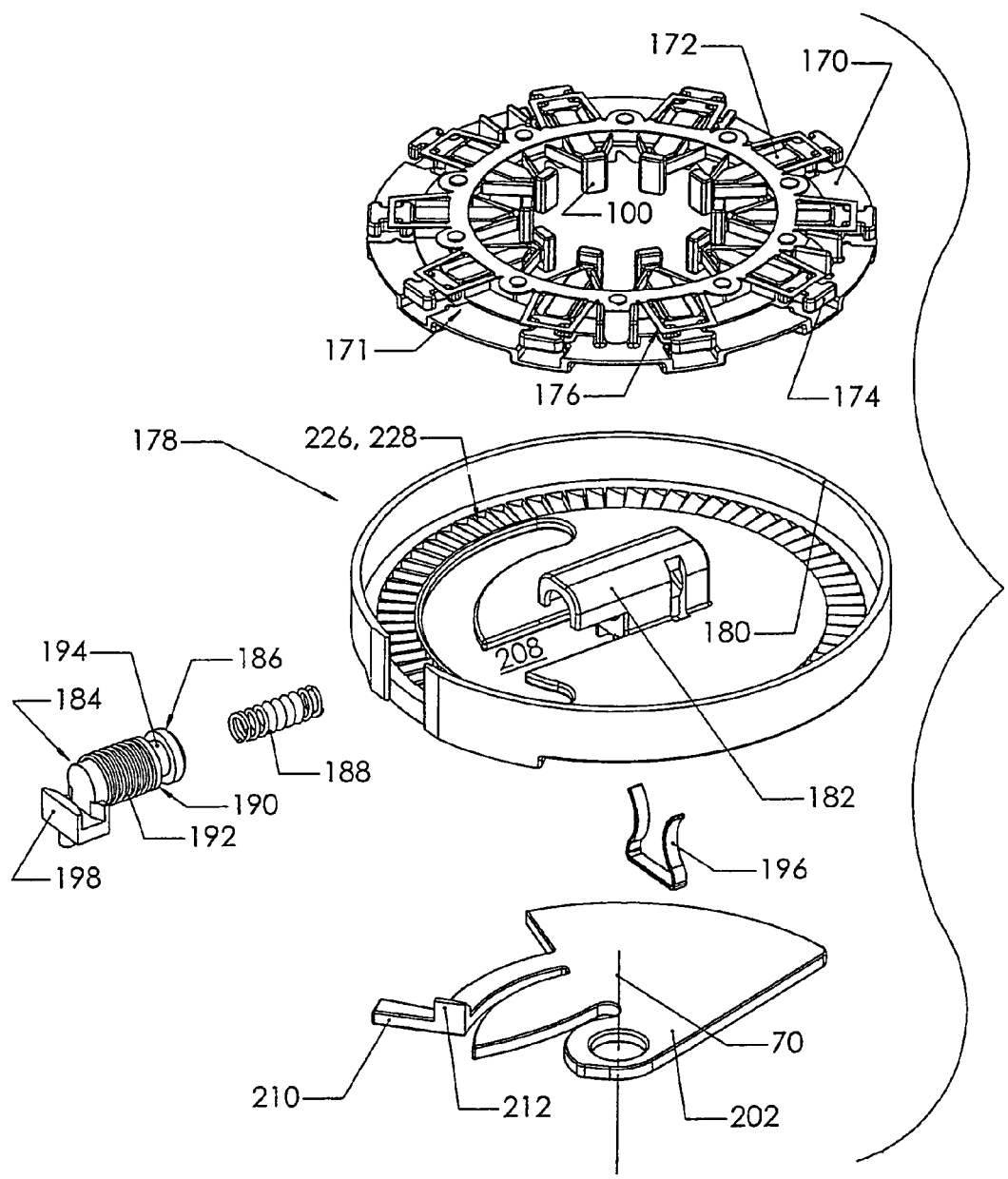
Figure 20:
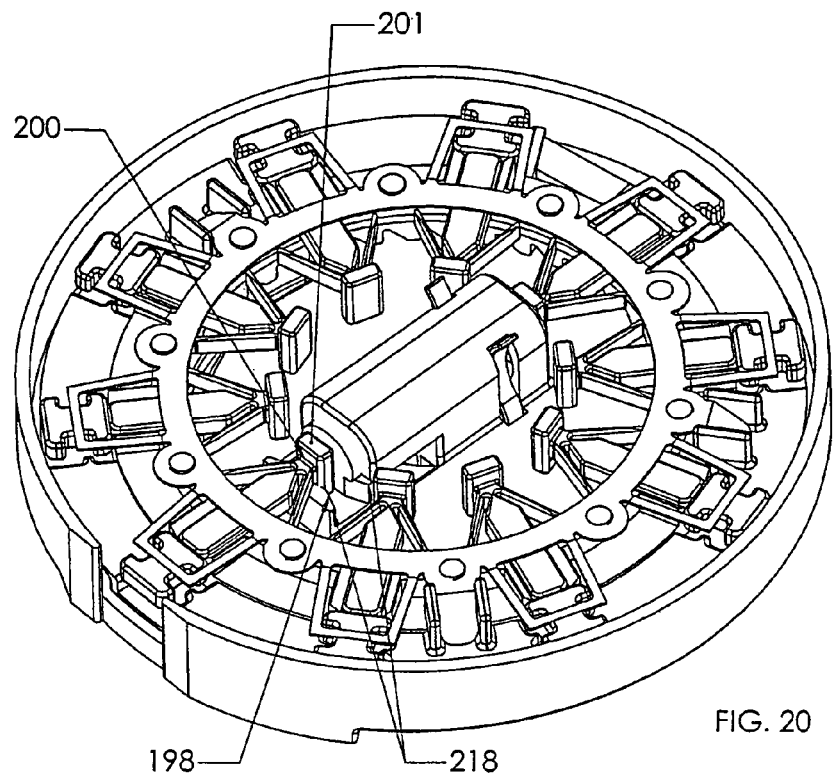
Figure 21:
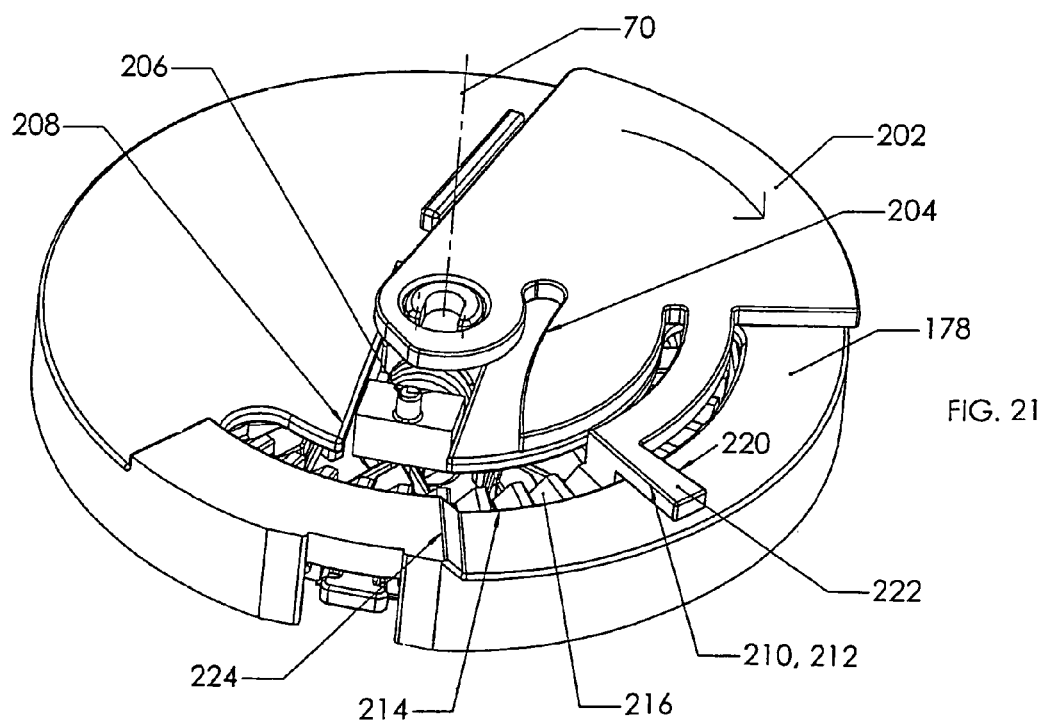

FIGS. 19-21 show an exploded representation and top and bottom views of a sampling device and lancets according to an embodiment of the present invention.

FIGS. 22-28 show a sequence of operation of an actuation cycle of the sampling device of FIGS. 19-21.

Figure 29:
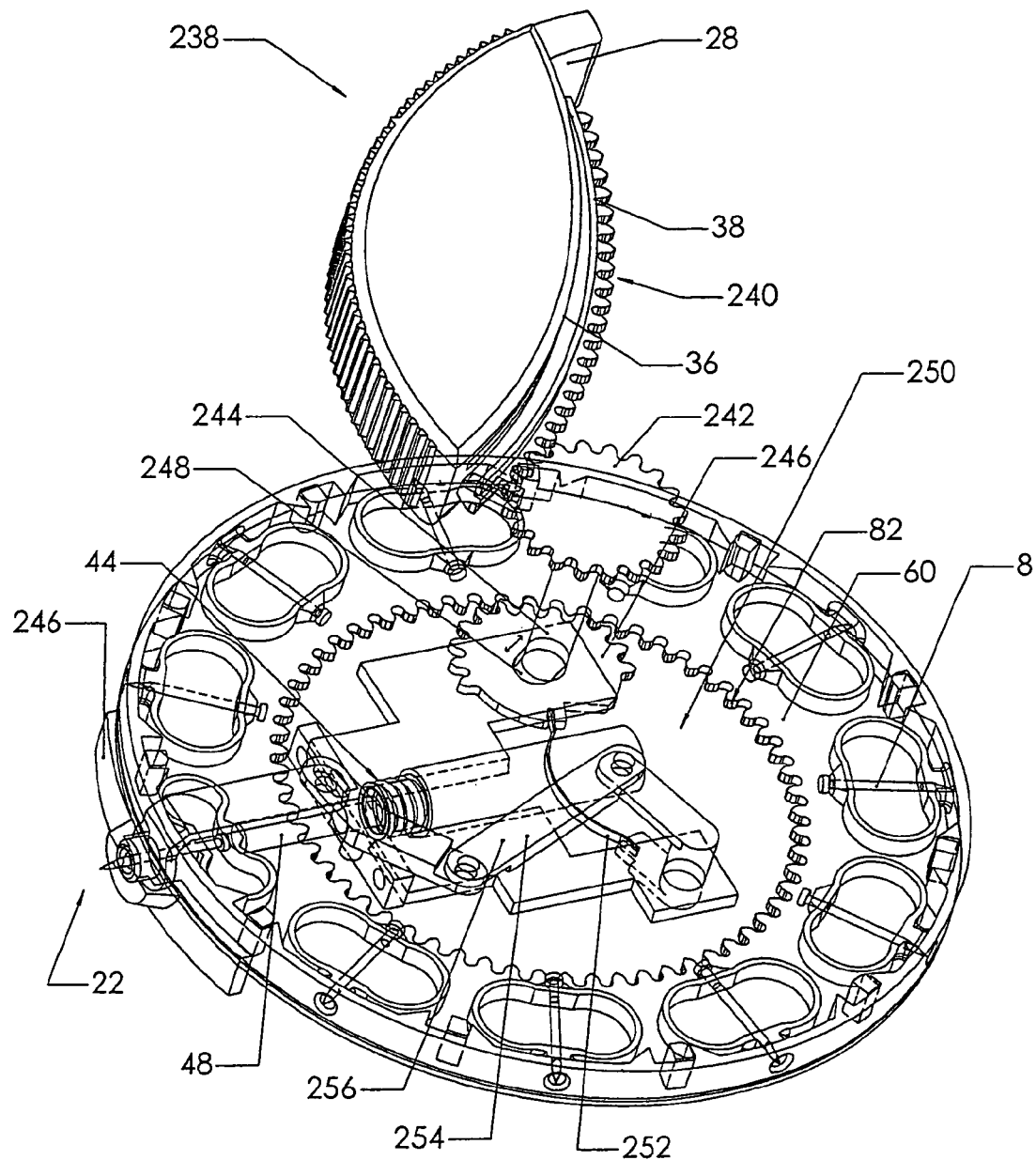

FIG. 29 shows a partial internal view of a sampling device according to another embodiment of the invention.

Figure 30A:
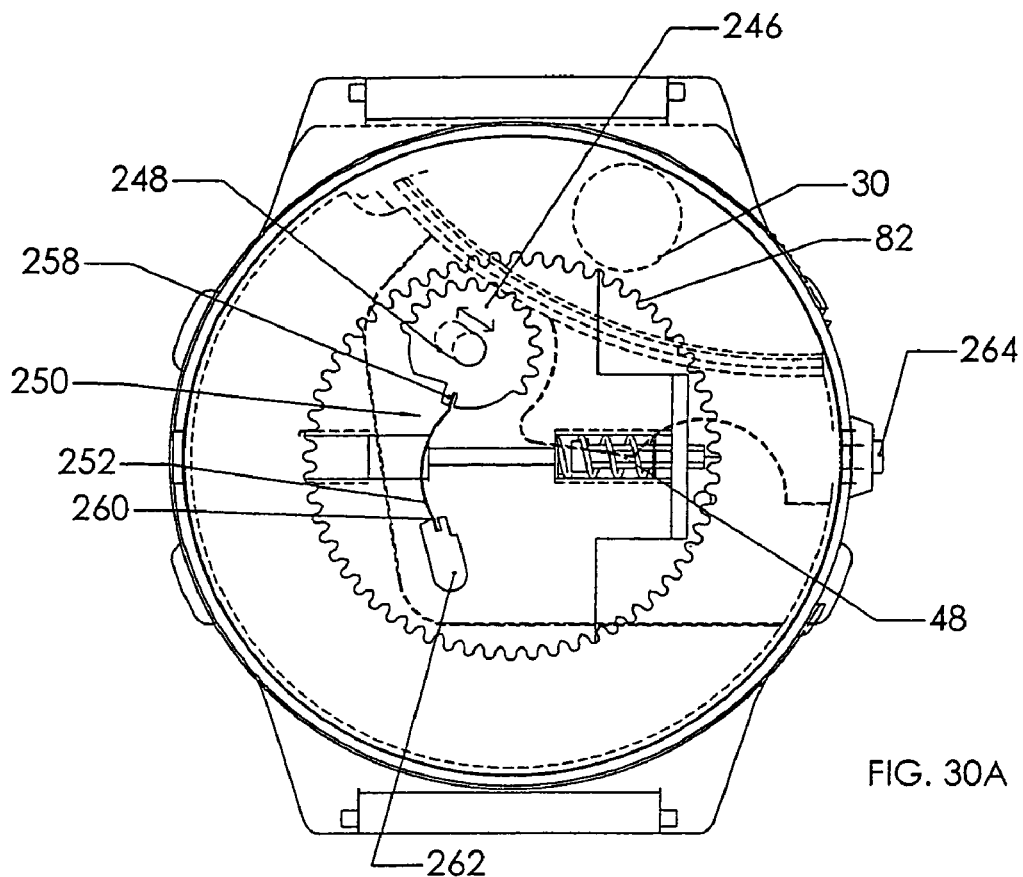
Figure 30B:
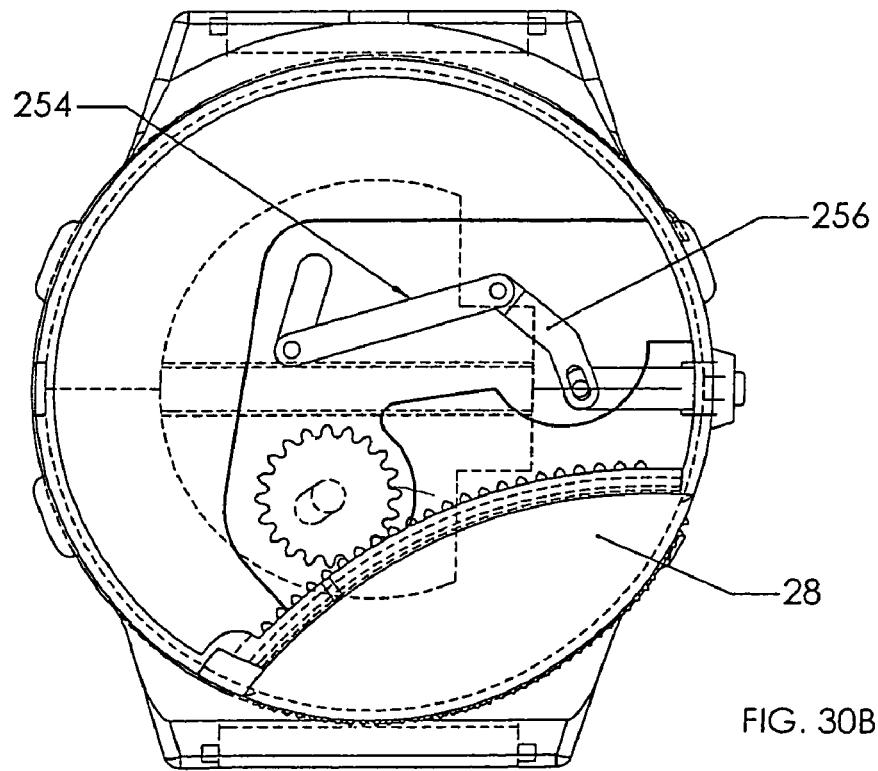
Figure 31A:
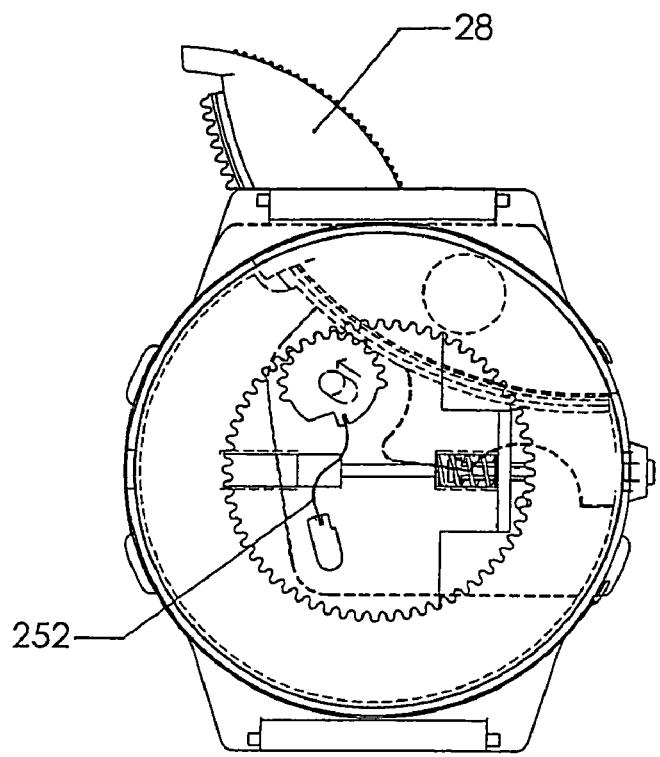
Figure 31B:
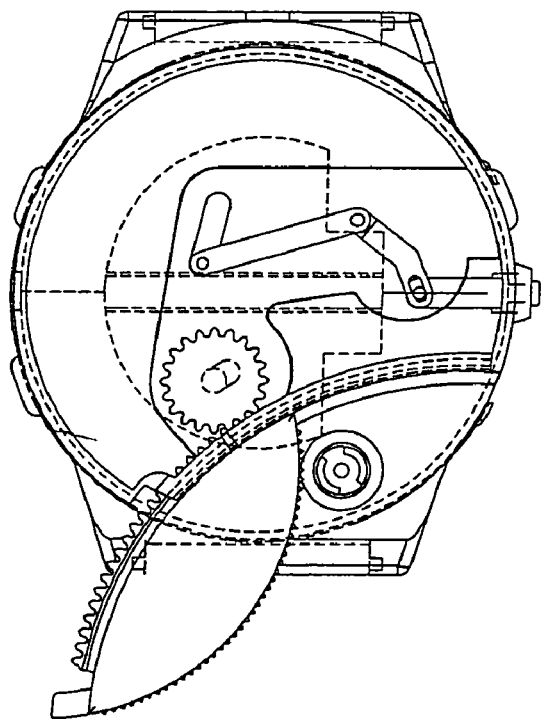
Figure 32A:
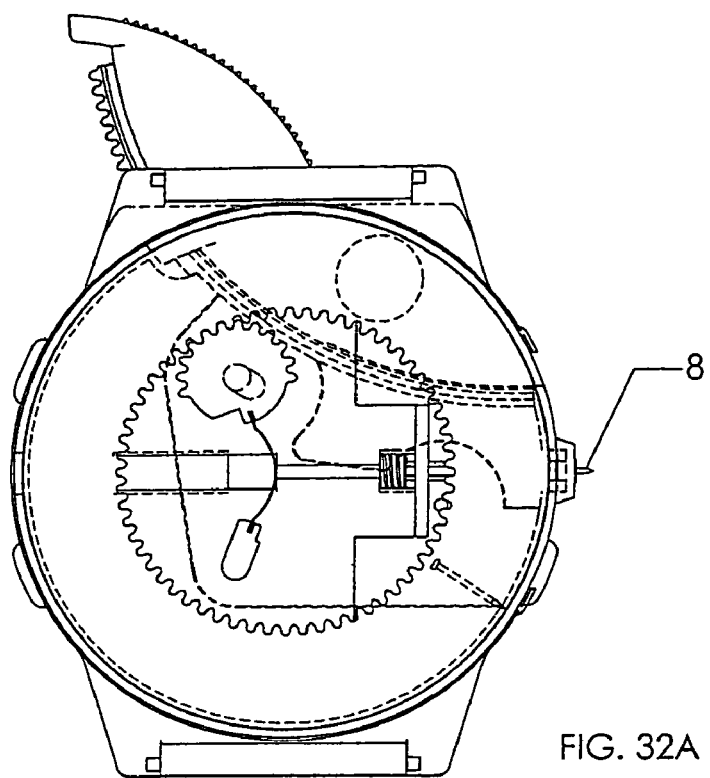
Figure 32B:
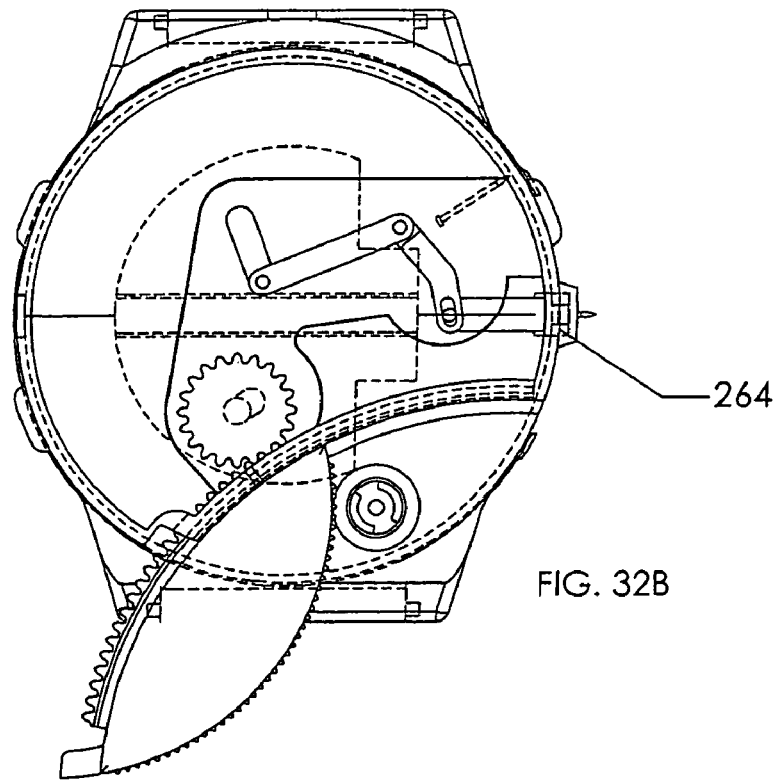

FIGS. 30-32 show a sequence of operation of the device of FIG. 29.

Figure 33:
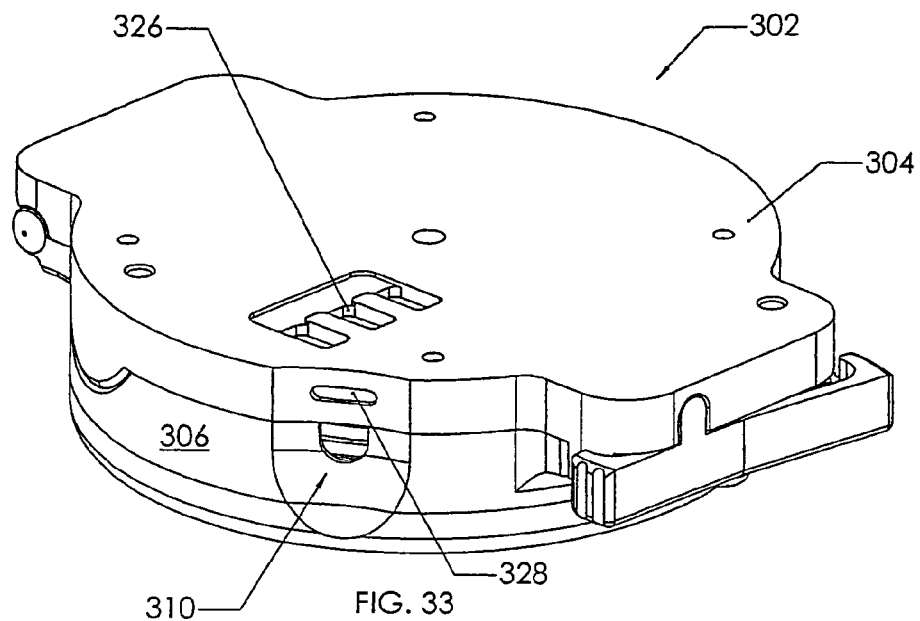

FIG. 33 shows a perspective view of another embodiment of the sampling device of the present invention.

Figure 34:
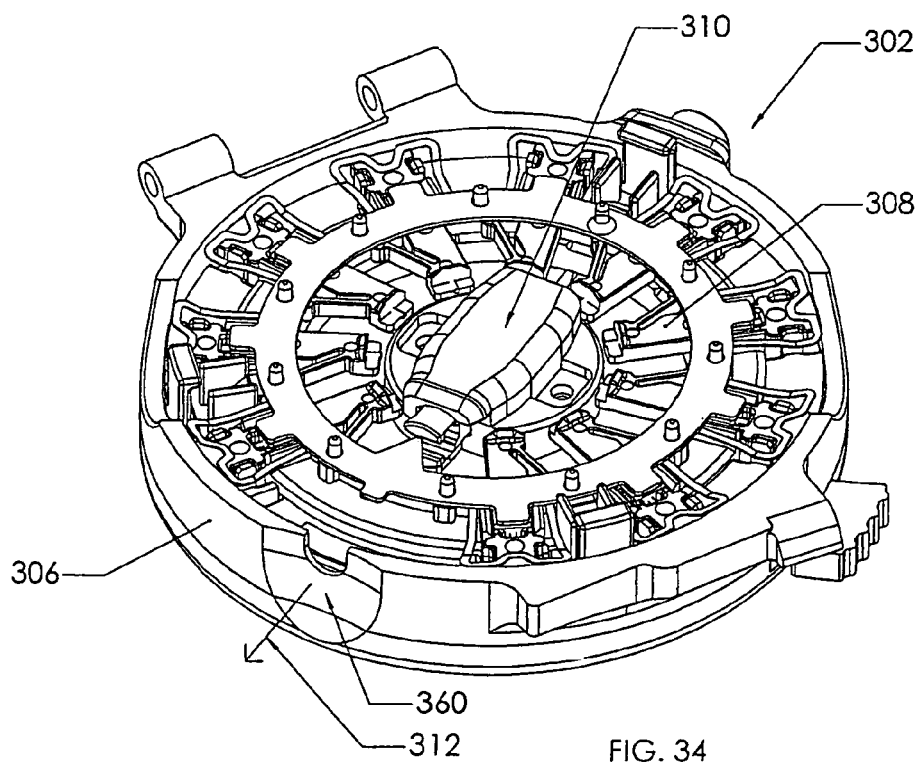

FIG. 34 shows a partial interior view of the sampling device of FIG. 33.

Figure 35:
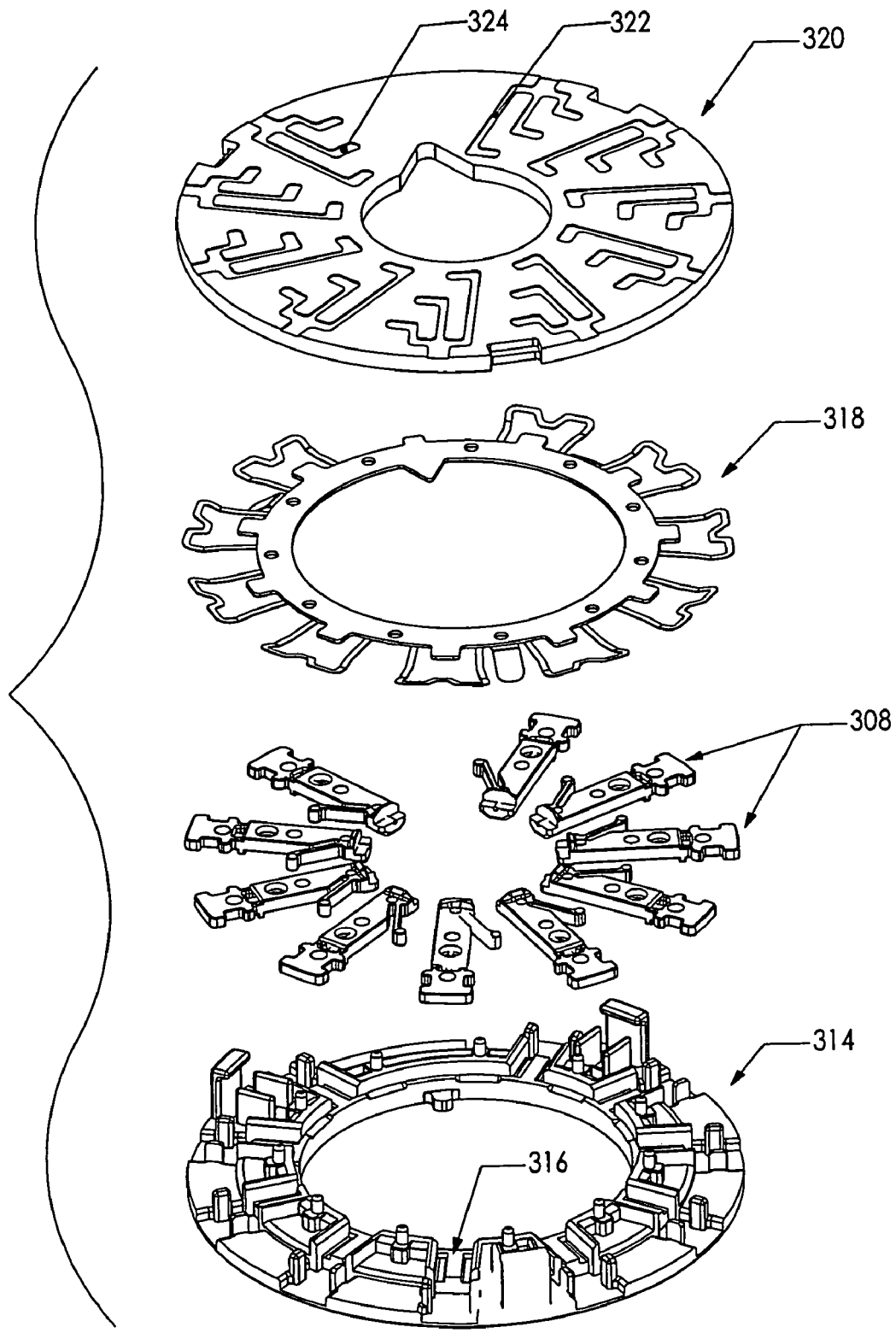
Figure 36:
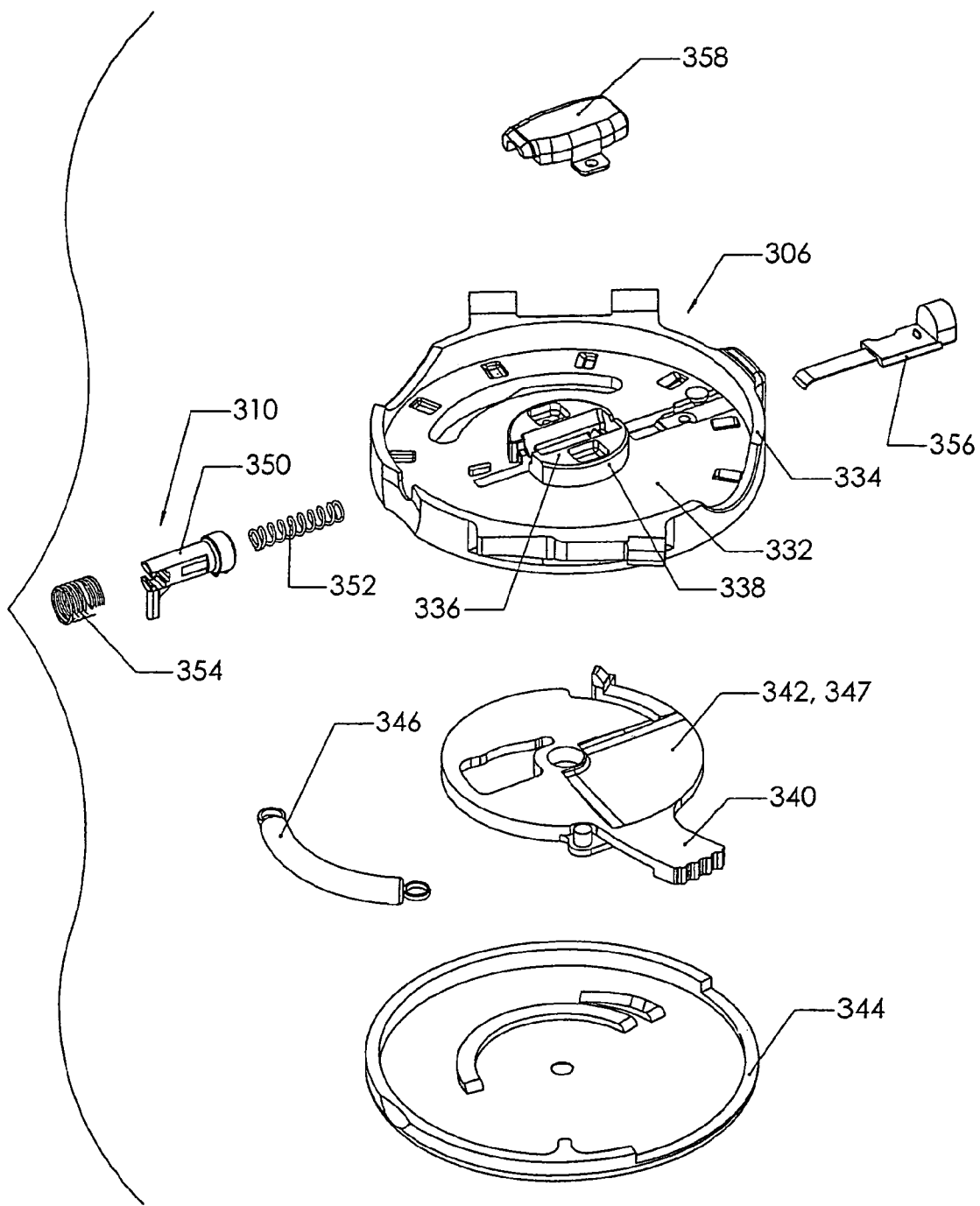

FIGS. 35 and 36 show exploded views of components of the sampling device of FIG. 33.

Figure 37:
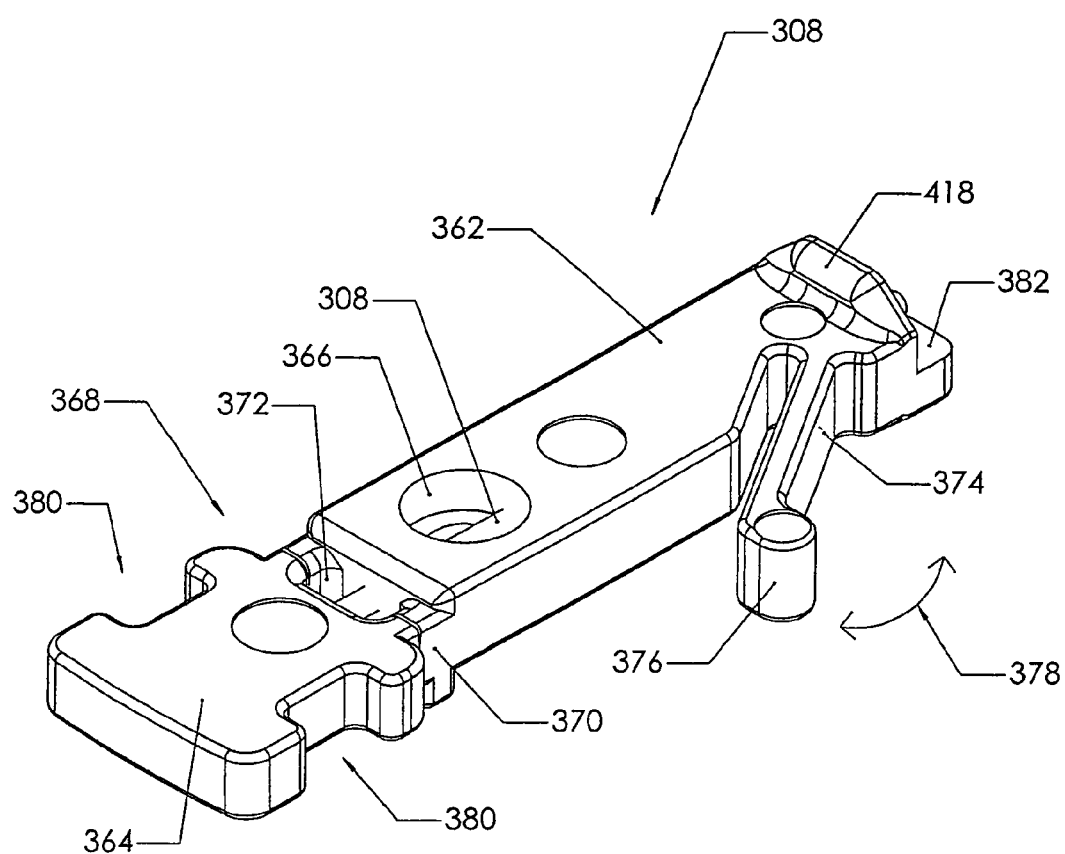

FIGS. 37 and 38 are detailed views of an example embodiment of a lancet of the sampling device of the present invention.

FIGS. 39a-c show a process for producing a lancet according to an example embodiment of the invention.

Figure 40:
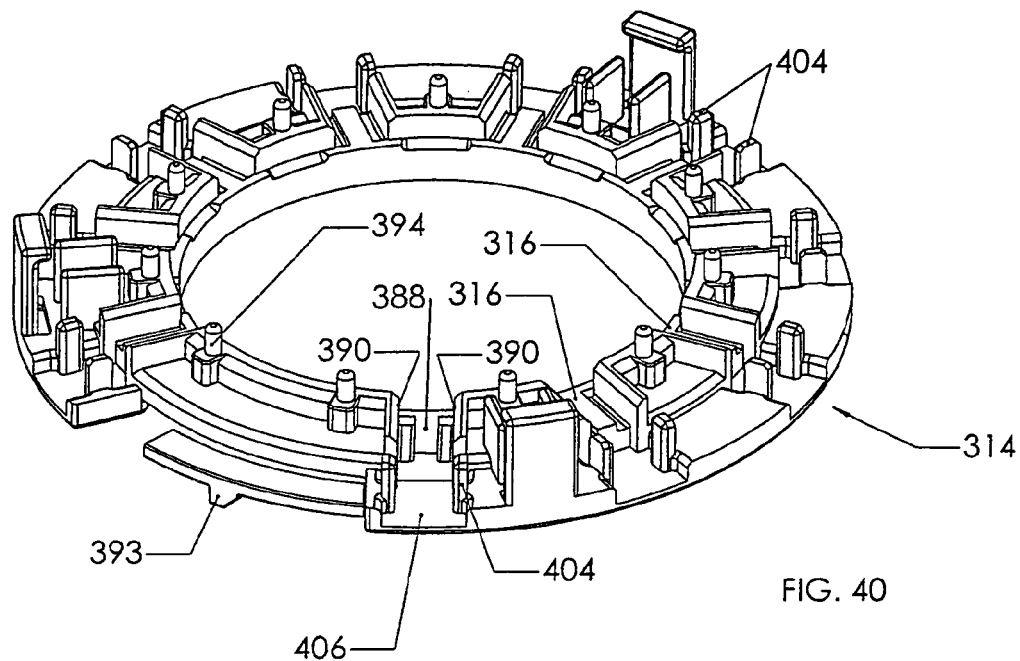

FIG. 40 is a perspective view of a lancet carrier according to an example embodiment of the present invention.

Figure 41:
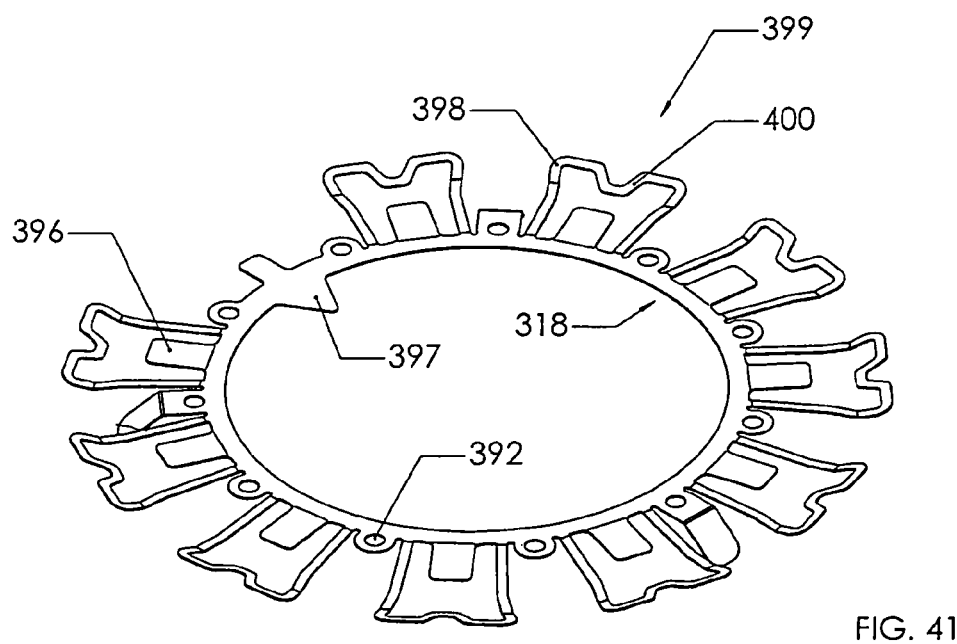

FIG. 41 is a perspective view of a retainer ring according to an example embodiment of the invention.

Figure 42:
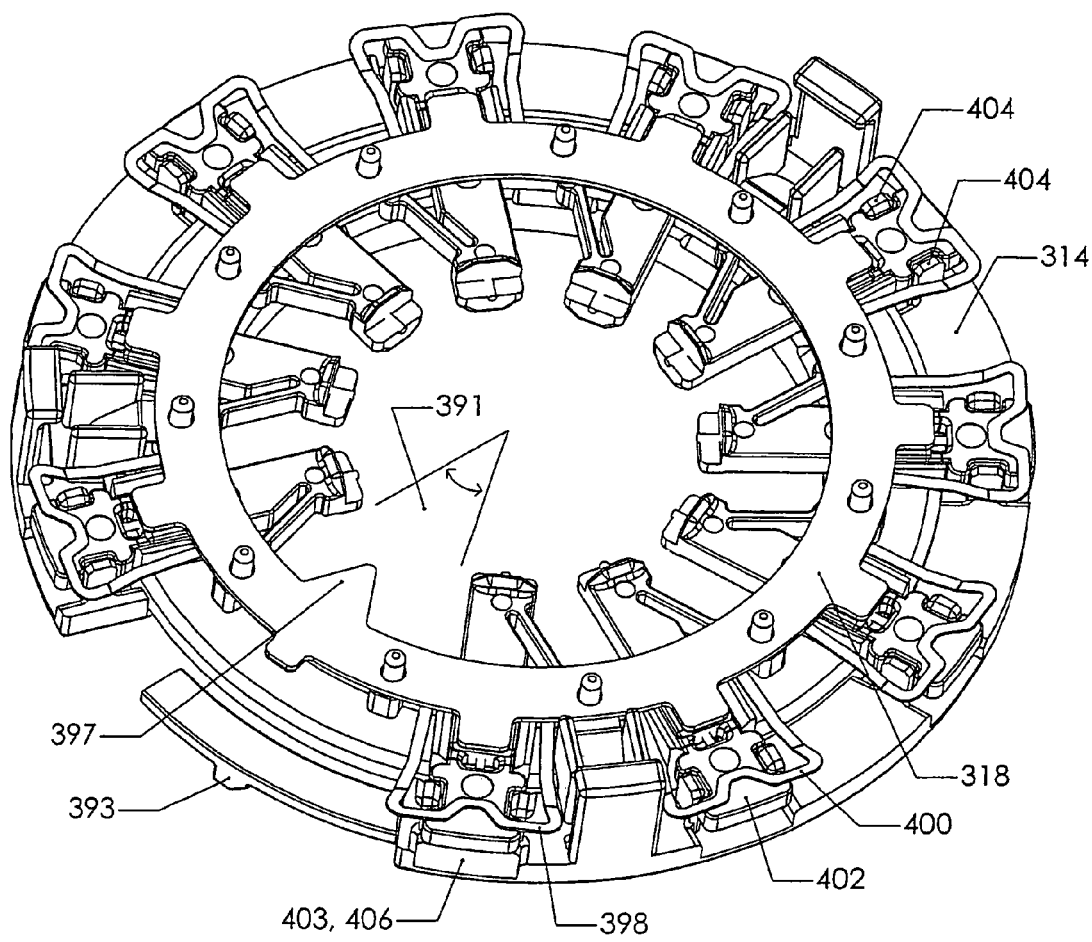
Figure 43:
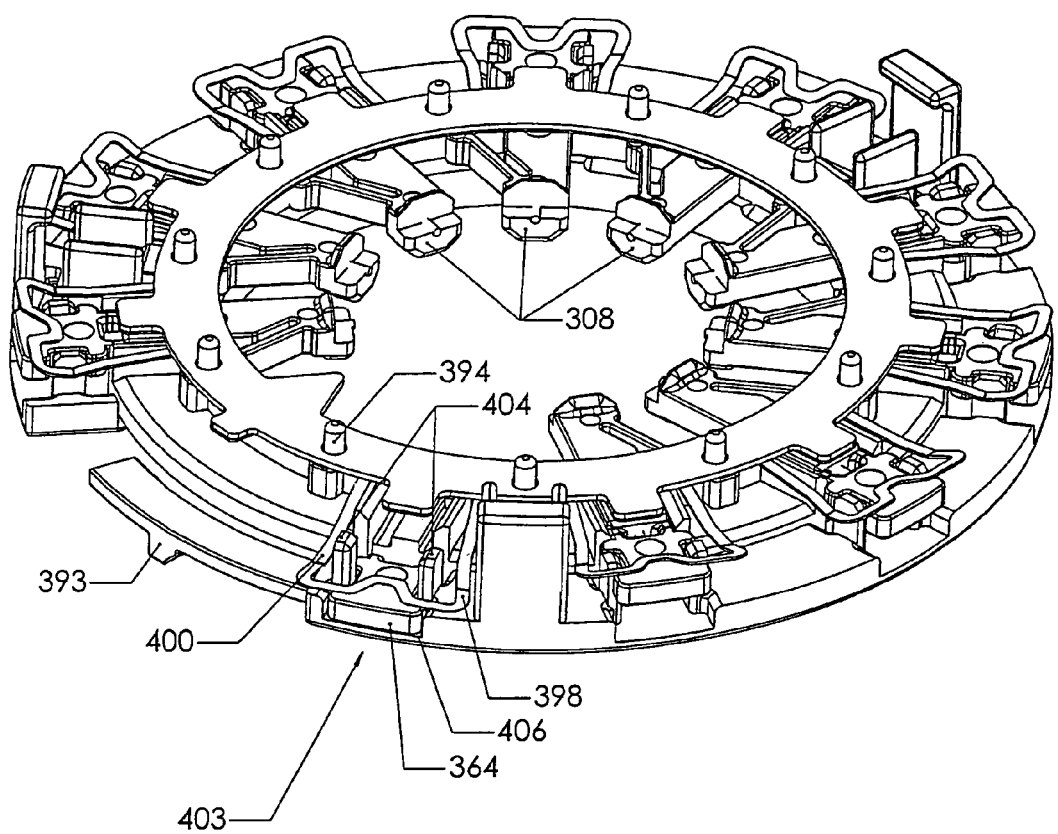

FIGS. 42 and 43 are perspective views of the carrier and lancets of a sampling device before and after use, respectively, according to an example embodiment of the present invention.

Figure 44:
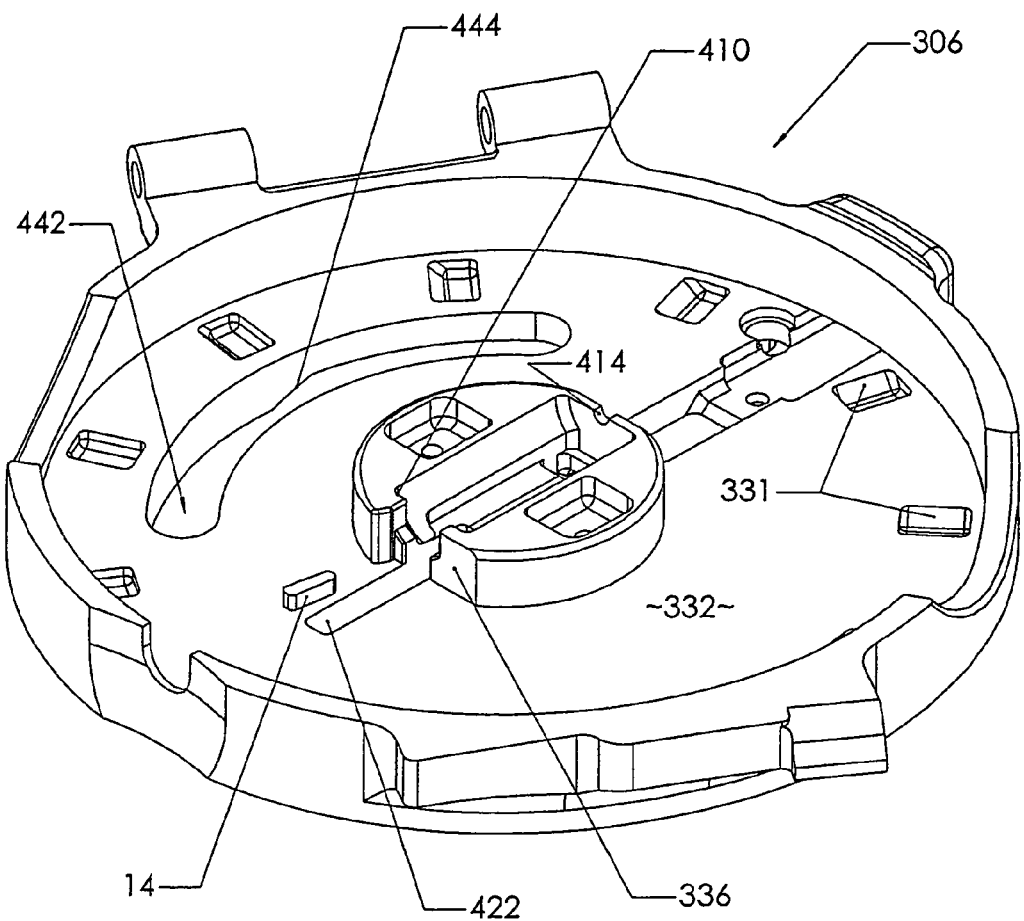
Figure 45:
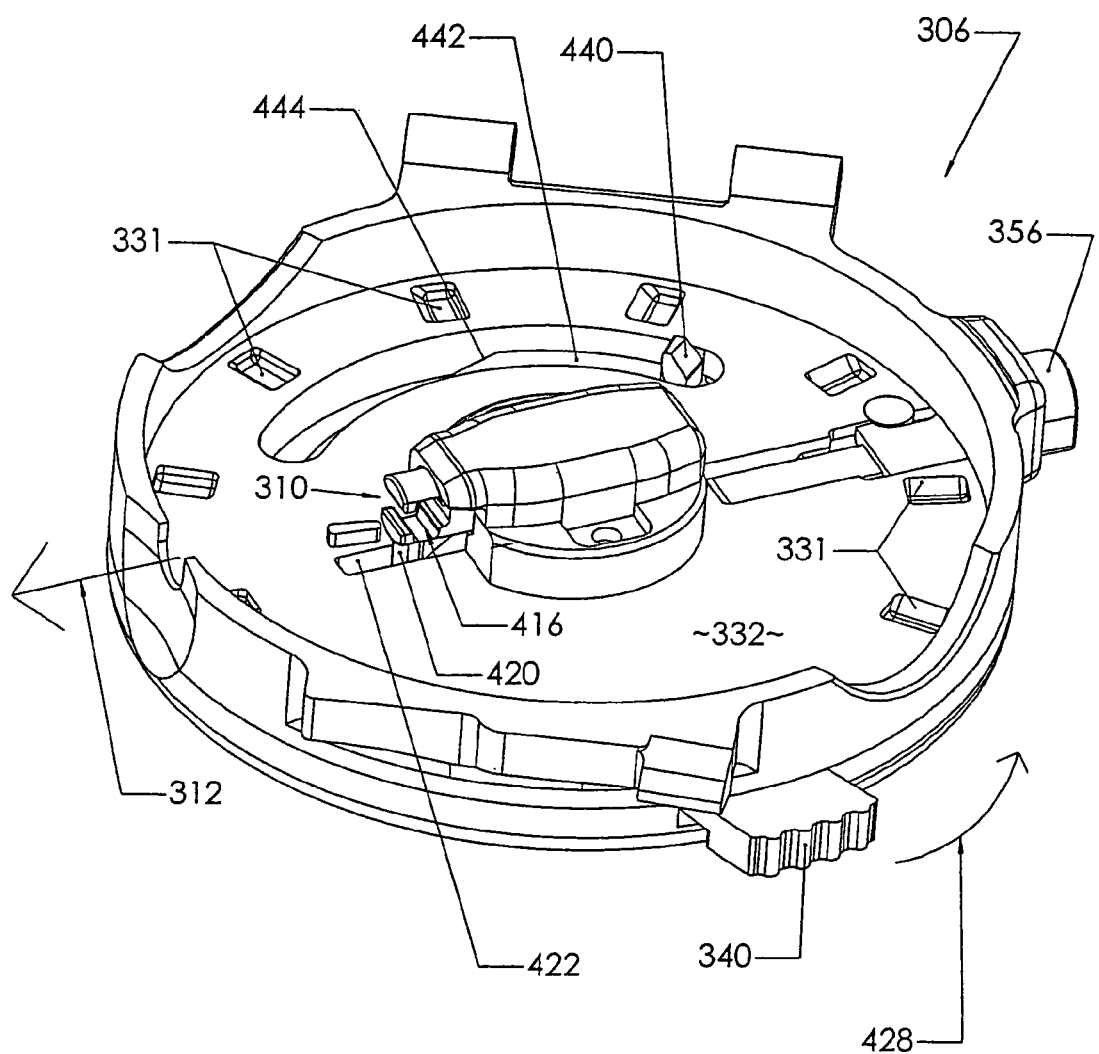

FIGS. 44 and 45 are partial perspective views of the housing of a sampling device, according to an example embodiment of the invention.

Figure 46:
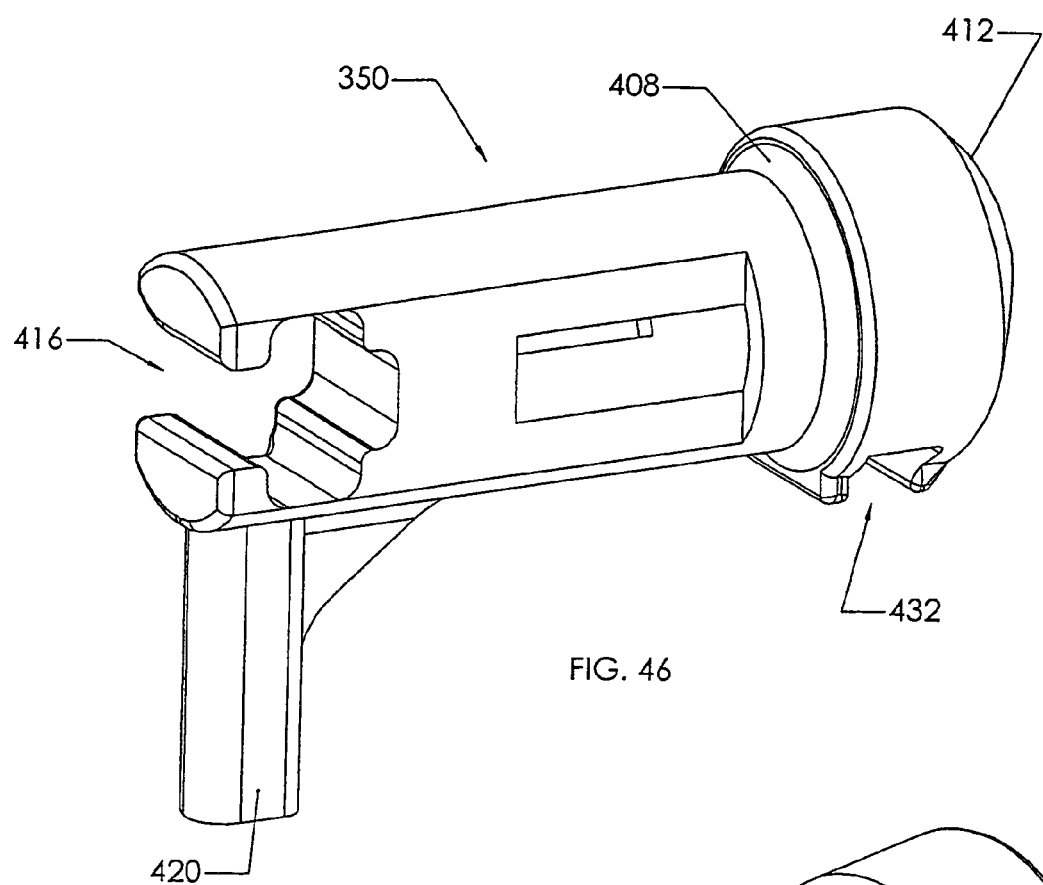

FIG. 46 is a perspective view of a piston or plunger element of the sampling device, according to an example embodiment of the present invention.

Figure 47:
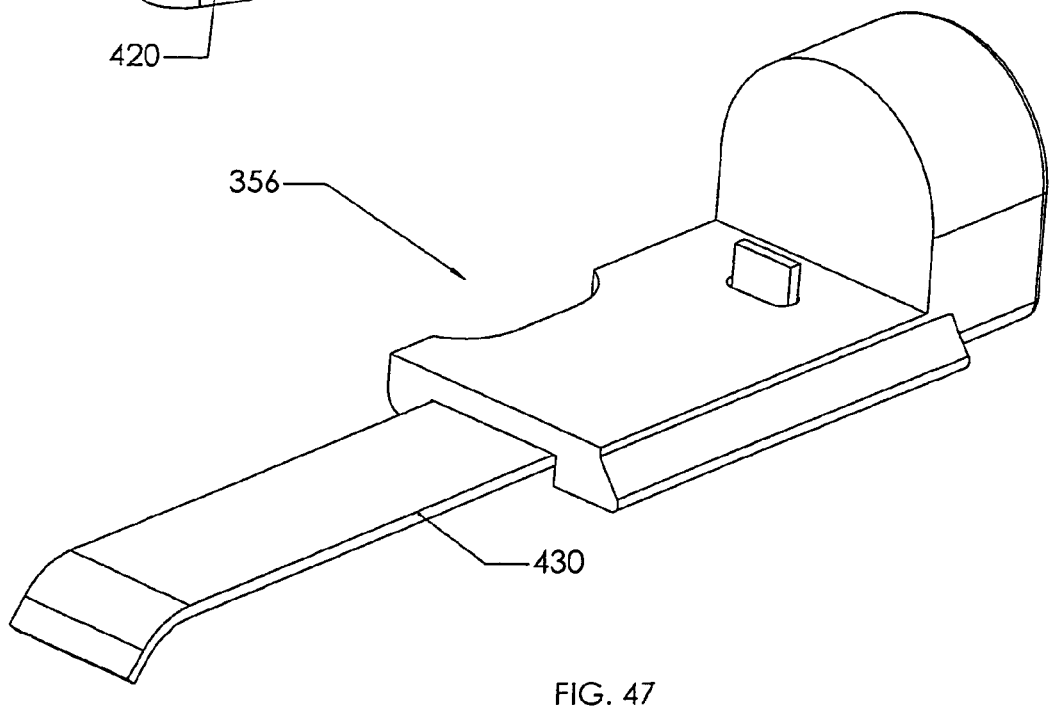

FIG. 47 is a perspective view of a release element of the sampling device, according to an example embodiment of the invention.

Figure 48:
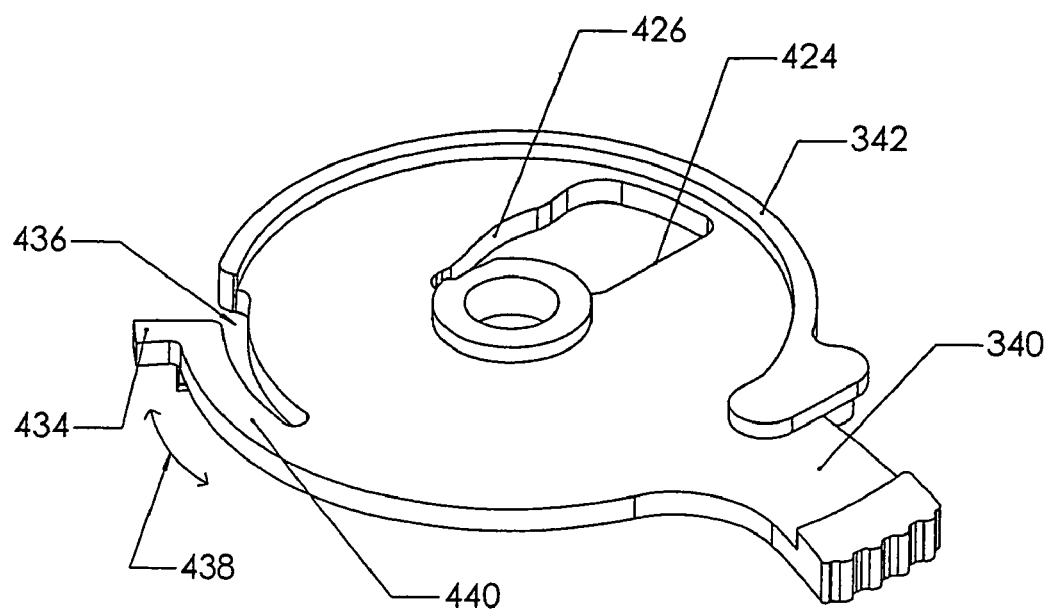

FIG. 48 is a perspective view of a tensioning or arming wheel element of the sampling device, according to an example embodiment of the present invention.

Figure 49:
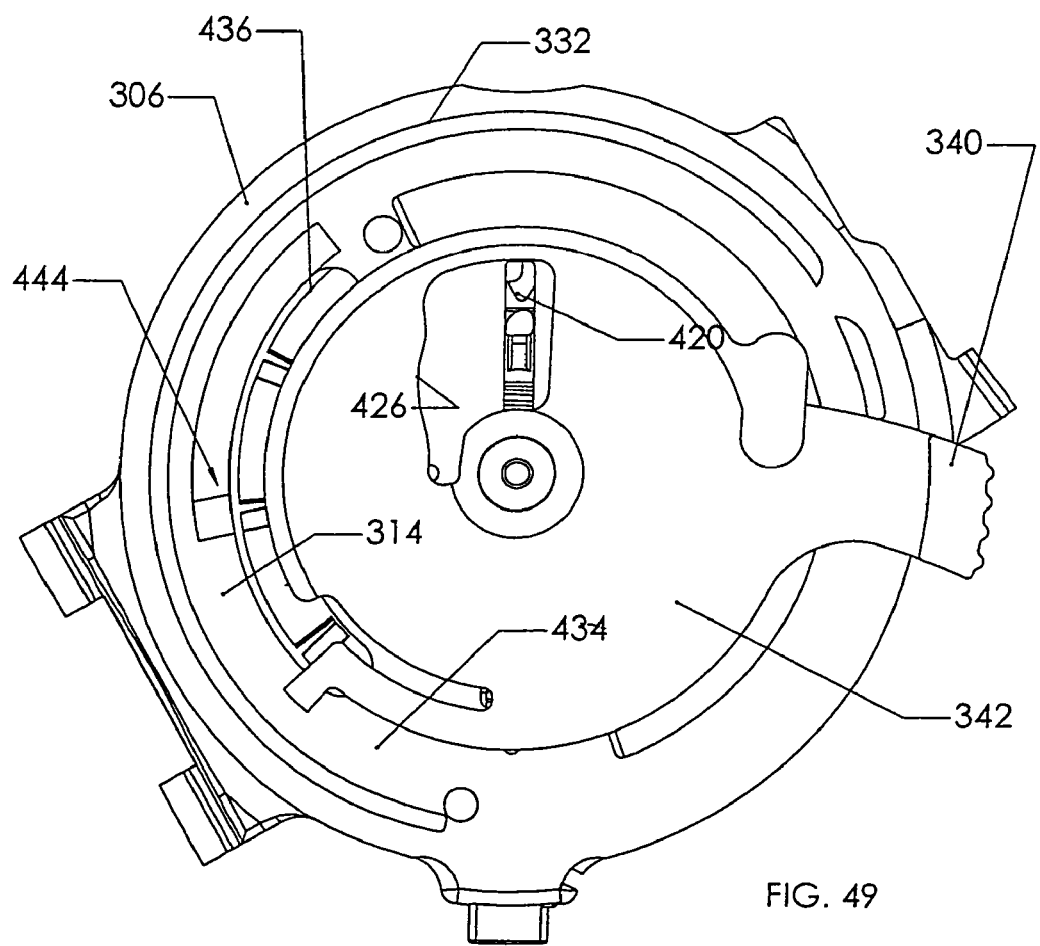

FIG. 49 is a bottom view of the sampling device, with the lower cover removed, according to an example embodiment of the invention.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
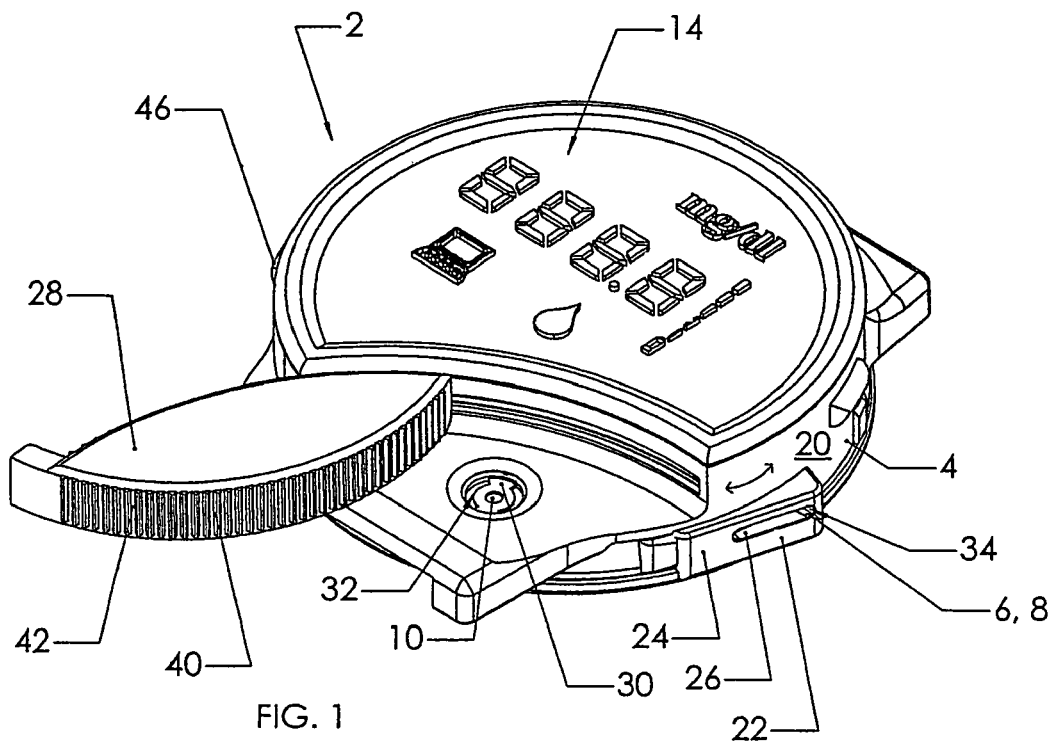
FIG. 1 shows a perspective view of a sampling device according to one example embodiment of the invention.
Figure 2:
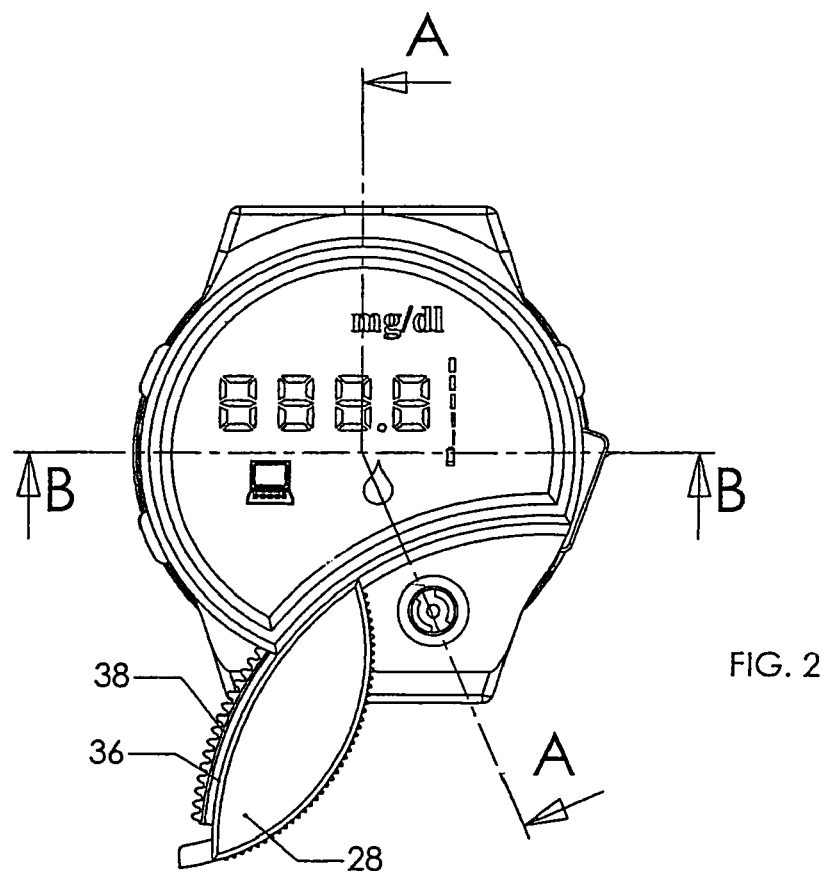
FIG. 2 shows a plan view of the sampling device of FIG. 1.

FIGS. 1 and 2, as a perspective and plan view respectively, show a blood analysis device according to one example embodiment of the invention, which as a whole is designated by the reference number 2. The blood analysis device comprises a housing 4, which contains a blood withdrawal system 6 comprising at least one, and preferably a plurality of lancets 8; and at least one, and preferably a plurality of test elements 10. Unused lancets 8 and test elements 10 are stored in the housing 4, used, and, after use, removed again to be discarded or disposed of. The blood analysis device 2 preferably further comprises an evaluation system 12, preferably comprising an electronic evaluation system and a display 14, preferably in the form of a visually readable display to show the result of an evaluation, such as for example the display of the quantity of an analyte such as blood sugar content. The depicted embodiment is an "all-in-one" device, comprising lancing features and sample collection and analysis features. In alternate embodiments of the invention, the invention is a lancing device, comprising only the lancing features, substantially as described, and omitting the sample collection and analysis features. In other alternate embodiments, the invention is a sampling device, comprising only the sample collection and analysis features, and omitting the lancing features.

The housing 4 of the blood analysis device 2 preferably comprises a generally circular disk, having the general size, shape and appearance of the housing of a wristwatch. It preferably also comprises a pair of mutually opposing mounting elements 16 in the form of two openings 18 aligned with each other to hold a pin of an ordinary watchband, so that the device may be worn on the wrist of a user in the manner of a wristwatch. A puncture position 22 for application against a skin surface, such as a finger of a user, is provided at a wall 20 of the housing 4. The puncture position 22 preferably comprises a sliding ramp 24 defining a slotted opening 26 through which a lancet 8 is driven to pierce a skin surface of the user to obtain a sample of blood. The ramp 24 is slidable along the wall 20, to adjust the depth of penetration of the lancet 8. The lancet 8 is shown in FIG. 1 in its maximally extended position, which the lancet takes on for only an extremely brief time during performance of a puncture process. In the non-actuated state of the blood withdrawal device 6 the lancet 8 is fully within the housing 4.

As can be seen from FIGS. 1 and 2, a convex segment 28 of the housing 4 can be moved partially out of the housing 4 so that the segment 28 opens exposes application position 30 which is oriented axially to the plane of the disk-shaped housing 4. In this application position 30, a minimal amount of blood is applied to a test element 10 immediately below this application position. When a test element 10 is positioned beneath the application position 30 on the housing, wherein it can be wetted by a sample of blood, it is designated as being in its operating position. Correspondingly, when a lancet 8 is in the puncture position 22, in which it can penetrate into the skin surface of a user, it is designated as being in its operating position. The cover segment 28 is preferably retained on a slide rail guide 38 so that it can be moved along a side 36 of the housing, which is curved convexly with respect to the inside by means of a rear grip on the remainder of the housing. The segment 28 preferably covers the application position 30 in the non-actuated state of the blood withdrawal device so that its other convexly curved side 42, preferably having a ribbed or other gripping surface 40, forms a continuous part of the outer periphery of the housing 4.

When a sample analysis is to be performed, the user slides cover segment 28 to the open position shown in FIG. 1, so that the application position 30 is exposed. This movement simultaneously cocks or activates the blood withdrawal device 6 inside the housing 4, in that a piston or plunger mechanism is armed, as by mechanically tensioning or compressing a drive spring. The user then places a finger or other sampling site against the puncture position 22 of the housing, and releases the blood withdrawal device, as by actuating a trigger button 46 the piston or plunger 48 of the drive mechanism 44 is driven radially outward, propelling the lancet outward into its operating position 34, so that it penetrates into the skin surface of a user through the slotted opening 26. The user removes his or her finger from the puncture position 22, allows a small sample of blood or other body fluid to exude from the wound, and then places the sample against the application position 30, thus transferring a sample of body fluid to the test elements 10 in its operating position 32. Then the evaluation of the analysis begins, and the result is displayed by the display means.

Figure 4:
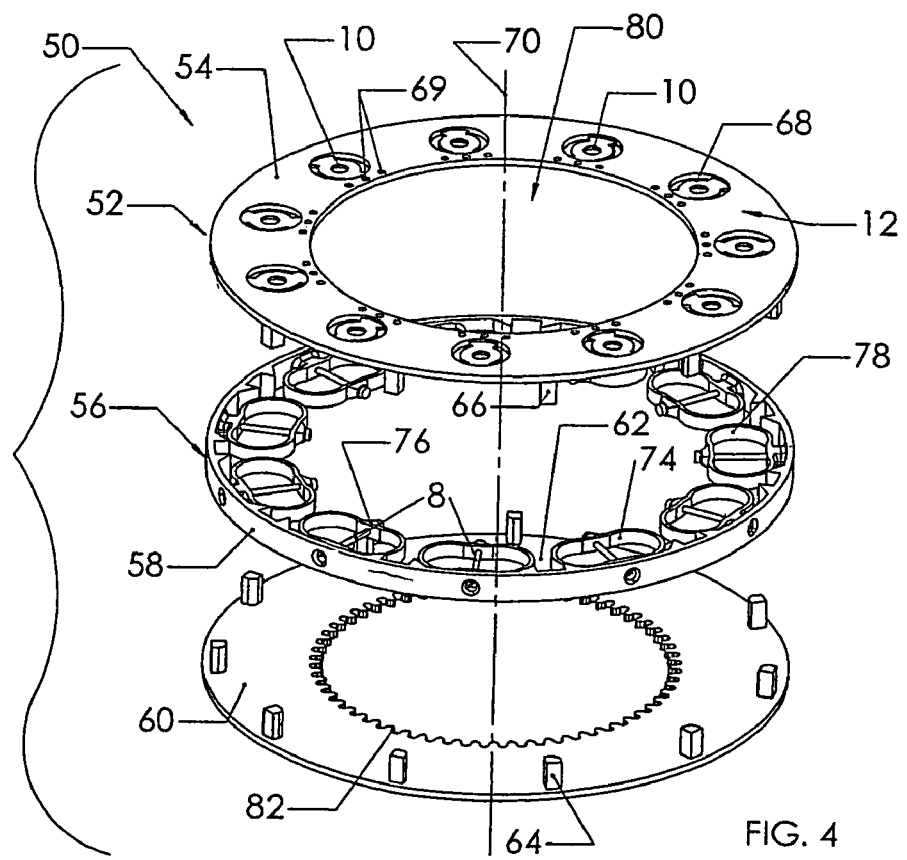
FIG. 4 shows an exploded representation of a carrier with lancets and test elements of the sampling device of FIG. 3.
Figure 5:
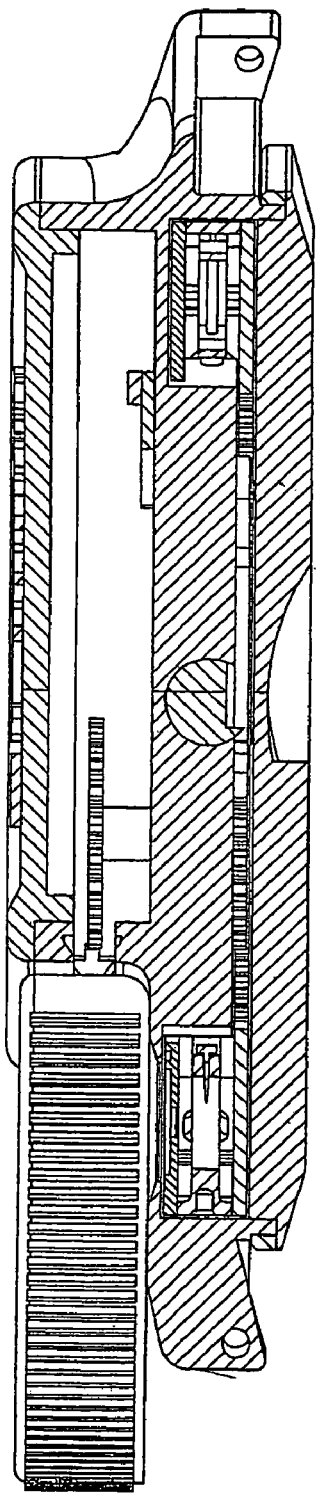
FIG. 5 is a view along a sectional plane through arrows A-A of FIG. 2.
Figure 5:
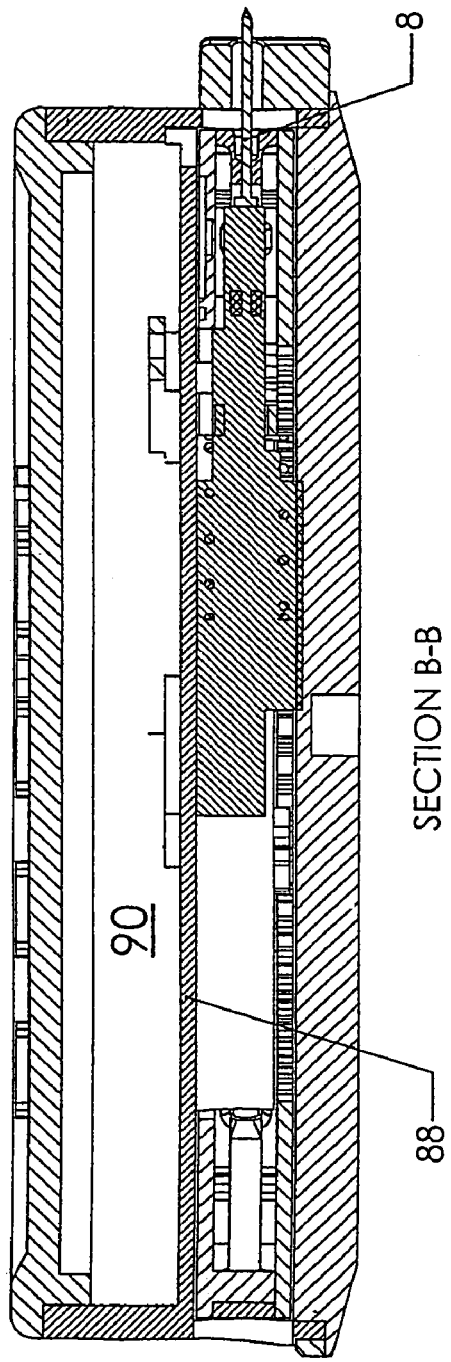

FIGS. 4 to 6 show an example embodiment of an arrangement of lancets 8 and test elements 10 according to the present invention, in connection with a blood withdrawal device 6 and plunger mechanism 44 within a housing 4. FIG. 4 shows a perspective view of a carrier or cassette 50, according to an embodiment of the invention, and comprising a plurality of lancets 8 and a plurality of test elements 10. The cassette 50 is a magazine-like holder for lancets 8 and test elements 10, which is manually manipulated for insertion into the device, for removal and replacement after use, and for disposal after use. The cassette 50 preferably comprises a first carrier part 52 in the form of a generally flat circular disk 54 for retaining the test elements 10, and a second carrier part 56 in the form of a strap or belt 58 formed into a circular ring with lancets 8 secured radially at spaced locations about its circumference. The second carrier part 56 is preferably mounted on another ring-shaped third carrier part 60, the plane of which extends generally parallel to that of the first carrier part 52. The second carrier part 56 and the third carrier part 60 are preferably coupled by engagement of recesses 62 in one part and projections 64 on the other part. The first carrier part 52 is preferably coupled to the second carrier part 56 in a similar manner, so that recesses 62 and projections 66 interengage.

The test elements 10 are mounted concentrically within recesses 68 in the first carrier part 52. The test elements 10 are preferably oriented so as to be accessible in the axial direction (i.e., in the direction of an axis of rotation 70 of the carrier 50). Contacts 69 are indicated for each test elements 10 on the top of the first carrier part 52. An electrode system, not shown, preferably contacts the test elements at the contacts 69 for communication with the evaluation system electronics, for example in the manner of known electrochemical test element operation.

The radially arranged lancets 8 on the second carrier part 56 each pass through a corresponding spring element 74, which can be tensioned in the radial direction to arm and actuate the lancing device. The lancets 8 have thickened heads 76 at the radial inside, which cannot pass through the spring element 74. When the lancet 8 is driven outwardly in the radial direction, the spring element 74 is compressed, producing a spring force that withdraws the lancet 8 back into an equilibrium position inside the housing 4, essentially as shown in FIG. 4. The spring elements 74 thus serve as retraction means 78 for the lancets 8.

Figure 3:
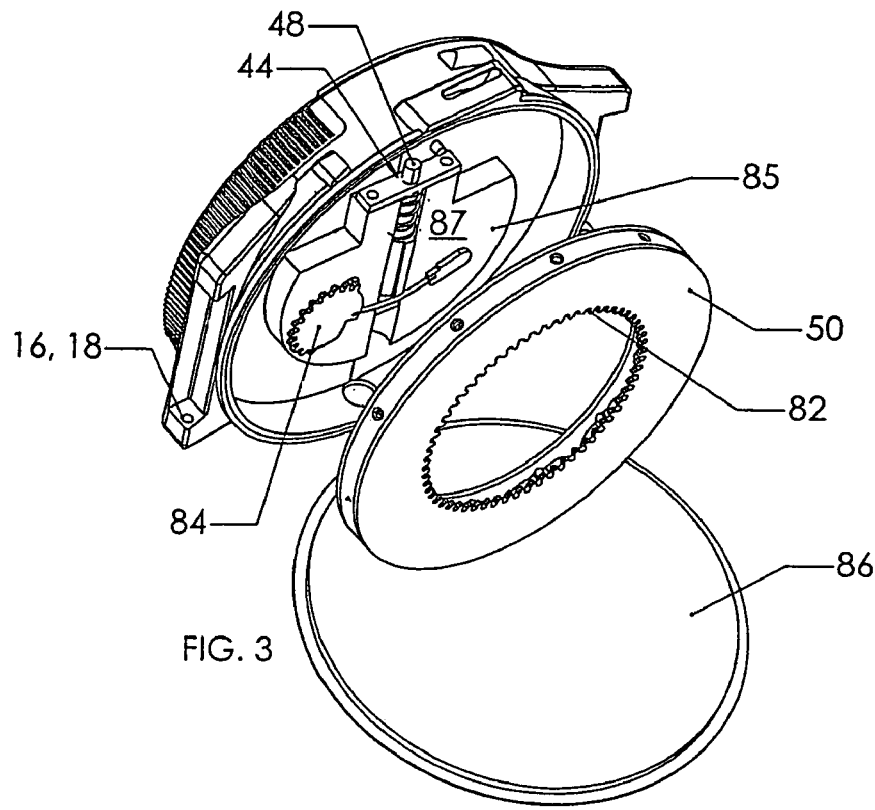
FIG. 3 shows an exploded view of the sampling device of FIG. 1 having an open housing.

The three carrier parts 52, 56 and 60, are preferably formed in the shape of rings, and have a central opening 80 in which the piston or plunger mechanism 44 is situated, as can be seen from FIG. 3. The other carrier part 60 preferably comprises internal gearing 82, which interacts with a drive gear 84. The drive gear 84 is driven to advance the cassette 50 through sequential operating positions, as by an electric motor or manually as by actuation of a slide or by rotation of a manually operable wheel on the housing of the device. The cassette 50, as shown in FIG. 3, is preferably mounted rotationally on a projection 85 of the housing, which extends into the opening 80. In this way, a plan axial surface 87 forms an axial bearing surface against which the other parts of the carrier part 60 lie so that they can slide, on the surface region immediately adjacent to the internal gear 82.

Figure 7:
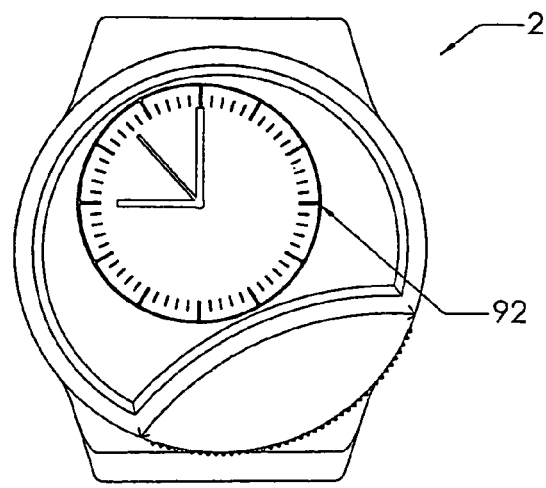
FIG. 7 is a plan view of a sampling device according to another example embodiment of the invention.

In the sectional view of FIG. 5, the plane of the section passes through the operating position 32 of the test elements 10. One lancet 8 can also be seen in the sectional view. However, it is not in the operating position for lancets. The operating position for lancets appears in the sectional plane of FIG. 6, in which the lancet 8 is shown in its maximally extended position. The plunger mechanism 44 shown in FIG. 3 is not shown in the sectional view of FIG. 6. It can be seen from FIGS. 3, 5 and 6 how the carrier 50 with the lancets 8 and test elements 10 can be inserted and removed as a replaceable cassette into the interior of the housing 4 of the blood analysis device. The housing 4 is preferably bounded at the bottom by a cover part 86 and at the top by a wall 88 running transverse to the axis of rotation 70. Above this wall there is space 90 for housing components of an electronic evaluation means 12 and associated display. FIG. 7 shows a plan view of a blood analysis device 2 which differs from that described above in that there is a time display means 92 in the form of an ordinary watch face on the visible side of the housing 4. This time display may be in the form of mechanical hands, or a digital display, for example using one or more LCD display elements. A switch is preferably provided to allow the user to select between a time display and an operating mode that displays the result of the blood analysis.

The depicted embodiment of the cassette 50 combines lancing elements and sample collection and analysis elements on a single replaceable cassette. It will be recognized, however, that the present invention also includes cassettes comprising the lancing elements only, and omitting the sample collection and analysis elements; as well as cassettes comprising the sample collection and analysis elements only, and omitting the lancing elements. Separate lancing cassettes and sample collection and analysis cassettes can be used in tandem in an all-in-one lancing and sample analysis device, or alternatively can be used independently in lancing devices or in sample collection and analysis devices.

Figure 8:
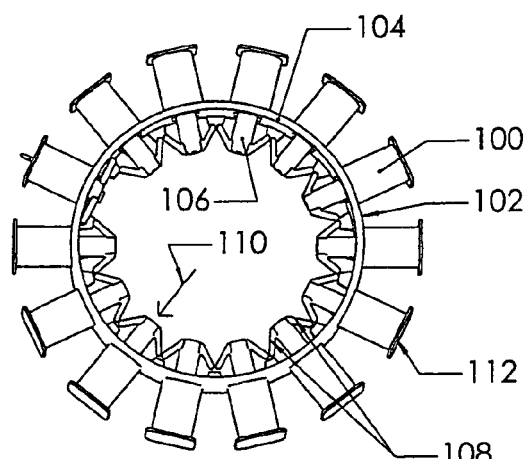
FIGS. 8 and 9 show a cassette of penetration elements and a detailed view of a lancet according to an example embodiment of the invention.
Figure 9:
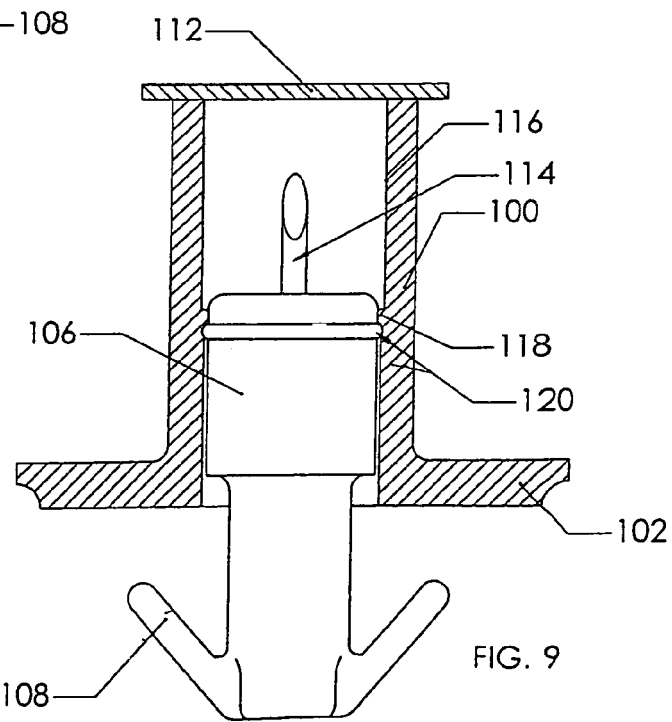
Figure 10:
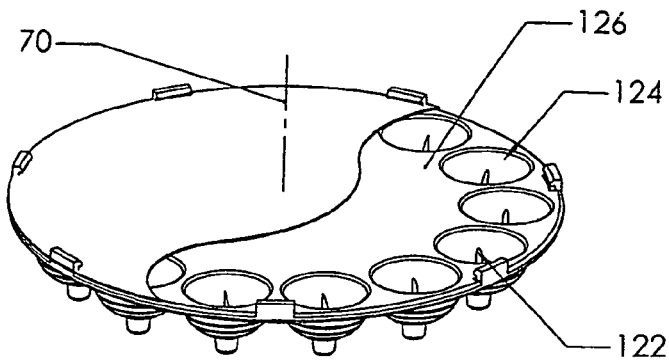
FIGS. 10-13 show a cassette of lancets according to another embodiment of the invention.
Figure 12:
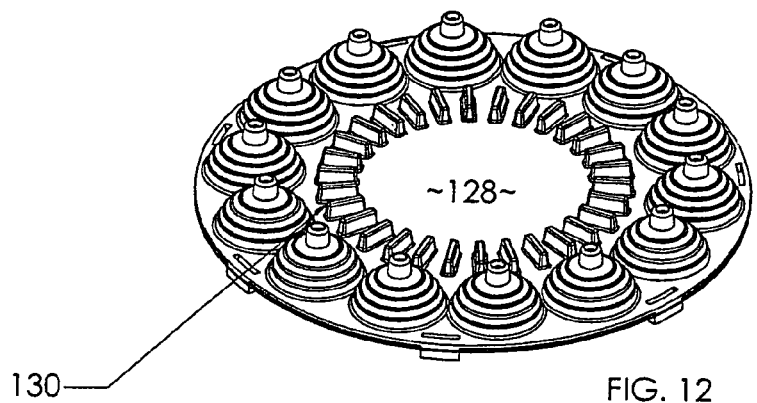
Figure 11:
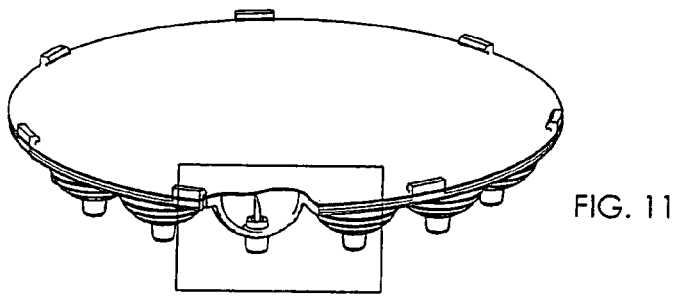
Figure 13:
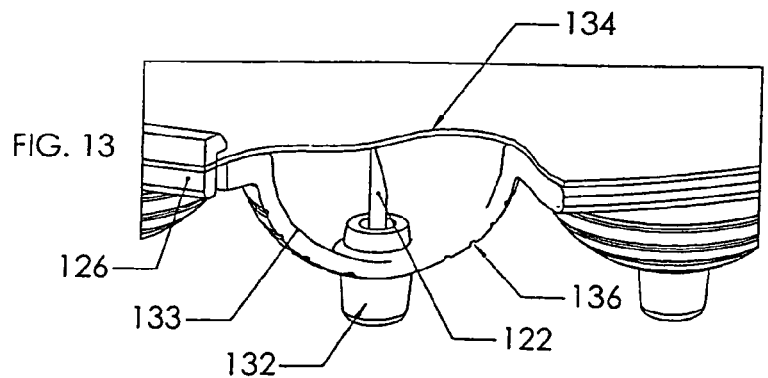

FIGS. 8 and 9 show a lancing cassette according to another embodiment of the present invention. A plurality of lancet elements are mounted on a band or belt 102. In the depicted embodiment, the lancets are radially arranged in spaced locations about the circumference of a continuous ring-shaped belt 102, in the form of a closed circle. Alternatively, a plurality of lancet elements are mounted along the length of a strip-like belt. Each lancet element comprises a piston 106 translationally mounted within a cylinder or sleeve 100. The piston 106 carries the sharp lancet tip 114 at one end. At least one resilient tongue 108 (two are shown) is mounted to the other end of the piston. Upon actuation, the piston 106 of a lancet element is driven outward, in the direction of arrow 110. The sharp tip 114 of the lancet projects outwardly of the sleeve 100, to pierce the skin at the sampling site. The resilient tongue(s) 108 are deformed and thereby exert a retraction force to withdraw the piston 106 a sufficient distance to shield the lancet tip 114 within the sleeve 100 after lancing. The lancing cartridge preferably further comprises a cover 112, for example in the form of a section of thin film, sealing the open ends of the sleeves 100 to maintain sterility of the lancet tip 114 prior to use, and to prevent inadvertent sticks. The cover 112 can either be penetrated by the lancet during lancing, or the cover can be removed partially or completely immediately before the lancing process is carried out.

FIG. 9 shows an enlarged cross-sectional view of a lancet element according to the embodiment of FIG. 8. Between the inner cylindrical wall 116 of the sleeve 100 and the piston 106 there is preferably a seal in the form of an annular protuberance 118 from the wall 116 and an abutting protuberance 120 from the piston 106. When the piston means 106 is driven outwardly in the direction of the arrow 100, the annular protuberance 120 slides over the annular protuberance 118 under the resilient action of the cylinder wall 116. Before the lancing process is carried out, the two annular protuberances 118, 120, form a seal for the cylindrical space within the sleeve, so that the lancet tip 114 is held under sterile and sealed-conditions. On the other side, the cylindrical space is sealed off by the film 112.

Figure 14:
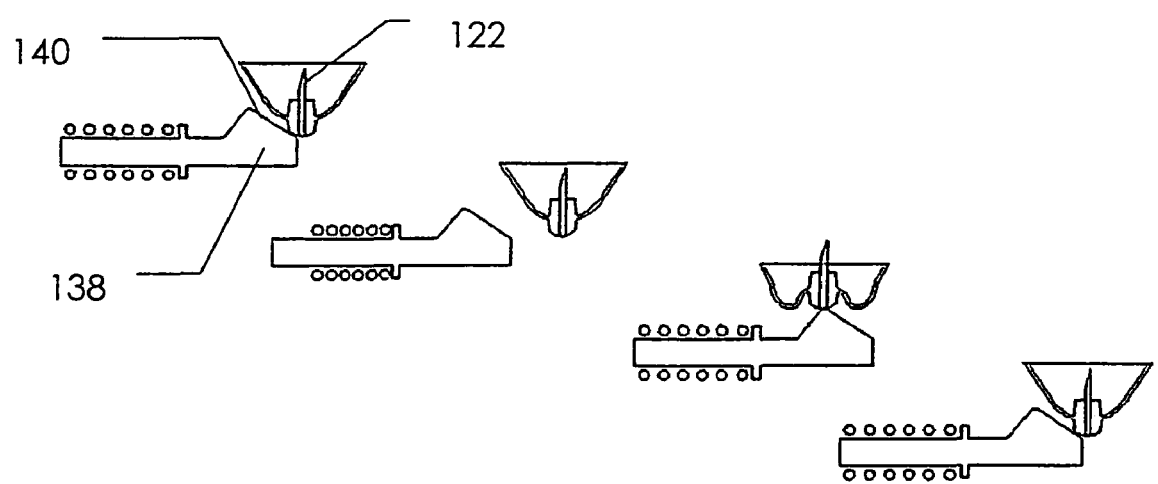
FIG. 14 shows an example drive mechanism for the lancets of FIGS. 10-13, according to an example embodiment of the invention.

FIGS. 10-13 show another embodiment of a lancing cassette according to the present invention, in which a plurality of lancets 122 are held in hemispherical depressions 124 in a disk-shaped carrier part 126, and are driven in the axial direction (i.e., parallel to the axis of rotation 70 of the carrier 126) upon actuation of the lancing device, as depicted in FIG. 14. The carrier 126 preferably comprises a ring of teeth 130 along one face 128, serving as an end gear for rotating the carrier 126 within a lancing device. Alternatively, a depression defining internal gearing is formed in the face 128 of the carrier. As can be seen from the detailed drawing of FIG. 13, each lancet 122 is mounted, as by injection-molding, potting, or the like, into a carriage lug 132, which is preferably integrally formed with the material of the hemispherical wall 133 forming the dome-shaped depression 124. The depressions 124 are preferably covered over by a film 134, which hermetically seals the enclosed space to surrounding the lancet tip 122 to preserve sterility and prevent inadvertent needle-sticks. The walls of the hemispherical depressions are preferably formed of a deformable and resilient material, and optionally further comprise annular weakening slots 136 for increased wall flexibility. FIG. 14 shows an example drive mechanism for a lancing device for use with this embodiment of lancing cartridge. A transversely-driven plunger 138 is arranged radially relative to the lancing cartridge. The plunger 138 comprises a wedge-shaped ramp 140 for impacting the carriage lug 132 and deflecting the dome-shaped depression to drive the lancet tip 122 in the axial direction. After lancing, the ramp 140 retracts, and the resilient wall of the carrier 126 returns to its dome shape, withdrawing the lancet tip away from the sample site.

FIGS. 15 and 16 show perspective and exploded views, respectively, of another embodiment of a lancing cartridge for use in connection with a lancing device and/or a combined lancing and sample analysis device, according to the present invention. A plurality of lancet elements are arranged on a rotatable carrier disk 142. The lancet elements each comprise a lancet tip 140 and a lancet body 144, and are preferably arranged generally radially on the carrier disk, and are preferably formed of injection-molded plastic. One or more resilient tongues 146 (two are shown) extend from the lancet body 144, to retract the lancet tip 140 away from the sampling site after lancing and prevent forward movement of lancet after firing. The carrier disk 142 preferably comprises guide projections projecting from its face to hold and act as a guide bearing for radial sliding movement of the lancet body 144 as it traverses a path between a retracted position and an extended position during the lancing operation. The lancets tips 140 are preferably injection-molded into the lancet body 144, and are preferably encapsulated by a protective cap 147, which provides a sterility and safety barrier for the lancet tip 140.

A spring member 148 is affixed to the carrier disk 142, serving as a guide allowing the lancet body 144 to translate back and forth in the radial direction, but preventing its loss or removal from the cassette. An extension arm 150 of the spring member 148 extends over each protective cap 147, and exerts downward pressure in the axial direction on the protective cap 147 toward the carrier disk 142. The lancet body 144 is retracted radially inward prior to actuating the lancing operation, for example in a cocking step, as shown in FIG. 17b. The protective cap 147 is constrained by the guide projections of the carrier disk 142 to ensure smooth travel of the lancet cap out of the firing position, and to prevent radial retraction of the cap, thereby separating the cap 147 from the lancet body 144 and exposing the lancet tip 140. As shown in FIGS. 17c and 17d, the extension arm 150 of the spring member 148 then presses the separated protective cap 147 into a depression 152 formed in the carrier disk 142, and out of the path of movement of the lancet. During the lancing operation, the lancet tip 140 is driven outwardly, through a passage in the extension arm 150, to pierce the skin at the sampling site, and is thereafter retracted away from the sampling site by the resilient tongues 146 and the retraction spring in the drive mechanism.

FIG. 18 shows schematically the means of activating a lancing device, according to an example embodiment of the invention. A drive mechanism 44 comprises a piston or plunger 154 that is preferably generally coaxial with the centerline of the lancet which can be driven longitudinally, in the radial direction relative to a disk-shaped lancing cartridge, and withdrawn again by means of a tension and compression spring 156. The plunger mechanism can be armed by actuating a pivotal cocking means 158 comprising a radially projecting cam 160. The cam 160 engages with a cooperating projection 161 on the piston 154 so that the piston is moved against the compression force of the drive spring 156 such that it is held in an armed state by a catch mechanism or trigger 162, holding the drive spring in tension. The positioning means 158 with the cam 160 can then return back to its starting position as for example under spring force. The trigger catch is then manually released, causing the piston 154 to be driven longitudinally in the radial direction under the force of the spring, so that the free end of the piston 154 strikes the inner end of the lancet or of a holder which carries the lancet, and that likewise projects outward. Alternatively, the end of the piston 154 comprises a clip or other engagement feature for engaging the lancet, and the lancet is carried along the traverse of the piston as it is cocked and released. Then the piston returns to its starting position as shown in FIG. 18 under the influence of the spring 156, and/or the lancet is withdrawn into the housing under the action of the resilient tongue(s) as described above.

FIGS. 19 to 29 depict an example embodiment of a lancing device according to the present invention. FIG. 19 shows an exploded view of a lancet cassette, which is shown in its assembled state from the top in FIG. 20 and from the bottom in FIG. 21. The lancet cassette comprises a carrier disk with a plurality of lancet elements 172 arranged radially thereon, each lancet having a sharp tip covered by a protective cap 174, in similar fashion to the embodiment of FIG. 15. The cassette further comprises a ring-shaped spring means 176 which interacts with each protective cap 174, substantially as described above in connection with FIGS. 17a-17d. These components are inserted into a housing mechanism base having a cylindrical wall region 180 extending upward. This mechanism base has in its center an opening 182 projecting into the interior, forming a housing for a plunger or piston 184, which is radially movable within it. Between a radial inner end 186 of the plunger 184 and a wall of the opening 182 which forms the housing, there is a first drive spring 188. A return spring 192 is provided between a ring collar 190 of the plunger 184 and the opening 182.

The plunger 184 also has a holder 194 at its circumference, preferably in the form of a circular slot by means of which the plunger 184 is held in the opening 182 with the spring 188 tensioned. A catch mechanism such as a clamping spring 196 preferably interacts with the holder. The plunger 184 has a rear grasping element 198 at its radially outer end, which serves to draw back the lancet element 172 so as to remove the protective cap 174. This rear grasping element releasably engages a cooperating section 200 of the lancet element 172.

This rear-holdable section can for example, comprise an expanded surface feature 201 of the lancet element 172 which receives and releasably engages a cooperating surface feature of the plunger 184.

On the outside of the carrier part 178, a control lever 202 is pivotally mounted about the axis of rotation 70 of the carrier part 170. The control lever 202 preferably has a cam control surface 204, which interacts with a cam means 206 of the plunger 184, which extends in the axial direction through a cutout 208 in the base of the carrier part 178. When the control lever 202 is pivoted clockwise (as shown in FIG. 21), then the cam control surface 204 comes into active contact with the cam 206 and, on further rotation of the control lever 202, forces the cam 206 with the plunger 184 radially inward so that the drive spring 188 is energized. A holding or catch mechanism, substantially as described above, retains the plunger 184 with the spring 188 in an energized state, even when the control lever is returned to the initial position shown in FIG. 21.

The control lever 202 also has a carrier 210 in the form of a notched lever 212, by means of which the carrier part 170 and, with it, the arrangement of lancets, is rotationally advanced for successive lancing operations. For this purpose the notched lever 212 projects through a curved slotted opening 214, extending along the peripheral direction in the base of the carrier part 178 and engages a cooperating portion of the carrier part 170. It is advantageous, for this purpose, for the carrier part to have a ratcheting, toothed end catch arrangement 216 as seen in FIG. 21. When the control lever 202 is turned clockwise from the position shown in FIG. 21, the notched lever 212 causes further rotation of the carrier part 170 so that a new lancet which has not yet been used is moved into its operating position. In the process the rear-graspable section 200 of the particular lancet element 172 slides into engagement with the rear grasping means 198 of the plunger 184. It is advantageous, to simplify this positioning end engagement, for the rear grasping means 198 to comprise an approach ramp or introductory ramp 218 which can be seen in FIG. 20 or FIG. 19. By means of this approach ramp 218, which is preferably formed on confronting radially internal and radially external surfaces, it is possible to compensate for inaccuracies in positioning the plunger 184.

To make sure that a particular lancet is positioned exactly in the operating position for the lancets and has not accidentally been carried past that position, an interruption mechanism 220, is positioned at the desired rotational position. This interruption mechanism 220 preferably produces axial outward deflection of the notch lever 212, so that its carrier 210 can no longer interact with the toothed end catch arrangement 216. For this purpose the notch lever 212 has a radial projection 222, which slides across an outer side of the carrier part 178. This outer side of the carrier part 178 has an approach ramp 224 at the appropriate place, which then raises the notch lever in the axial direction, in the sense described above, when the control lever 202 reaches this approach ramp 224 as it rotates. When the control lever 202 is rotated back, the carrier 210 of the notch lever 212 slides over oblique edges of the toothed end catch arrangement without rotating carrier part 170 backward. For reliable prevention of reverse movement of the carrier part 170, a means of preventing reverse rotation 226, such as a ratchet mechanism, is preferably provided. It can advantageously be produced by an appropriately oriented end catch gear 228 on the inside of the carrier part 178, as can be seen in FIG. 19, for example. This end catch arrangement 228 is made and oriented so that it interacts with the end catch arrangement of the first carrier part so that the carrier part 170 can be rotated in the direction of transport but not in the opposite direction. The carrier part 170 is slightly deflectable by means of a cantilever arm 171 with respect to the other carrier part 178 to facilitate this action.

Figure 22B:
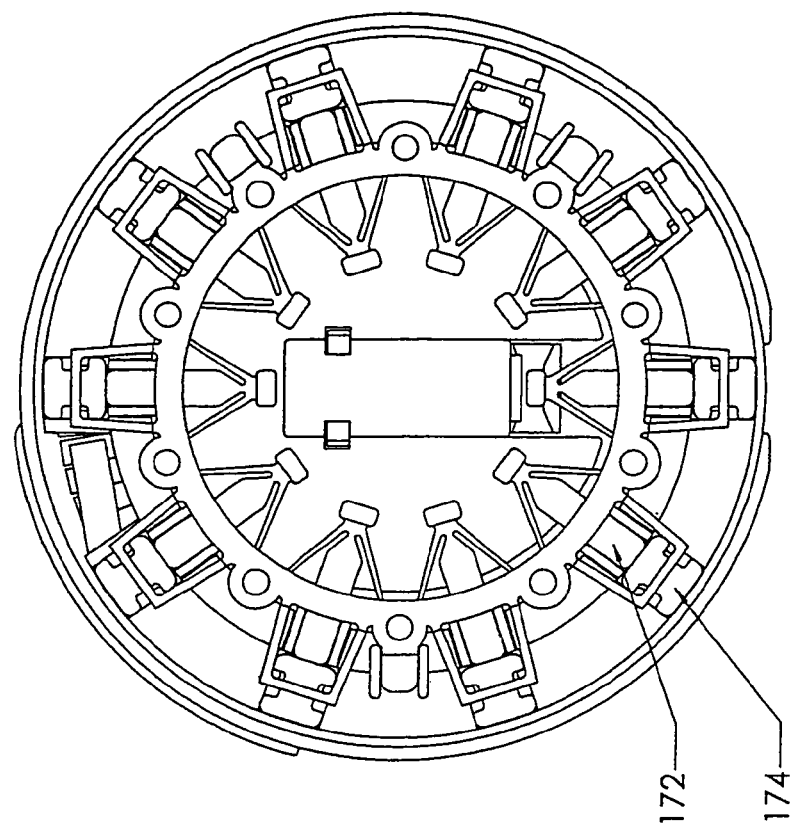
Figure 22A:
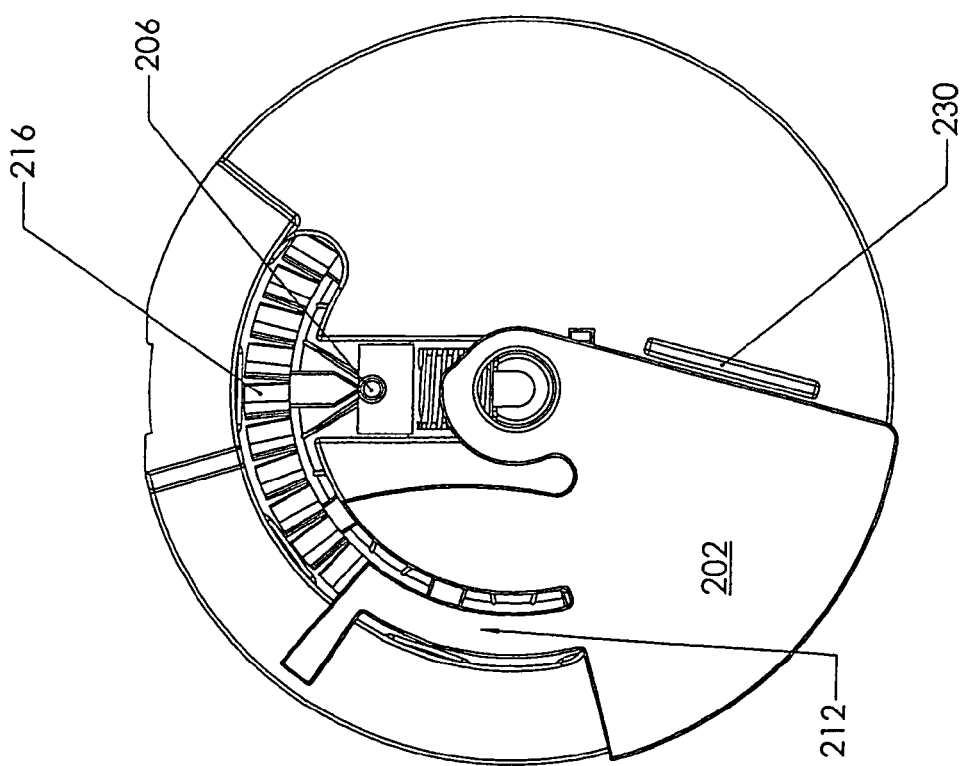
Figure 23B:
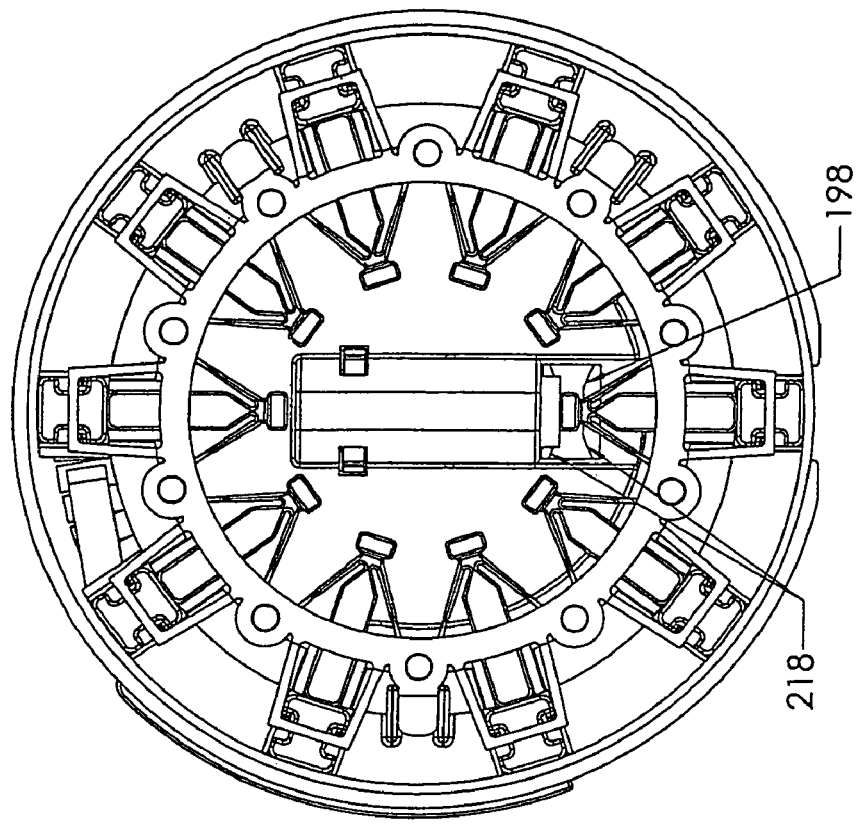
Figure 23A:
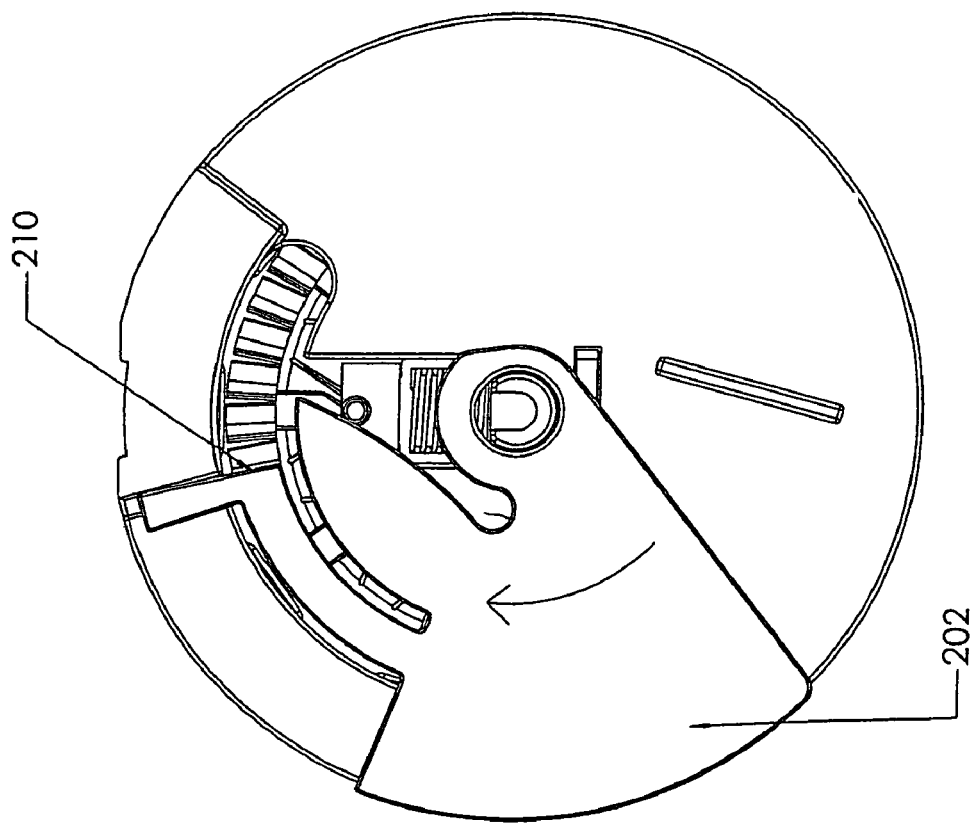

FIGS. 22 to 28 show an actuation cycle of the lancet arrangement, as described above. The left (a) view of each figure is a bottom view of the lancet cassette, and the right (b) view of each figure is a top view. FIG. 22 shows the control lever 202 in its starting position, against a terminal stop 230. At the right side of FIG. 22, a lancet element 172 with protective cap 174 is shown, emphasized, in a position in front of the operating position of the lancet. FIG. 23 depicts rotational movement of the control lever 202 in the clockwise direction. In this movement the tooth 212 of the cantilevered carrier arm 210 engages a cooperating tooth of the end catch ratcheting arrangement 216 to advance the carrier part 170 and transport or rotate the carrier part 170 and the lancets arranged on it, also in the clockwise direction, until the previously mentioned lancet element 172 reaches the operating position shown at the right in FIG. 23. FIG. 23 also shows the approach or introductory ramps 218, discussed above, at the rear grasping means 198 of the plunger means. When the control lever 202 is turned farther, as shown in FIG. 24, the radial projection 222 of the carrier arm is deflected by the approach ramp 224 in the axial direction, and the tooth 212 of the carrier arm 210 is disengaged from the carrier part 170 so that the carrier part 170 is not turned farther. At the same time, the cam guide surface 204 of the control lever 202 presses the cam 206 inward in the radial direction, and the plunger means 184 with it, so that the plunger spring 188 is tensioned and the firing mechanism is armed. Through interaction of the rear grasping means 198 and the rear-graspable section 200 of the lancet element 172, the lancet is carried radially inward, so that the lancet tip 232, seen for the first time at the right of FIG. 24, is released from the protective cap 174. Also, as the carrier arm 210 is deflected out of engagement with the carrier part 170, teeth 226 inside the base of the housing 178 engage the teeth 216 of the ratcheting arrangement on the carrier 170 to prevent the carrier from rotating back in a counter-clockwise direction.

Figure 25B:
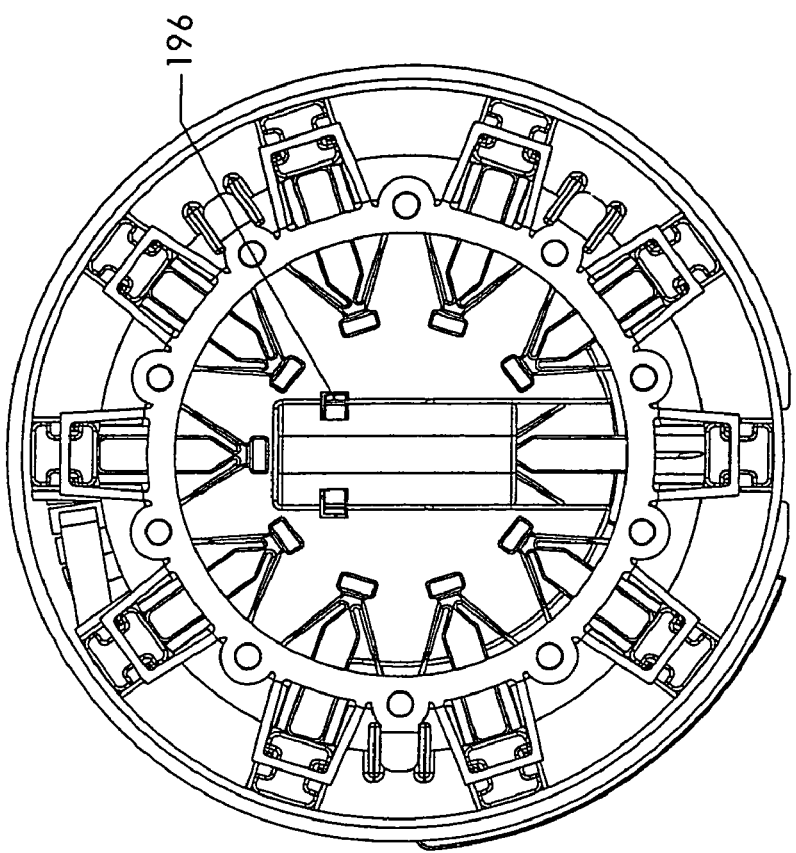
Figure 25A:
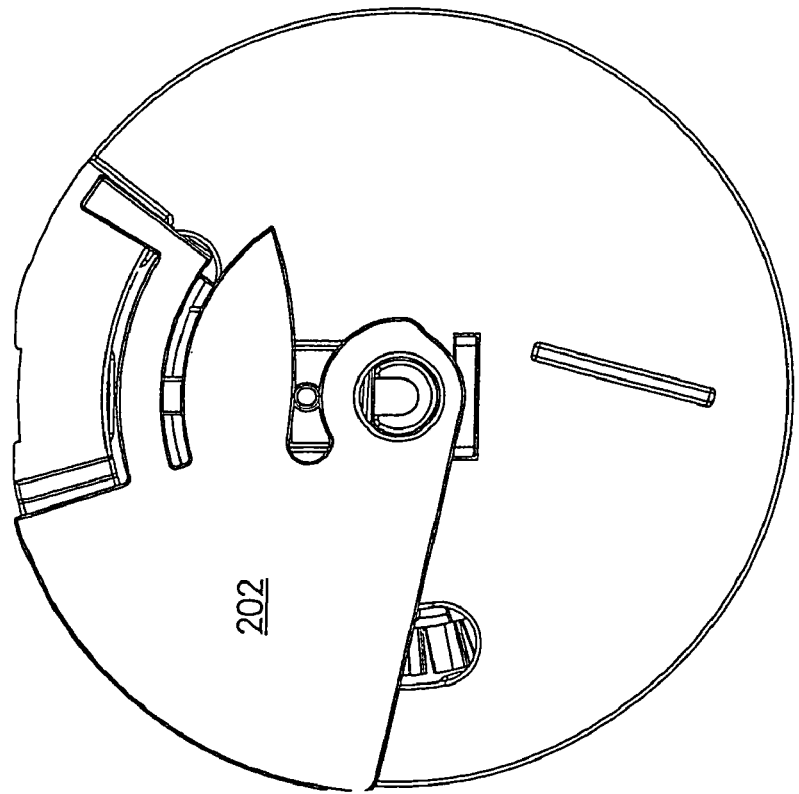
Figure 27B:
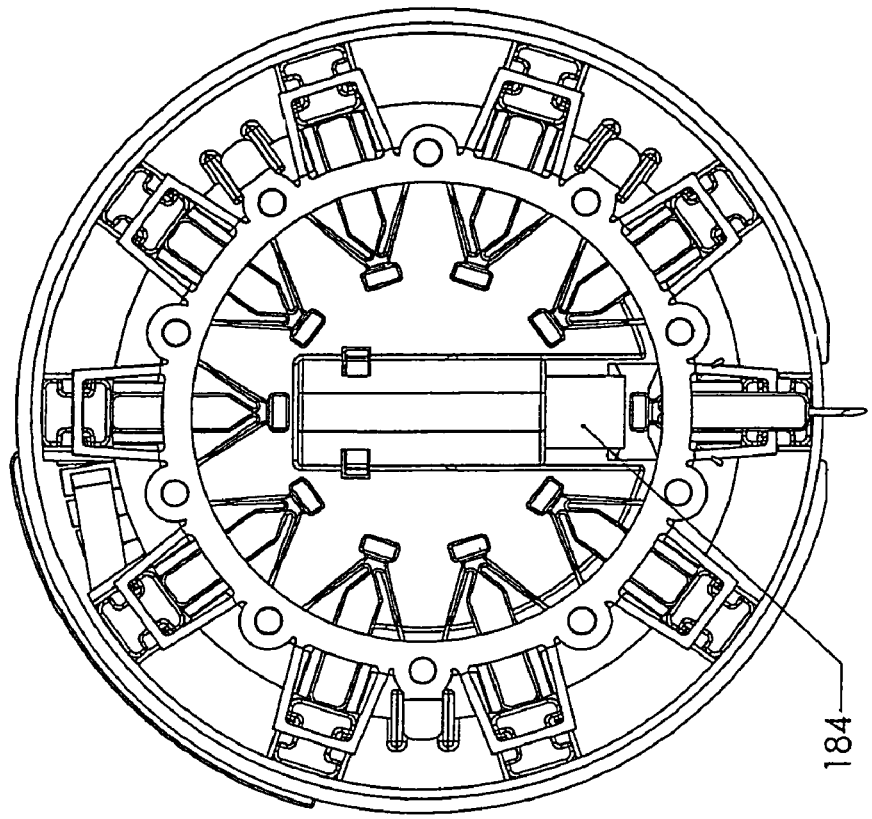
Figure 27A:
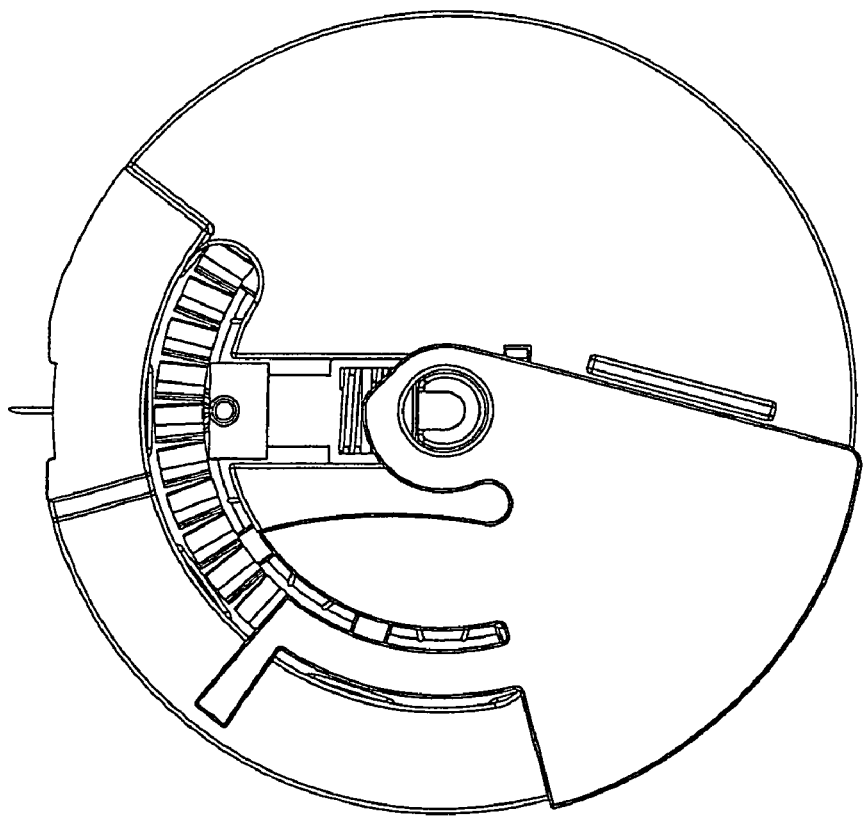
Figure 28B:
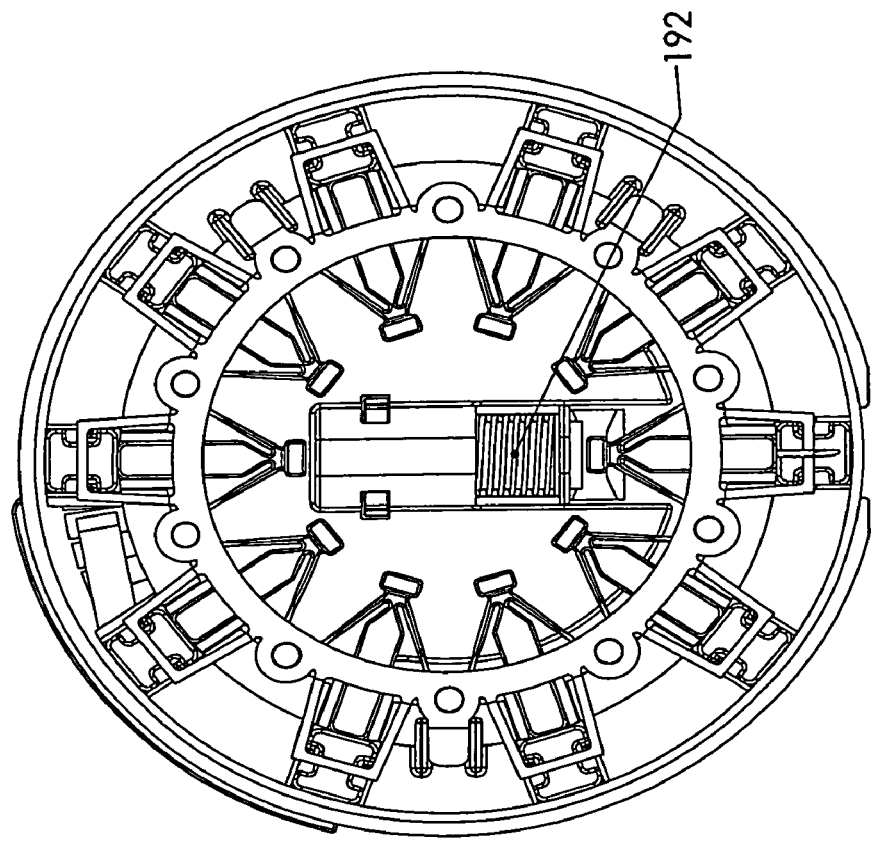
Figure 28A:
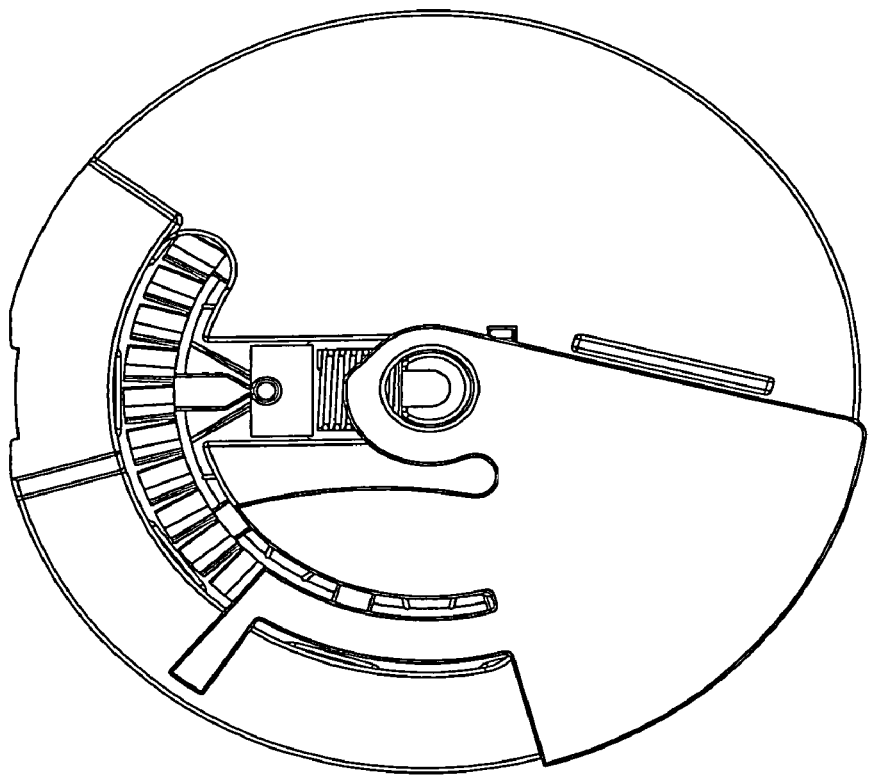

FIG. 25 shows the maximally rotated position of the control lever 202 or the plunger 184, in which the plunger 184 is held in this stressed position by a holding mechanism, which in this case is made up of the clamp spring 196 and the circular slot on plunger means 184. When the control lever 202 is turned back as shown in FIG. 26, the plunger 184 remains in its tensioned position. Now the protective cap 174 is moved out of the path of movement of the lancet 232 by the axially acting spring means 176. Finally, FIG. 27 shows the completed puncture process, in which the plunger 184 moves rapidly outward in the radial direction due to actuation of the holder in the form of spreading the clamp spring 196. It strikes the end of the holding plunger 172 and forces it outward along with the lancet 232. In the next moment, the withdrawal spring 192 produces a withdrawal movement of the plunger 184 back to the starting position, as shown in FIG. 28, in which the lancet tip is withdrawn inside the housing.

FIGS. 29-32 show details of a drive means or plunger mechanism for a lancing device, according to another embodiment of the present invention. These figures also explain the activation (tensioning) of the drive means for the lancets and the further rotation of the carrier by means of a single control element 238 which is formed, as an example, from the cover part already discussed. (This is independent of the arrangement and formation of the lancets on a rotatable carrier.) FIG. 29 shows a perspective view of the carrier components of this embodiment of the analytical device, with the components that make up the housing omitted. However, one can see the cover part 28 which has, at its inner side 36, not only the sliding guide rail 38 discussed in connection with FIG. 2 but also an arrangement of teeth 240 similar to a gear rack which follows the inner side 36. These teeth 240 engage with the gearing of a first gear wheel 242 in the plane of movement of the cover part 28. This first gear wheel 242 is arranged so that it is fixed on a shaft 244 extending perpendicularly to the plane mentioned. It has a second gear wheel 246 at its other end, the drive end. This second gear wheel can be moved into and out of mesh with an internal gear 82 of a carrier part 60. (Reference numbers corresponding to those in FIGS. 1 to 6 are used here.) The shaft 244 can be moved in a slot 248 in the specified plane of movement. When the cover element 28 is turned in the direction to open the application position discussed with FIG. 1, the shaft 244 is forced into the position shown in FIG. 29 at one end of the slot 248, in which the second gear wheel 246 meshes with the internal gear 82 of the carrier part 60 so that when the gear and shaft arrangement of carrier part 60 is rotated, and the arrangement of lancets is rotated clockwise. When the cover part 28 is slid or turned back to its initial position, then the gear wheel and shaft arrangement is forced to the opposite end of the slot 248, so that the teeth of the second gear wheel 246 come out of contact with the internal gear 82 of carrier part 60, thereby preventing reverse rotation of the arrangement of lancets 8.

The drive mechanism for a lancet in its operating position is designated by the reference number 250. It comprises a plunger mechanism 44 with a plunger 48 acting on a particular lancet. But the drive mechanism 250 also comprises a tensioning mechanism which, in this case, is made up of the second gear wheel 246 and a leaf spring 252, and a release mechanism 254 comprising a lever arrangement 256. One end of the leaf spring 252 is fastened to a leaf spring holder 258 at the second gear wheel 246 and the other end is fastened to a leaf spring holder 260 at a part 262 which can pivot with respect to the housing 4. This pivotable part 262 is part of the lever arrangement 256 that connects this part 262 with a button 264 at the puncture position 22 on the housing 4.

In a later outward movement of the cover part 28 the second gear wheel 246 not only turns the carrier part 60 farther, but it also pivots the leaf spring holder 258, thus moving the leaf spring 252 to a tensioned state. By actuation of the button 264, the other leaf spring holder 260 is likewise pivoted by the lever arrangement 256 so that the leaf spring 252 is suddenly released from its stable tensioned state past a dead point and the plunger 48 suddenly projects radially outward. That, in turn, likewise moves the lancet involved rapidly radially outward to carry out the puncture process. This course of the movement is shown in FIGS. 30, 31, and 32. Each of these figures shows a view from above (view b) and from below (view a) of the components of interest here inside the housing. FIG. 30 shows the drive means 250 of the blood withdrawal device in the non-activated initial state. The leaf spring 252 has a bowed shape between the leaf spring holders 258 and 260. Now, if as can be seen in FIG. 31, the cover part 28 is moved in the direction to open the application position 30, the carrier part 30, the shaft 244, and gear wheel 248 and the internal gear 82 of the carrier part 30 are rotated along with it by the gear wheel 242. At the same time, as shown in FIG. 31a, the leaf spring holder 258 at the second gear wheel 246 moves counterclockwise, and the leaf spring 252 takes on a form bent in an S shape. While this is going on, the leaf spring holder 260 and the position of the pivotable part 262 remain unchanged. The drive means 250 and its leaf spring 252 are now in the tensioned activated state. Now, if a user actuates the initiating means 254 by pressing the button 264 to start the puncture process, the lever arrangement 256 rotates the pivotable part 262 into the position shown in FIG. 32a. Thus the leaf spring 252 is moved past a dead point and the spring energy stored in the spring, tensioned in the S shape, is suddenly released. The spring returns again to its bowed shape as shown in FIG. 32a, but with curvature opposite that shown in FIG. 29a. Due to the coupling of the leaf spring 252 with the plunger 48 of the plunger mechanism 244, it is likewise projected suddenly outward.

FIGS. 33 and 34 show perspective views of a lancing device 302 for drawing a sample of blood from human or animal bodies for analysis, according to another embodiment of the invention. A cover part 304, which is preferably connected so that it can pivot, shown in FIG. 33, is omitted in FIG. 34. Inside a housing 306 a multiplicity of concentrically and radially arranged lancets 308 can be seen. A plunger system 310, which defines a plunging or puncturing direction 312, is visible in the center of the concentric arrangements.

FIGS. 35 and 36 show exploded views of the components housed within the housing 306. The lancets 308, which will be described in more detail below, can be seen. They have a protective cover or cap. FIG. 35 shows their radial arrangement. They can slide in radial directions on a carrier 314, preferably in the form of a circular disk, in guide paths or guide slots 316 of the carrier 314. FIG. 35 shows a circular disk 318 of spring steel above the lancet 308. It holds the lancets 308 in a manner that will be described in more detail below in the guide slots 316 of the carrier 308 so that they cannot be lost but can be slid radially.

Above the circular disk 318 there is shown a second carrier 320, with contacts 322 indicated schematically for test elements 324 provided in the vicinity of the contacts 322 to perform the blood analysis, that is, to determine the presence and content of some analytes, such as blood sugar, lactate, cholesterol or fructosamine. In one embodiment, the test elements 324 are loaded with the required sample of blood through a feed opening in the cover part 304 of the lancing device. In an alternate embodiment, an analysis test strip is passed out through a slot-like opening 328 and wetted with the sample of blood. Then an analysis is done amperometrically or potentiometrically, in known fashion, through the contacts 322 and an analysis system. Alternatively, separate analysis test strips are carried, and are inserted through the slot-like opening 328 to the contacts 322 on the carrier 320. In a preferred embodiment, the second carrier 320 carries a number of test elements 324 corresponding to that of the lancets 308. On the upturned visible side of the cover part 304 seen in FIG. 33 there is preferably a display, for example a digital or analog display for showing the time and/or sample analysis results. The device 302 is optionally fastened about the wrist of a user using a band in the manner of a typical wristwatch.

FIG. 36 shows the housing 306, which has a baseplate 332 with a cylindrical marginal section 334 projecting upward like a collar and a disk or dome-shaped elevation 336 in the center with sections with circular periphery 338. At the lower side of the baseplate 332 there is a disk-shaped part 342, with an actuating lever 340 which protrudes radially outwardly therefrom, and which can be rotated manually by a user. It is held at the bottom side of the baseplate 332 of the housing 306 by a cover part 344 on the baseplate side, so that it can be rotated. A retraction means in the form of a return spring 346 is also shown. The disk-shaped part 342 makes up a tensioning means 348 for the plunger system 310.

A plunger system 310 is mounted in the center of the dome-shaped elevation 336. It comprises a plunger piston 350, which will be described in more detail below, a plunger spring 352, and a recovery spring 354, a release 356 and a cover 358. The plunger system 310 is activated by rotating the actuating lever 40 and thus rotating the disk-shaped part 342, tensioning the plunger organ 350 against the pressure of the plunger spring 352. On actuation of the release means 356 the plunger organ 350 moves rapidly in the radial direction and carries out a puncture process together with a lancet 308. In the process, the lancet 308 moves through a path of travel, from a retracted position to an extended (or lancing) position, shown in FIGS. 33 and 34, wherein a finger or other sampling site of the subject has been positioned. The lancet tip penetrates the skin surface so that the user, immediately thereafter, can express a sample of blood from the wound.

FIG. 37 shows an enlarged perspective view of a lancet 308 with a protective covering. This covering involves a lancet body 362 of plastic or similar material, which is preferably injection-molded to cover the metal needle lancet 308 (which comprises the sharpened lancet tip 365), and a protective cap 364 in the region of the tip 365. In the injection-molding process, the lancet 308 is preferably held into the injection mold through an opening 366 left open in the body 362. Additionally, the lancet needle shaft may be flattened or otherwise deformed along its length to ensure capture and retention by the injection molding process. The body 362 and the protective cap 364 are preferably injection-molded in a single process. The body 362 and the protective cap 364 meet at a thin-walled transition region 368, which forms an area of weakening 370. This weakened area can be further weakened by cutting or otherwise forming a slit almost through the plastic. In alternate embodiments, the body 362 and the protective cap 364 are formed as separate components. An opening 372 is preferably formed in the transition region 368, which promotes development of the thin-walled area of weakening 370. This opening 372 can, for instance, be produced in the injection-molding process by another holder for the lancet 308.

Figure 38A:
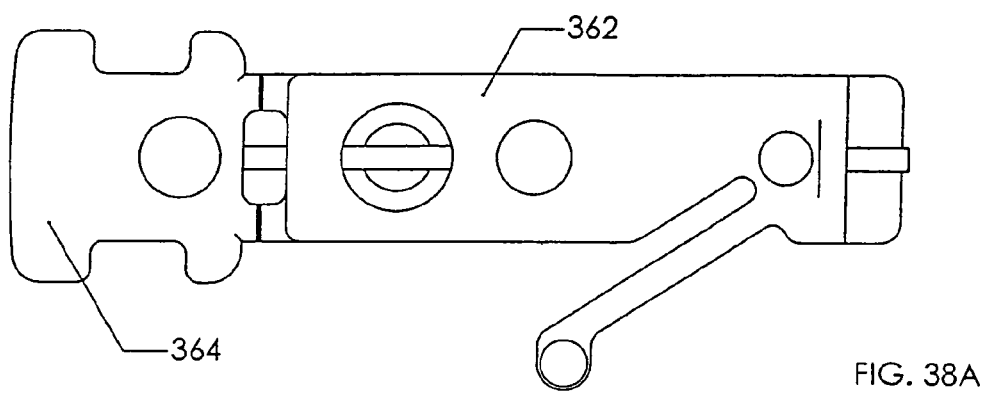
Figure 38B:
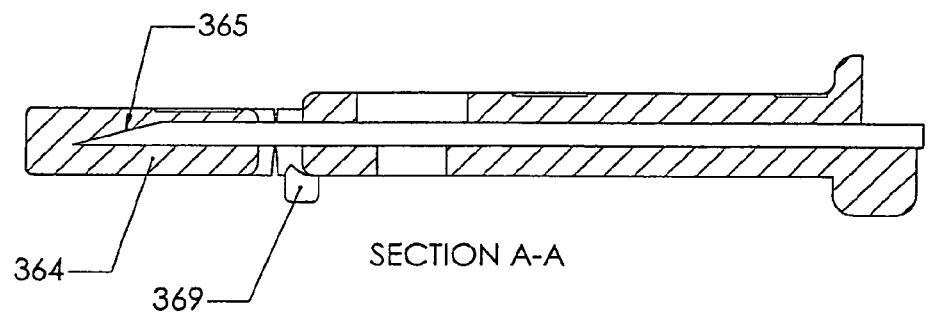
Figure 38C:
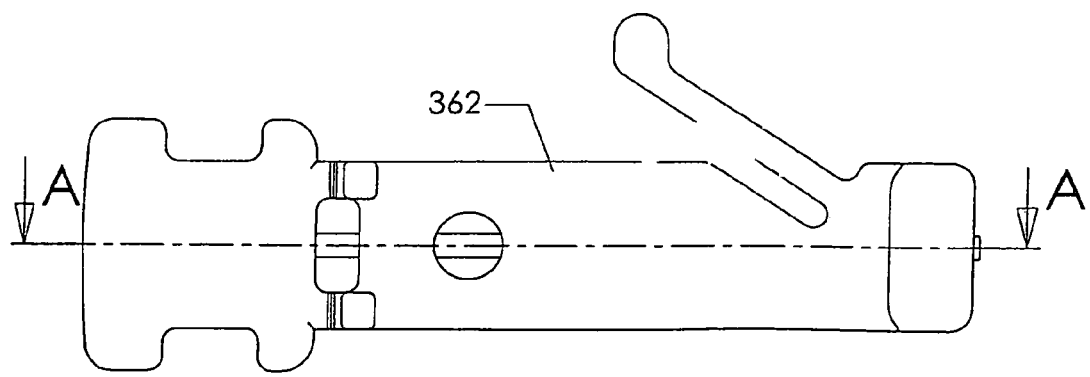

A resilient tongue or pin 374 projects from the holder 362 at an oblique angle, for example of about 40° to the longitudinal direction of the lancet 308, and preferably is integrally formed with the body 362, and has a rounded free end 376. The tongue 374 can be spread apart or is elastically and resiliently deformable in the direction of the double arrow 378 with respect to the body 362 for the lancet 308. The tongue 374 assures stabilization in the plane of application for the body 362 and, for example, prevents tilting about the longitudinal direction. The tongue can also serve to minimize oscillation of the lancet. After a plunger process has been carried out, it can initiate a withdrawal force into the holder, entering the lancet 308 and withdrawing it. It also makes sure that the lancet does not slip out of the guide slots 316 of the carrier 314. A post 369 keeps the lancet from falling inward after use by abutting against a cooperating lip or projection on the carrier. The protective cap 364 preferably has an H-shape in the plan view, having guide slots on both sides, with which it is held immovably in the longitudinal direction of lancet 308 (i.e., in the radial direction, on carrier 314), but it can slide transversely, perpendicular to the longitudinal direction of lancet 308, with respect to the carrier. FIGS. 38a-c show additional detail of the lancet with the holder and protective cap. In its longitudinal direction, including the holder 362 and protective means 364, the lancet is preferably about 12.5 mm long. FIGS. 39a-c show example processes of production for separating the lancets 308 covered by the body 362 and protective capping means 364 during production. The end of the body 362 distal from the protective cap 364 preferably comprises at least one shoulder or flange 418 projecting transversely outward from a side of the body, and has a step or recess 382. More preferably, a pair of opposed flanges project from opposite sides of the body 362 for engagement with the drive mechanism, to withdraw the lancet along its longitudinal axis without misalignment during cocking. The lancet needle 308 is cut off from a length of wire or tube by upper and lower knives 384, 386 shown. The upper knife 384 is placed nearly in contact with the step 382 so that its position can be defined with respect to the holder 362 and the lancet 308, and the lancet needle 308 is cut off substantially flush with the lancet body 362.

FIGS. 40-43 show the arrangement of the lancets 308 together with the bodies 362 and protective caps 364 on the carrier 314. The carrier 314 is preferably a generally circular disk having a raised pattern molded on its upper face. In the depicted embodiment, the carrier comprises ten radial guide channels, each channel bounded by a supporting wall 388 in the plane of the disk and two lateral guide walls 390 which are perpendicular to the disk and radially oriented. A lancet 308, with holder 332 and protective cap 364, is translationally slidable within each radial guide channel. The individual lancets 308 are inserted into the guide depressions from above, i.e., in the axial direction. Then they take up the positions shown in FIGS. 34 and 42. It can be seen that there is no lancet 308 in one arc segment 391 of the carrier. When the carrier is inserted from above into the housing 306, the carrier 314 is positioned so that the arc segment 391 is oriented above the plunger system 310, such that the radial outer end of the plunger system 310 extends into this circle segment 391. Then the plunger means 350 is arranged within the circle segment 391 as if between two adjacent lancets, the first and last lancets. A positioning aid in the form of an arrow-shaped profile of the circular disk 318 is preferably provided to assist in the installation.

A retainer 318, preferably formed of a generally circular ring of spring steel, holds the lancets 308 in their positions within the guide depressions 316 of the carrier 314. For this purpose the circular disk 318 is inserted, with a number of openings 392 on corresponding pins 394 of the carrier 314. The pins are expanded or attached to the disk 318, as for example by ultrasonic welding. The circular disk 318 of spring steel has radially projecting tongues 396 which are oriented parallel to the supporting wall 388 and which hold and guide a particular housing body 362 of a particular lancet 308. Another tongue 398, formed as a U-shaped loop, extends around each tongue 396 and the two legs of the U shape connect to the circular disk 318. The loop-shaped tongue makes up a displacement means 399 for the protective cap 364 to move it out of the path of movement of the lancet 308. The connecting pins 400 of the tongue 398 running in the peripheral direction are slightly angled upward from the plane of the circular disk 318 and are somewhat flexible. Thus each one defines an attachment plane that is slightly oblique to the plane of the circular disk 318. The connecting pins 400 and the planes formed by each of them are also oblique to the upper side 402 of the particular protective cap 364. Likewise, the particular connecting pin 400 rests, under light pressure, on the upper side 402 of the protective cap 364 involved. If a holder 362 with the injection-molded lancet 308 is drawn radially inward and the region of weakening 370 between the holder 362 and the protective cap 364 is broken, then the loop-shaped tongue 398 with its connecting pin 400 forces the protective capping means 364 downward, transversely to the direction of puncture or the longitudinal direction of lancet 308, into the position shown in FIG. 43. In this disposal position 403 the surface of the connecting pin 400 of the spring tongue 398 lies against the top 402 of the particular protective capping means 364. (FIG. 43 shows the lancet 308 after the puncture process has been carried out.)

One can also see, in FIGS. 40, 42 and 43, strip-shaped guide posts 404 that enter the guide depressions 380 of the particular protective cap 364. The particular protective cap 364 can be slid on these guide posts 404 in the axial direction, i.e., perpendicular to the radially oriented puncture direction. At the same time these guide posts 404 hold a particular protective cap 364 immovably in the radial direction, so that when the holder 362 is drawn inward the region of weakening 370 can be broken. Later, as explained above, a particular protective cap 364 is held in a depression 406 in the carrier 314, which forms the disposal position 403 for the protective cap. Then each protective cap is held immovably in this depression 406 by the loop-shaped spring tongue 398 to prevent any disturbing rattling noise.

FIGS. 44-45 show the housing 306 with and without the components involved with the drive system 310. It can be seen that the dome-shaped elevation 336 in the housing 306 forms a holder for the plunger 350, the plunger spring 352 and the withdrawal spring 354. The cover 358 holds these components so that they cannot be lost and can be slid longitudinally into the holder, in the radial direction. FIG. 46 shows, in a greatly enlarged presentation, the plunger 350, which is designed as a piston or a ram. Its outside diameter is stepped down, so that it has an axial step 408 that supports one end of the withdrawal spring 354. The other end of the withdrawal spring 354 is supported against one face 410 of the dome-shaped elevation 336. The plunger spring 352 is supported at the end with the greater diameter 412, with the other end supported against a face 412 of the dome-shaped elevation 336. The plunger means 358 further comprises a coupling region 416, which is open in the direction of plunger movement, as well as in the peripheral direction. This coupling region 416 is complementary to a rear gripping region 418 (see FIG. 37) of the lancet body 362 and can hold that region so that the body 362 can be coupled to the plunger 350, forming a secure engagement with the plunger 350. For the orientation of the plunger means 350 seen in FIG. 45, a holder 362 for a lancet 308 can be rotated into this coupling region 316 by rotating the carrier 314, as can be seen in FIG. 34. If the plunger 350 is drawn back radially inward, locked together with a lancet body 362 for a lancet 308, so that the plunger spring 352 is tensioned, then the protective cap 364, which is constrained against motion in the radial direction, cannot follow, and there is a break in the region of weakening 370 between them. As soon as the free sharp end 365 of the lancet 308 comes free of the protective cap 364, the cap is moved into the disposal position 403, as described previously, under the action of the loop-shaped spring tongue 398. The lancet 308 along with the body 362 follows the tensioning movement of the plunger 350 during this operation. Now the puncture system 310 is in the activated or armed state, and can be actuated or triggered to carry out the puncture process by pressing the release 356.

As can be seen from FIG. 46, the plunger 350 has a tensioning cam 420 projecting transverse to the direction of puncturing. This tensioning cam 420 extends through a linear hole 422, which runs radially into the baseplate 332 of the housing 306. Thus the tensioning cam 420 projects downward past the bottom side of the baseplate 332. It enters an opening 424 in the disk-shaped part 342, mentioned initially, with the radially projecting lever 340. This opening forms a cam guide curve 426 such that the tensioning cam is displaced radially inward along this cam guide curve 426 by rotation of the disk-shaped part 342. By rotating the radially projecting actuating lever 340 in the direction of arrow 428 (FIG. 45) the plunger 350 is moved radially inward against the force of the plunger spring 352 along the cam guide curve 426 and the tensioning cam 420 until a catch arm 430 of the release 356 catches in a catch cutout 432 in the larger-diameter section of the plunger means 350, initially holding the plunger means 350 in the tensioned state. When the actuating lever 340 is released, it returns to its initial position under the action of the withdrawal spring 346. As mentioned previously, the actuating lever 340 and the disk-shaped part 342 make up a tensioning means 348 for the plunger system 310.

A resilient pin 434 extends in the peripheral direction on the disk-shaped part 342 can be seen in FIG. 48. Because of a slotted separation 436, which extends generally in the peripheral direction, the pin 434 can be deflected slightly in the axial direction toward the plane of part 342 (see arrow 438). At the free end of the pin 434 there is a projection 440 extending in the axial direction. It enters the interior of the housing 306 through a slot-shaped cutout 442 extending peripherally in the base 332 of the housing 306, as can be seen in FIG. 45. When the actuating lever 340 of part 342 is pivoted, projection 440 moves along this slot-shaped cutout 442. The projection 440 is rotationally locked to the carrier 314 until the pin 434 with its projection 440 slides along the underside of the baseplate 332 of the housing 306 on a wedge-shaped ramp means 444, as can be seen from FIGS. 44 and 45. In this sliding movement, the pin is deflected downward and the projection 440 is withdrawn into the baseplate 332, so that it is no longer rotationally locked to the carrier 314. Therefore it is only during this phase that the tensioning cam 420 does not move inward. During the first phase of movement of projection 440 up to the ramping means 444, rotation of the carrier 314 brings a lancet 308 that has not yet been used into the working position. At this point, the carrier 314 is no longer located by the disengaged tooth 440, and will now be more accurately positioned by the interaction between one of a series of spaced precision alignment grooves 331 in the interior base of the housing body with a cooperating tooth of the cantilevered ratchet lever 393. In this process the holder 362, with its-rear gripping means 418 arranged radially internally is rotated into the coupling region 416 of the plunger means 350. Now the opening 424 in the disk-shaped part 342 is designed and arranged so that the cam 420 of the plunger means 350 interacts at that moment with the cam guide path 426, in which the next successive holder 362 has entered the coupling region 416 of the plunger means 350 and cannot be carried farther. In this position, the plunger means 350 together with the holder 362 and the lancet 308, are drawn radially inward by the tensioning cam 420 sliding along the cam guide curve 426 until the catch arm 430 catches, with a trapping hook, in the trap depression 432 of the plunger means 350. As has been described previously, during this process of tensioning the plunger system 310 the region of weakening 370 between the lancet body 362 and the protective cap 364 is broken and the protective cap is moved into the disposal position shown in FIG. 43, leaving the path of movement of the lancet 308 clear. Now, if the release 356 actuates the plunger system 310, the plunger 350 moves rapidly in the radial direction along with the holder 312 and the lancet 308, and the free end 365 of the lancet 308 moves, in an extremely short time, past the application position 360 to the outside of the housing 306, so that it can penetrate the skin surface of a user in an extremely short time. During this puncture process the withdrawal spring 354 is tensioned. Then it quickly pulls the holder 362 together with the lancet 308 back into the interior of the housing 306. The spreadable pin 374 then also supports the correct positioning of the used lancet 308 on the carrier 314 and, when a used carrier cassette is replaced by a new one, it prevents the used lancet with the holder 362 slipping in the radial direction out of the guide depressions 316 in the carrier 314, assuring reliable disposal of used lancets. FIG. 49 shows the underside of the baseplate 332 of the housing 306, that is, without the base cover part 344 shown in FIG. 36.

The lancing device of this embodiment of the invention can be produced in the nature and size of a wrist-watch that can be worn at the user's wrist. The lancing device has a plurality (for example about 5 to 12) of lancets, which are inserted as a cassette onto the carrier 14 in the housing 6. A user opens the cover part 304 and inserts a carrier cassette into the inside of the housing, noting the positioning of certain orientation marks, such as indicator 397, which is initially aligned with the position of the piston of the drive mechanism. The cover part 304 is then closed and a first lancet 308 is moved into the operating position by operation of the actuating lever 340. In that process the lancet 308, or its body 362, is engaged together with the plunger 350 and, in connection with that, is drawn radially inward. The protective cap 364 is thereby removed, and is moved, transversely to the direction of puncture 312, into a disposal position 403 on the carrier 314. When the lancing device 310, activated in this manner, is released, the plunger 350, together with the body 362 and the lancet 308, is accelerated in the radial direction by release of the plunger spring 352, as by a blow. It is returned to the initial position again by the withdrawal spring 354. By another actuation of the activating lever 340, the carrier is advanced by one incremental position, past the projection 440 of the carrier 314. That is, the used lancet is rotated out of the operating position and a lancet that has not yet been used is moved into the operating position, etc. When all of the lancets have been used, a rotation stop prevents further movement of the carrier 14. This indicates to the user that a cassette with new lancets must be inserted for further use. FIG. 45 shows the guide wall 601 is removed or shortened to allow easy movement of the lancet as it is removed from the piston While the invention has been described with reference to preferred and example embodiments, it will be understood by those skilled in the art that a variety of modifications, additions and deletions are within the scope of the invention, as defined by the following claims.

What is claimed is:

1. A lancing device comprising:
   a housing;
   a cassette removably mounted within said housing, said cassette comprising at least one lancet having a lancet body and a protective cap;
   a piston for propelling the lancet along a path of travel, said piston having a lancet coupling portion for releasably engaging and retracting the lancet to separate the lancet body and the protective cap along a retraction portion of the path of travel of the lancet, and thereafter advance the lancet along the path of travel into a lancing position;
   at least one guide member per lancet and in association therewith, the guide member being aligned transversely to the path of travel of the associated lancet within the cassette for engaging the separated protective cap of the associated lancet to guide the protective cap out of the path of travel; and
   a retainer position within the cassette adjacent each said at least one guide member to retain the separated protective cap.

2. The lancing device of claim 1, further comprising a biasing element for moving the protective cap out of the path of travel of the lancet after separation of the protective cap from the lancet body.

3. The lancing device of claim 2, wherein the biasing element moves the cap transversely out of the lancet travel path within a plane that is perpendicular to the lancet travel path.

4. The lancing device of claim 1, wherein the protective cap comprises a pair of recesses in opposed sides thereof, and wherein the at least one guide member comprises a pair of guide posts slidably engaged in said recesses to guide said protective cap out of the path of travel of the lancet.

5. The lancing device of claim 1, further comprising a cocking mechanism for arming the piston.

6. The lancing device of claim 5, wherein the cassette comprises a plurality of the lancets and the lancing device further comprises an advancing mechanism for sequentially advancing the lancets into an operating position, and wherein the cocking mechanism and the advancing mechanism are coupled together so that they operate together.

7. The lancing device of claim 6, wherein actuation of the cocking mechanism actuates the advancing mechanism to advance the cassette to sequentially engage each of said plurality of lancets with said piston.

8. The lancing device of claim 5, wherein actuation of the cocking mechanism retracts said piston to cause separation of the lancet body and the protective cap.

9. The lancing device of claim 1, wherein said cassette comprises a plurality of lancets radially arranged about an axis.

10. The lancing device of claim 9, wherein said cassette further comprises radially extending guides defining the path of travel of the lancet.

11. The lancing device of claim 9, wherein said plurality of lancets lie in a plane, and wherein the piston propels the lancet along a path of travel within that plane.

12. The lancing device of claim 9, further comprising a cocking mechanism for sequentially advancing the cassette through a series of positions wherein one of said plurality of lancets is engaged with said piston.

13. The lancing device of claim 12, wherein actuation of the cocking mechanism drives the piston to separate the lancet body from the protective cap.

14. The lancing device of claim 9, wherein said cassette further comprises a plurality of spring elements aligned for engagement with the protective caps of said plurality of lancets to move the protective caps out of the path of travel after separation of the protective cap from the lancet body.

15. The lancing device of claim 14, wherein said retainer further comprises a plurality of guide tongues for defining the path of travel of said lancets.

16. The lancing device of claim 14, wherein each of said spring elements comprises a generally U-shaped loop.

17. The lancing device of claim 1, wherein the lancet body and the lancet coupling portion of the piston comprise interengaging coupling elements, said interengaging coupling elements comprising a tapered lead-in section for aligning said lancet body and said piston for engagement.

18. The lancing device of claim 1, wherein each lancet further comprises a resilient tongue extending from the lancet body.

19. The lancing device of claim 1, wherein said housing resembles a wristwatch housing, and further comprising a wristband.

20. The lancing device of claim 1, further comprising sample collection and analysis media.

21. The lancing device of claim 1, wherein said cassette further comprises an alignment indicator for identifying proper alignment of said cassette with the housing upon installation.

22. A lancing device comprising:

a housing;

a cassette removably mounted within said housing, said cassette comprising at least one lancet having a lancet body and a protective cap;

a piston for propelling the lancet along a path of travel, wherein said piston releasably engages the lancet and causes separation of the lancet body and the protective cap along at least a portion of the path of travel of the lancet;

wherein said cassette comprises a plurality of lancets radially arranged about an axis; and wherein said cassette further comprises a retainer having a plurality of spring elements extending therefrom, said spring elements directly engaging and biasing the protective caps of said plurality of lancets to move the protective cape out of the path of travel after separation of the protective cap from the lancet body, the retainer and the protective caps comprising separate components.

23. The lancing device of claim 22, wherein said retainer further comprises a plurality of guide tongues for defining the path of travel of said lancets.

24. The lancing device of claim 22, wherein each of said spring elements comprises a generally U-shaped loop.

25. A lancing device comprising:

a housing;

a cassette removably mounted within said housing, said cassette comprising a plurality of lancets, each lancet having a lancet body and a protective cap; a piston for propelling a lancet along a path of travel, said piston having a lancet coupling portion for releasably engaging and retracting the lancet to separate the lancet body and the protective cap along a retraction portion of the path of travel of the lancet, and thereafter advance the lancet along the path of travel into a lancing position;

a plurality of guide members corresponding to the plurality of lancets and at least one of said guide members per each lancet and in association therewith, each guide member being aligned transversely to the path of travel of the corresponding lancet within the cassette for engaging the separated protective cap of the corresponding lancet to guide the protective cap out of the path of travel;

and a retainer positioned within the cassette adjacent each guide member to retain the separated protective cap.

* * * * *